US 7,446,174 B2

(12) United States Patent
Desjarlais et al.

(10) Patent No.: US 7,446,174 B2
(45) Date of Patent: Nov. 4, 2008

(54) PROTEIN BASED TNF-α VARIANTS FOR THE TREATMENT OF TNF-α RELATED DISORDERS

(75) Inventors: John R. Desjarlais, Pasadena, CA (US); Paul Michael Steed, Chapel Hill, NC (US); Jonathan Zalevsky, Riverside, CA (US); David Edmund Szymkowski, Monrovia, CA (US)

(73) Assignee: Xencor, Inc., Monrovia, CA (US)

(*) Notice: Subject to any disclaimer, the term of this patent is extended or adjusted under 35 U.S.C. 154(b) by 482 days.

(21) Appl. No.: 11/108,001

(22) Filed: Apr. 14, 2005

(65) Prior Publication Data

US 2005/0265962 A1    Dec. 1, 2005

Related U.S. Application Data

(63) Continuation-in-part of application No. 10/963,994, filed on Oct. 12, 2004, and a continuation-in-part of application No. 10/262,630, filed on Sep. 30, 2002, now Pat. No. 7,244,823, and a continuation-in-part of application No. 09/981,289, filed on Oct. 15, 2001, now Pat. No. 7,101,974, and a continuation-in-part of application No. 09/945,150, filed on Aug. 31, 2001, now abandoned, and a continuation-in-part of application No. 09/798,789, filed on Mar. 2, 2001, now Pat. No. 7,056,695.

(51) Int. Cl.
C07K 17/00    (2006.01)
G01N 33/53    (2006.01)

(52) U.S. Cl. .................. 530/351; 435/69.5; 435/7.1; 435/335

(58) Field of Classification Search .................. None
See application file for complete search history.

(56) References Cited

U.S. PATENT DOCUMENTS

| | | | |
|---|---|---|---|
| 4,677,063 A | 6/1987 | Mark et al. |
| 4,677,064 A | 6/1987 | Mark et al. |
| 4,879,226 A | 11/1989 | Wallace et al. |
| 4,894,439 A | 1/1990 | Dorin et al. |
| 4,948,875 A | 8/1990 | Tanaka et al. |
| 4,990,455 A | 2/1991 | Yamagishi et al. |
| 5,028,420 A | 7/1991 | Masegi et al. |
| 5,081,021 A | 1/1992 | Mizuno et al. |
| 5,151,349 A | 9/1992 | Tanaka et al. |
| 5,160,483 A | 11/1992 | Postlethwaite et al. |
| 5,180,811 A | 1/1993 | Doerper et al. |
| 5,262,309 A | 11/1993 | Nakamura et al. |
| 5,288,852 A | 2/1994 | Yamada et al. |
| 5,422,104 A | 6/1995 | Fiers et al. |
| 5,478,925 A | 12/1995 | Wallach et al. |
| 5,512,544 A | 4/1996 | Wallach et al. |
| 5,597,899 A | 1/1997 | Banner et al. |
| 5,606,023 A | 2/1997 | Chen et al. |
| 5,652,353 A | 7/1997 | Fiers et al. |
| 5,695,953 A | 12/1997 | Wallach et al. |
| 5,773,582 A | 6/1998 | Shin et al. |
| 5,888,814 A | 3/1999 | Kriegler et al. |
| 5,889,156 A | 3/1999 | Kriegler et al. |
| 6,188,965 B1 | 2/2001 | Mayo et al. |
| 6,269,312 B1 | 7/2001 | Mayo et al. |
| 6,403,312 B1 | 6/2002 | Dahiyat et al. |
| 2001/0032052 A1 | 10/2001 | Mayo et al. |
| 2001/0039480 A1 | 11/2001 | Mayo et al. |
| 2002/0004706 A1 | 1/2002 | Mayo et al. |
| 2002/0009780 A1 | 1/2002 | Dahiyat et al. |
| 2002/0048772 A1 | 4/2002 | Dahiyat et al. |
| 2002/0090648 A1 | 7/2002 | Dahiyat et al. |
| 2002/0106694 A1 | 8/2002 | Mayo et al. |

FOREIGN PATENT DOCUMENTS

| | | |
|---|---|---|
| CA | 2005051 | 6/1990 |
| EP | 0 254 647 A2 | 1/1988 |
| EP | 0 486 908 A3 | 5/1992 |
| EP | 0 251 037 B1 | 6/1994 |
| EP | 0 251 037 A2 | 7/1998 |
| JP | 60-252496 | 12/1985 |
| JP | 03-180194 | 8/1991 |
| JP | 03-297388 | 12/1991 |
| JP | 04-079880 | 3/1992 |

(Continued)

OTHER PUBLICATIONS

Arakawa et al., "Alteration in folding efficiency and conformation of recombinant human tumor necrosis factor-alpha by replacing cysteines 69 and 101 aspartic acid 69 and arginine 101," Protein Eng 3(8):721-724 (Aug. 1990).
Barbara et al., "Tumour necrosis factor-alpha (TNF-alpha): the good, the bad and potentially very effective," Immunol Cell Biol 74(5):434-443 (Oct. 1996).
Cen et al., "Glycine68 to histidine73 has an important role in the function of human tumor necrosis factor alpha," Biochem Mol Biol Int 43(1):47-52 (Sep. 1997).
Creasey et al., "Biological effects of recombinant human tumor necrosis factor and its novel muteins on tumor and normal cell lines," Cancer Res 47(1):14-149 (Jan. 1987).

(Continued)

Primary Examiner—Christine J Saoud
Assistant Examiner—Jegatheesan Seharaseyon
(74) Attorney, Agent, or Firm—Morgan Lewis & Bockius LLP; Robin M. Silva, Esq.; David C. Foster, Esq.

(57) ABSTRACT

The invention relates to novel proteins with TNF-α antagonist activity and nucleic acids encoding these proteins. The invention further relates to the use of the novel proteins in the treatment of TNF-α related disorders.

20 Claims, 42 Drawing Sheets

FOREIGN PATENT DOCUMENTS

| | | |
|---|---|---|
| JP | 04-182497 | 6/1992 |
| JP | 04-182498 | 6/1992 |
| JP | 04-368398 | 12/1992 |
| JP | 05-255393 | 10/1993 |
| JP | 05-271287 | 10/1993 |
| JP | 05-271289 | 10/1993 |
| WO | WO 90/07579 A1 | 7/1990 |
| WO | WO 94/18325 A1 | 8/1994 |
| WO | WO 98/47089 A1 | 10/1998 |
| WO | WO 98/51344 A1 | 11/1998 |
| WO | WO 00/23564 A2 | 4/2000 |
| WO | WO 01/25277 A1 | 4/2001 |
| WO | WO 01/59066 | 8/2001 |
| WO | WO 01/64889 A2 | 9/2001 |

OTHER PUBLICATIONS

Jones et al., "The three-dimensinal structure of tumour necrosis factor," Prog Clin Biol Res 349:321-327 (1990).

Kinstler, O et al., "Mono-N-terminal poly(ethylene glycol)-protein conjugates," *Advanced Drug Delivery Reviews* 54:477-485 (2002).

Loetscher et al, "Human tumour necrosis factor alpha (TNF alpha) mutants with exclusive specificity for the 55-kDa or 75-kDa TNF receptors," J Biol Chem 268(35):26350-26357 (Dec. 1993).

Masegi et al., "Characterization of a novel human tumor necrosis factor-alpha mutant with increased cytotoxic activity," Jpn J Cancer Res 86(1):72-80 (Jan. 1995).

Narachi et al., "Role of single disulfide in recombinant human tumor necrosis factor-alpha," J Biol Chem 262(27)13107-13110 (Sep. 1987).

Ngo, J.T. et al., "Computational Complexity, Protein Structure Prediction, and the Levinthal Paradox," *The Protein Folding Problem and Tertiary Structure Prediction*, Merz, Jr. and Le Grand, Eds., Birkhauser, Boston 1994, pp. 492-495.

Peitsch, M.C. and Tschopp, J., "Comparative molecular modelling of the Fas-ligand and other members of the TNF family," Mol Immunol. Jul. 1995;32(10):761-72.

Roberts, M.J. et al., "Chemistry for peptide and protein PEGylation," *Advanced Drug Delivery Reviews* 54:459-476 (2002).

Sato et al., "Differentiation induction by a tumor-necrosis-factor mutant 471 in human myelogenous leukemic cells via tumor-necrosis-factor receptor-p55," Int J Cancer 78(2):223-232 (Oct. 1998).

Shin et al., "A novel tumor necrosis factor-alpha mutant with significantly enchanced cytotoxicity and receptor binding affinity," Biochem Mol Biol Int 44(6):1075-1082 (May 1998).

Tavernier et al., "Analysis of the structure-function relationship of tumour necrosis factor. Human/mouse chimeric TNF proteins: general properties and epitope analysis," J Mol Biol 211(2):493-501 (Jan. 1990).

Van Ostade, X., et al., "Localization of the active site of human tumour necrosis factor (hTNF) by mutational analysis," EMBO J 10(4):827-836 (1991); Erratum in EMBO J 11(8):315 (1992).

Van Ostade et al., "Structure-activity studies of human tumour necrosis factors," Protein Eng 7(1):5-22 (Jan. 1994).

Van Ostade et al., "Two conserved tryptophan residues of tumor necrosis factor and lymphotoxin are not involved in the biological activity," FEBS Lett 238(2):347-352 (Oct. 1988).

Van Ostade, "Human TNF mutants with selective activity on the p55 receptor," Nature 361:266-269 (Jan. 1993).

Watson, "TNF inhibitors: A review of the recent patent literature", Drugs, 2002, 5(12):1151-1161.

Wells, J.A., "Additivity of Mutational Effects in Proteins," *Biochemistry* 26(37):8509-8517 (1990).

Xi et al., "Biological activities of human tumor necrosis factor-alpha and its novel mutants," Biochem Mol Biol Int 38(4):855-862 (Apr. 1996).

Xi et al., "Biological activities of human tumor necrosis factor-alpha and its novel mutants," Biochem Mol Biol Int 38(6):1183-1189 (May 1996).

Yamagishi et al., "Mutational analysis of structure—activity relationships in human tumor necrosis factor-alpha," Protein Engineering 3(8):713-719 (1990).

Yamamoto et al., "Histidine-15: an important role in the cytotoxic activity of human tumor necrosis factor," Protein Eng 2(7):553-558 (May 1989).

Zhang et al., "Site-directed mutational analysis of human tumor necrosis factor-alpha receptor binding site and structure-functional relationship," J Biol Chem 267(33):24069-24075 (Nov. 1992).

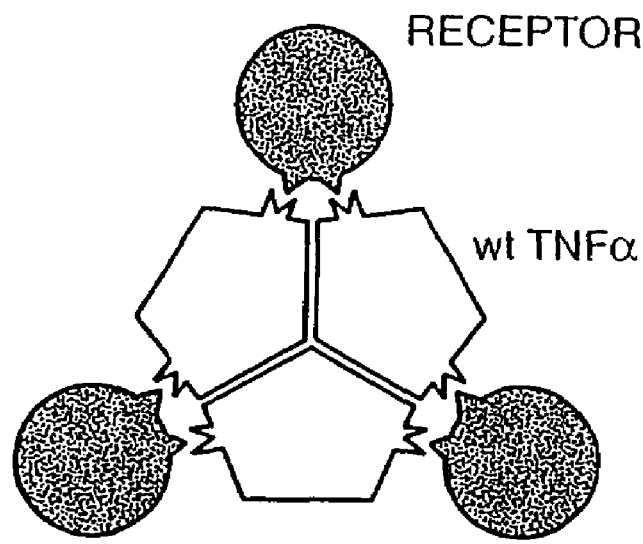
FIG._1A
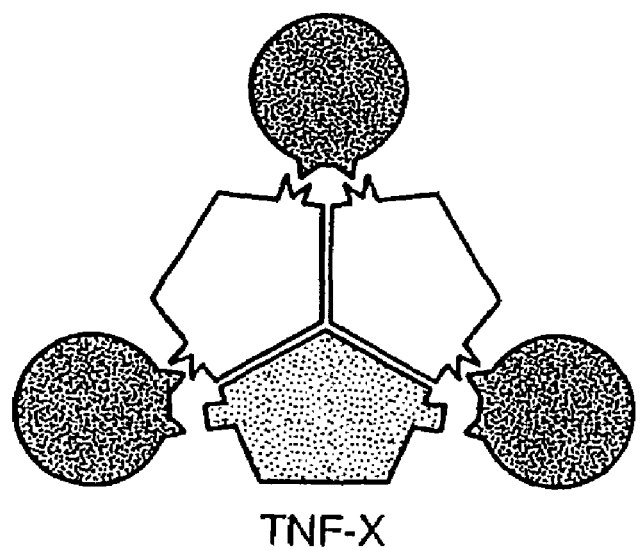
FIG._1B

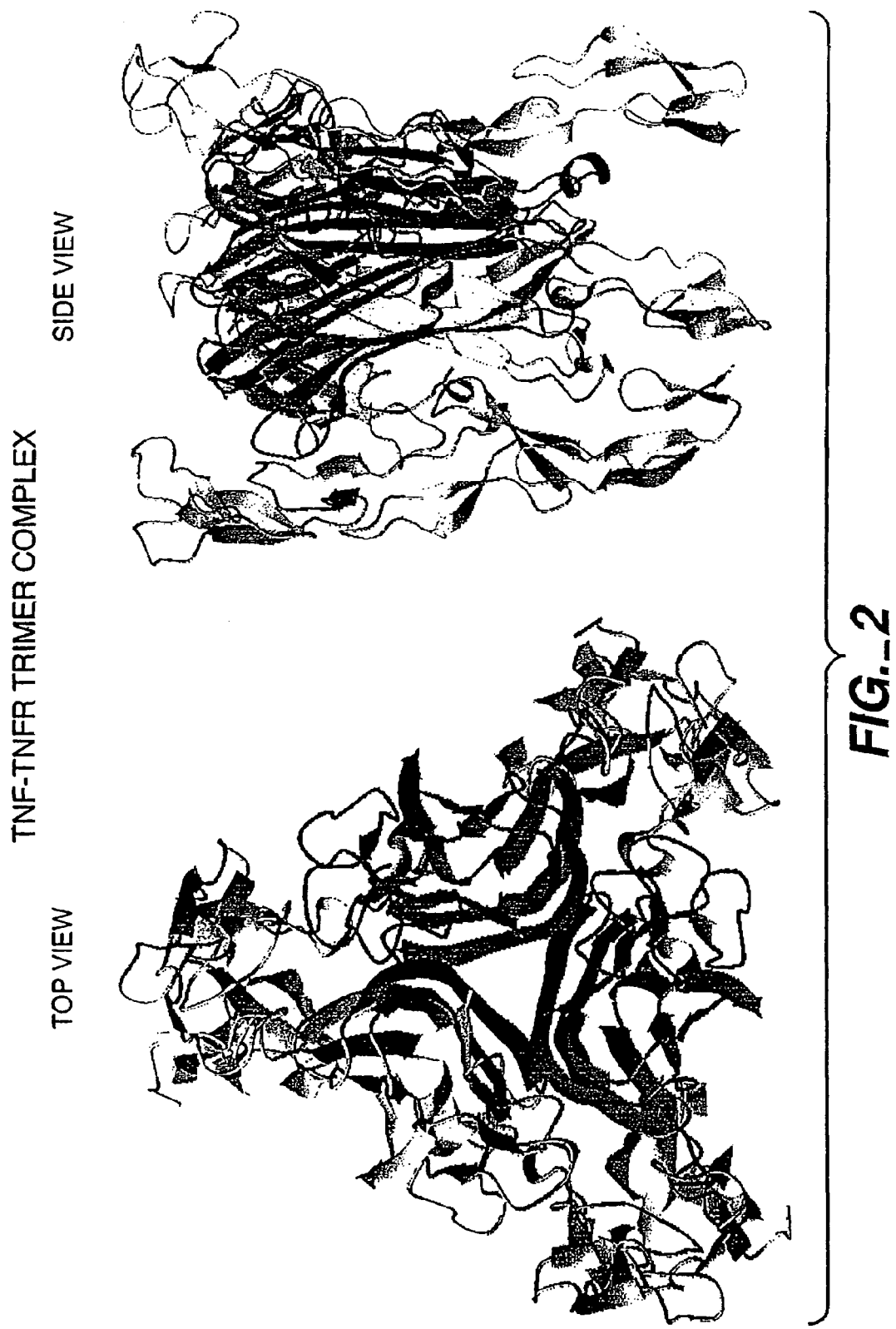
FIG._2

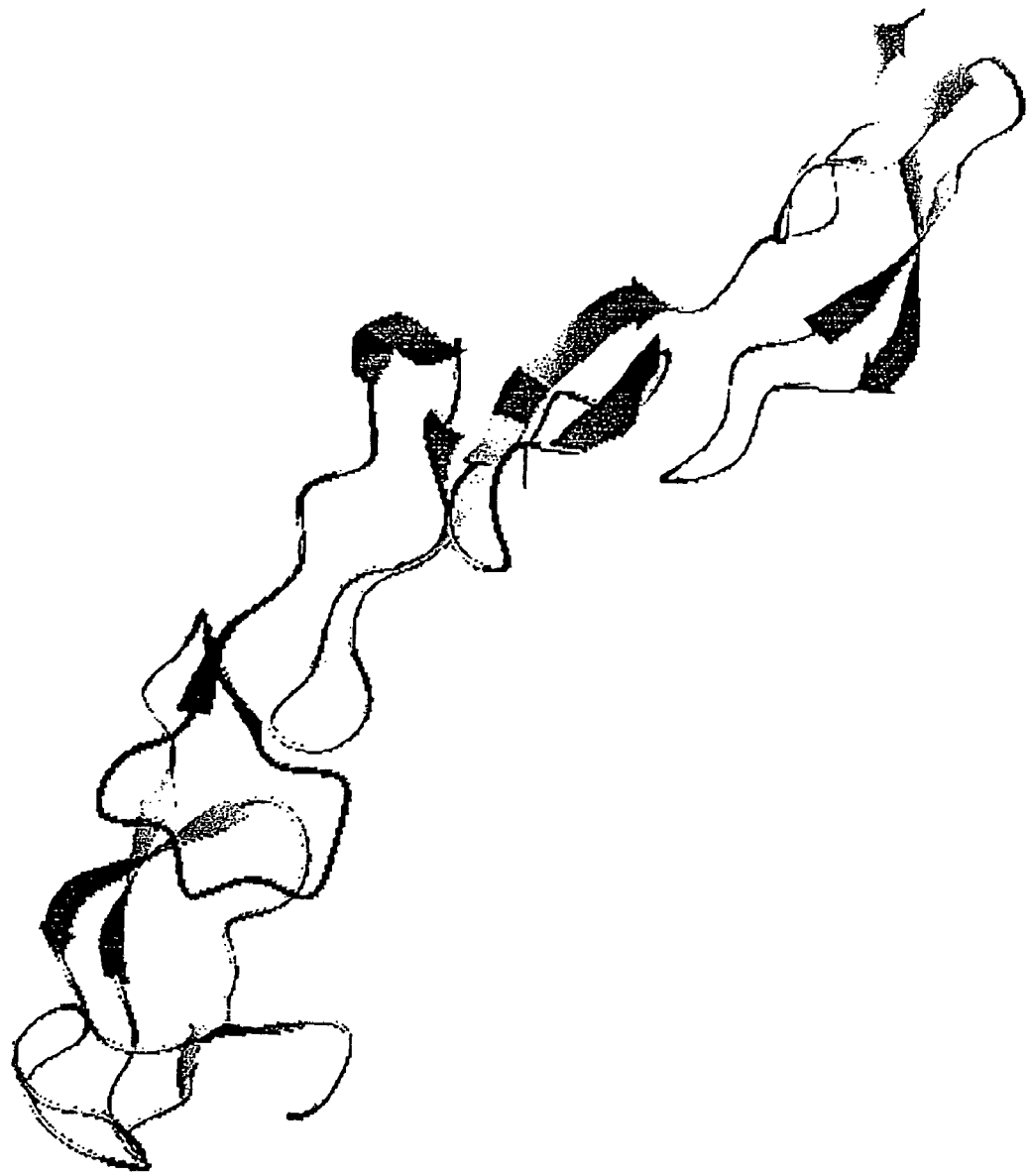
FIG._3

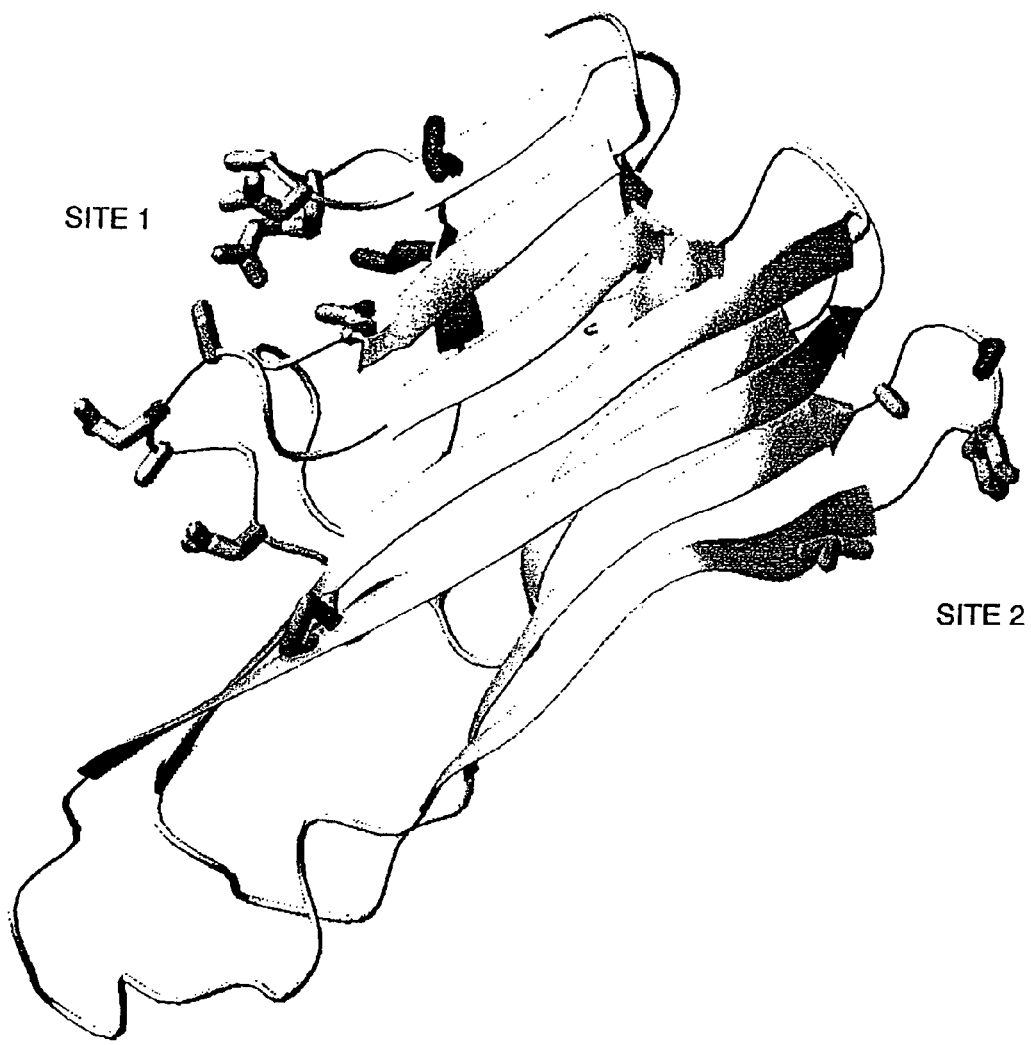
FIG._4

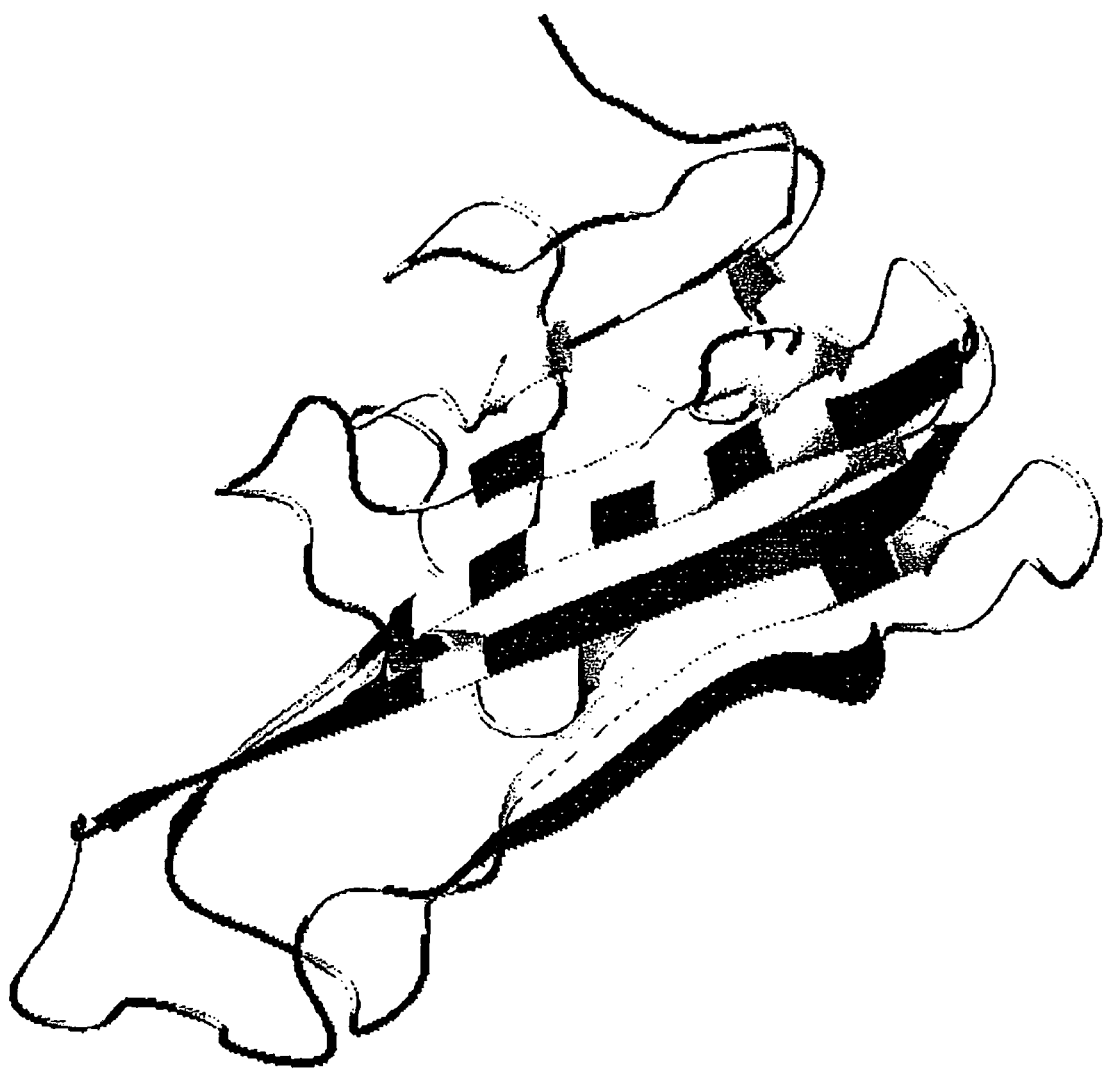
TNFa TRIMER INTERFACE
FIG._5

SEQ ID NO:1

```
1   atgcaccacc accaccacca cgtacgctcc tcctcccgca ctccgtccga caaaccggta
61  gctcacgtag tagctaaccc gcaggctgaa ggtcagctgc agtggctgaa ccgccgcgct
121 aacgctctgc tggctaacgg tgtagaactg cgcgacaacc agctggtagt accgtccgaa
181 ggtctgtacc tgatctactc ccaggtactg ttcaaaggtc agggttgtcc gtccactcac
241 gtactgctga ctcacactat ctcccgcatc gctgtatcct accagactaa agtaaacctg
301 ctgtccgcta tcaaatcccc gtgtcagcgc gaaactccgg aaggtgctga agctaaaccg
361 tggtacgaac cgatctacct gggtggtgta ttccagctgg aaaaaggtga ccgcctgtcc
421 gctgaaatca accgcccgga ctacctggac ttcgctgaat ccggtcaggt atacttcggt
481 atcatcgctc tgtga
```

FIG._6A

SEQ ID NO:2

```
1   MHHHHHHVRS SSRTPSDKPV AHVVANPQAE GQLQWLNRRA NALLANGVEL RDNQLVVPSE

61  GLYLIYSQVL FKGQGCPSTH VLLTHTISRI AVSYQTKVNL LSAIKSPCQR ETPEGAEAKP

121 WYEPIYLGGV FQLEKGDRLS AEINRPDYLD FAESGQVYFG IIAL
```

FIG._6B

| Wild-type TNF amino acid | Wild-type TNF amino acid number | Mutants created |
|---|---|---|
| Q | 21 | R |
| N | 30 | D |
| R | 31 | I, D, E |
| R | 32 | D, E, S |
| A | 33 | E |
| A | 35 | S |
| K | 65 | D, T, M, W, I, Q, S, N, V, E |
| G | 66 | Q, K |
| Q | 67 | D, W, Y, R, K, S |
| A | 111 | R, E |
| K | 112 | D, E |
| Y | 115 | Q, K, E, N, R, F, H, M, L, I, W, D, T, S |
| D | 140 | R, K |
| D | 143 | E, N, Q, S, R, K |
| F | 144 | N |
| A | 145 | R, D, K, N, H, T, Q, E, Y, M, S, F |
| E | 146 | N, K, R, S |
| S | 147 | R |

ALSO MADE DOUBLE MUTANTS K65E/D143K, K65E/D143R, K65D/D143K AND K65D/D143R

FIG._7

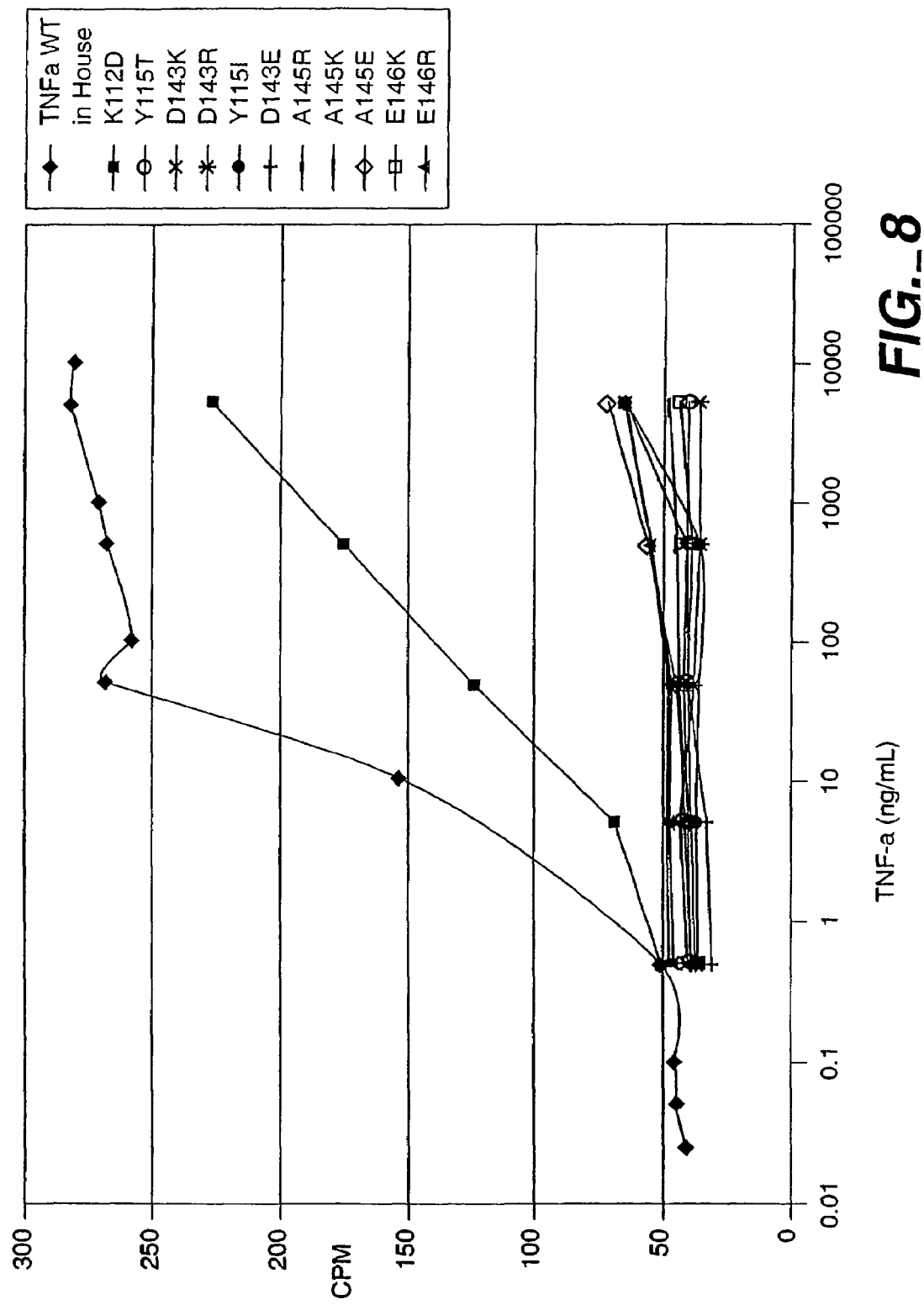
FIG._8

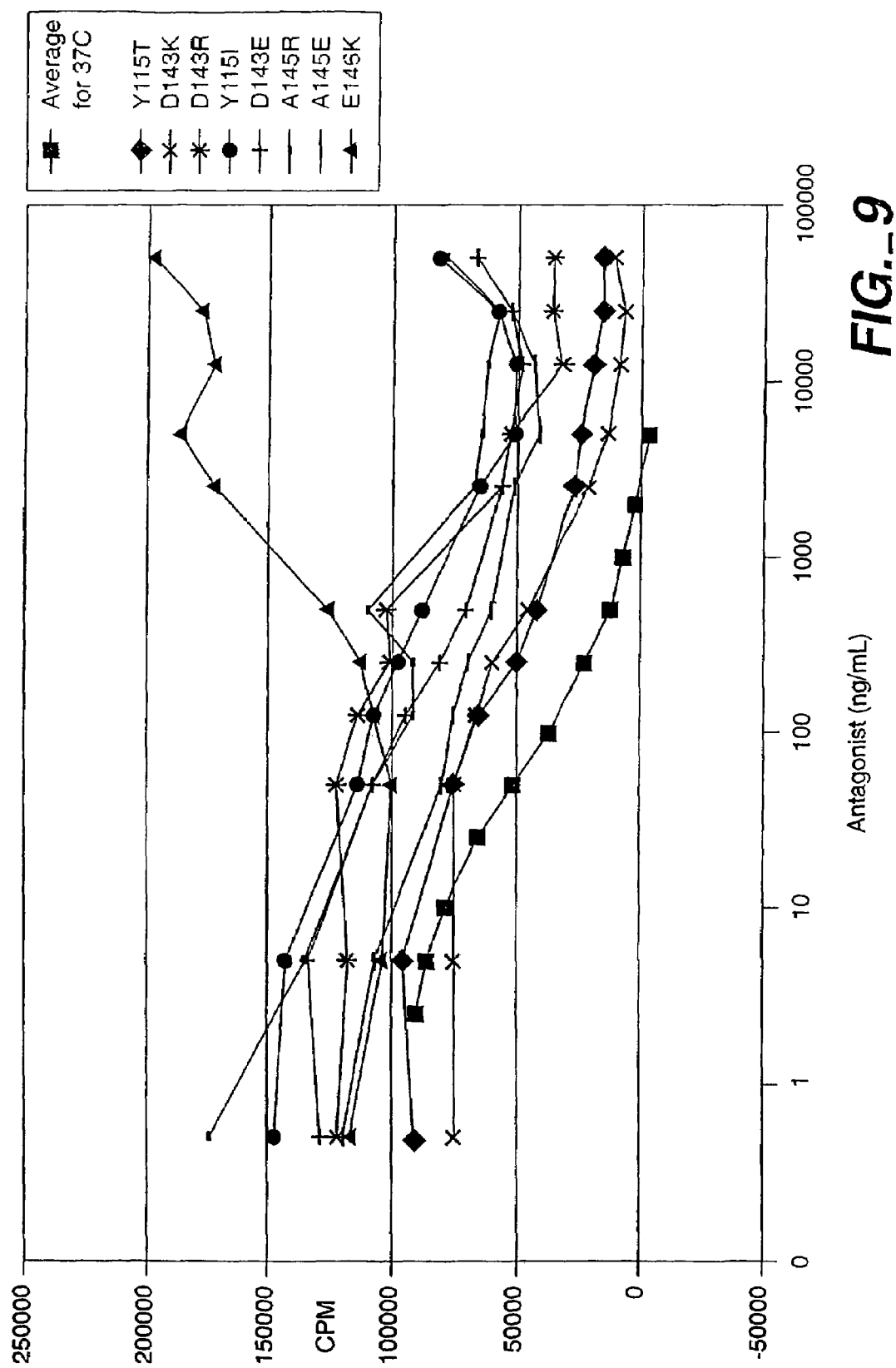
FIG._9

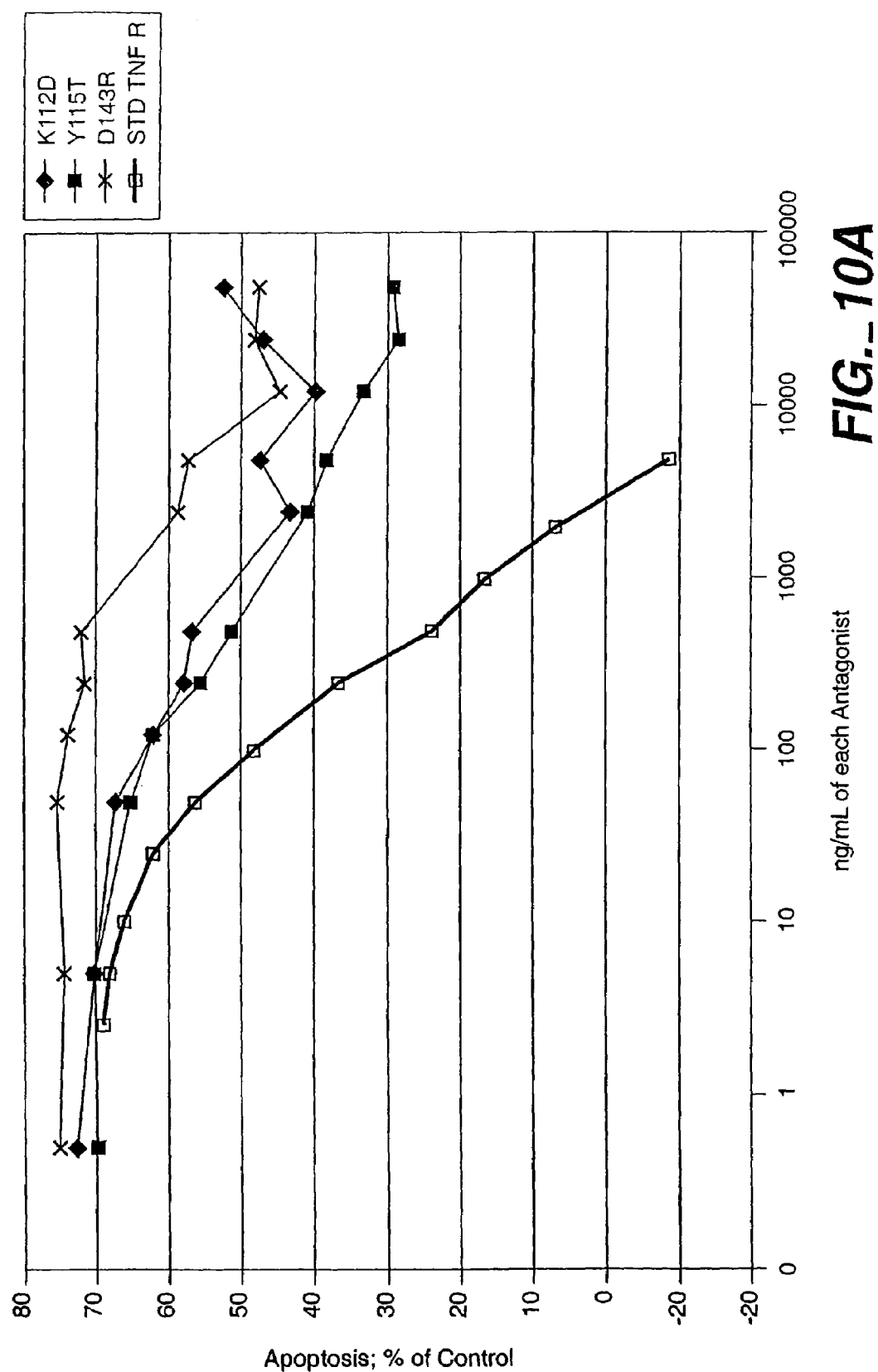
FIG._10A

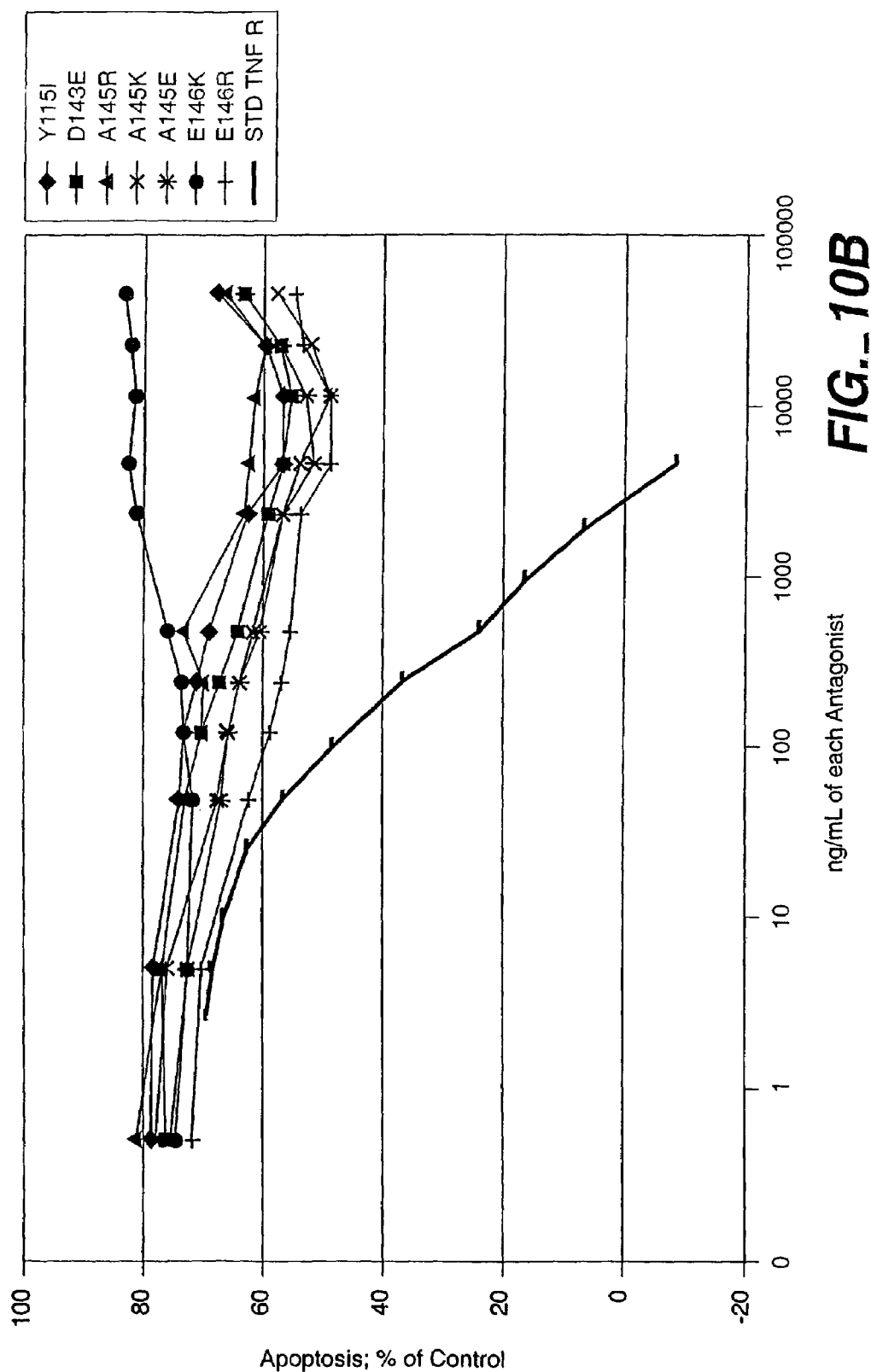
FIG._10B

| WT | PDA Relative Probability Distribution |
|---|---|
| Q21 | R1000 |
| N30 | D1000 |
| R31 | I1000 |
| R32 | H1000 |
| A33 | E1000 |
| A35 | S1000 |
| K65 | R585 D146 K110 T42 H31 M27 W15 I15 Q10 S9 N9 V1 |
| G66 | Q813 K187 |
| Q67 | D623 W209 Y83 R43 K41 S1 |
| A111 | R959 E41 |
| K112 | K1000 |
| Y115 | Q230 K154 E116 N84 Y81 R72 F69 H43 M39 L36 I26 W25 D11 T8 S6 |
| D140 | D1000 |
| L143 | D680 E130 N110 Q33 S29 R12 K6 |
| F144 | F695 N305 |
| A145 | R456 D196 K124 N76 H67 T43 Q25 E9 Y1 M1 S1 F1 |
| E146 | N489 K377 R111 D12 S10 E1 |
| S147 | R1000 |

FIG._11

SEQ ID NO:3

TRAF2(310-) DQDKIEALSSKVQQLERSIGLKDLAMADLEQKVLEMEA STYDG

FIG._12A

SEQ ID NO:4

TRAF3(374-) VARNTGLLESQLSRHDQMLSVHDIRLADMDLRFQVLET ASYNG

FIG._12B

SEQ ID NO:5

TRAF5(343-) NDQRLAVLEEETNKHDTHINIHKAQLSKNEERFKLLEG TCYNG

FIG._12C

SEQ ID NO:6

TRAF1(225-) DRERILSLEQRVVELQQTLAQKDQALGKLEQSLRLMEE ASFDG

FIG._12D

SEQ ID NO:7

TRAF6(309-) QDHQIRELTAKMETQSMYVSELKRTIRTLEDKVAEIEA QQCNG

FIG._12E

SEQ ID NO:8

TRAF4(201-) ---------------CALVSRQRQELQELRRELEELSV GS-DG

FIG._12F

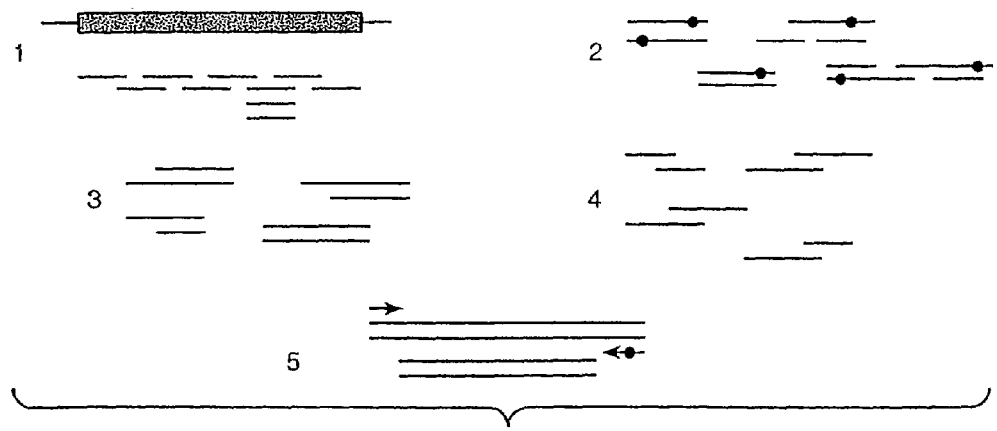

FIG._13

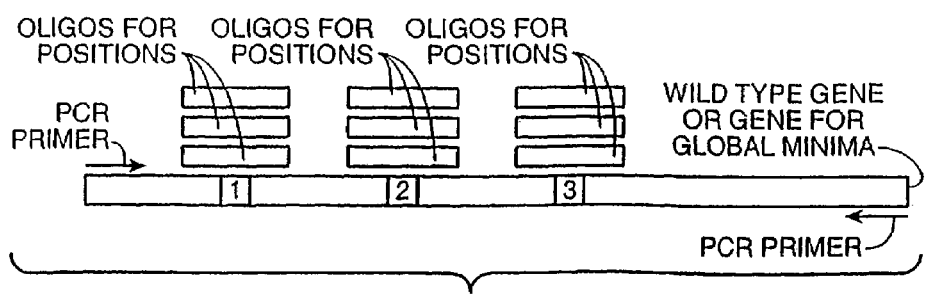

FIG._14

BLACK BOX = REGION TO BE MUTATED
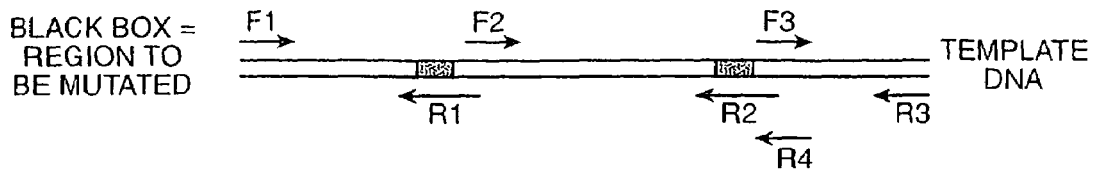
TEMPLATE DNA
STEP 1: SET UP 3 PCR REACTIONS:
PRODUCTS:
TUBE 1:
TUBE 2:
TUBE 3:
STEP 2: SET UP PCR REACTION WITH PRODUCTS OF TUBE 1 + PRODUCTS TUBE 2 + F1 + R4.
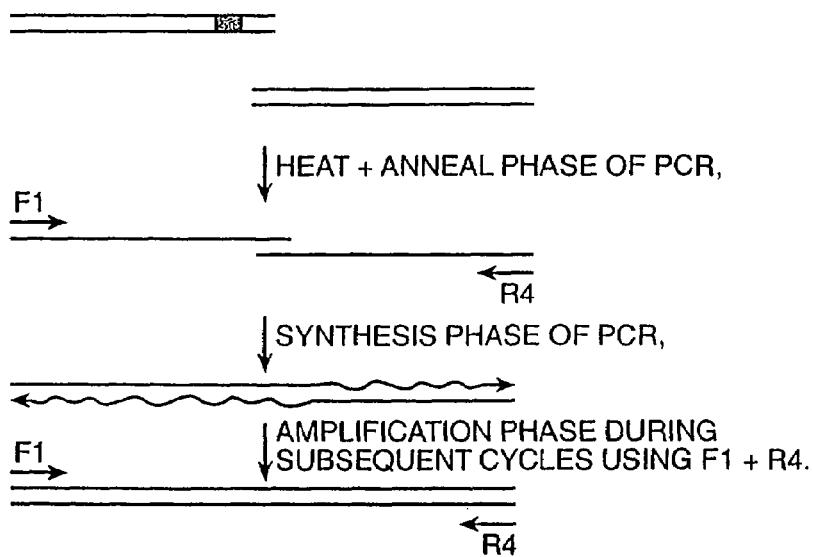
STEP 3: REPEAT STEP 2 USING PRODUCT FROM STEP 2 + PRODUCT FROM STEP 1, TUBE 3 + PRIMERS F1 + R3.
FIG._15

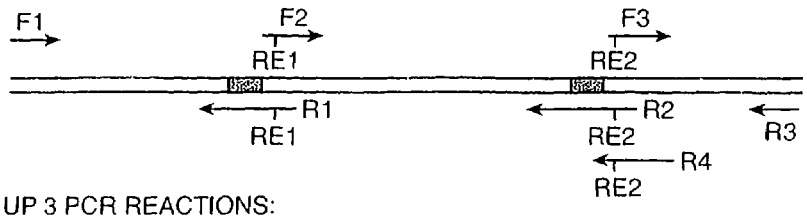

STEP 1: SET UP 3 PCR REACTIONS:

TUBE 1:

TUBE 2:
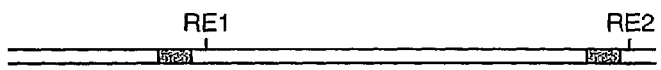

TUBE 3:
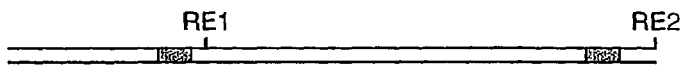

STEP 2: DIGEST PRODUCTS FROM STEP 1 WITH SUITABLE RESTRICTION ENDONUCLEASES.

STEP 3: LIGATE DIGESTED PRODUCT FROM STEP 2, TUBE 2 WITH DIGESTED PRODUCT FROM STEP 2, TUBE 1.

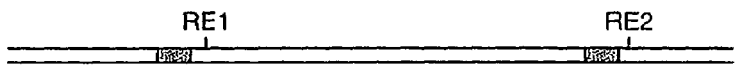

STEP 4: AMPLIFY VIA PCR LIGATED PRODUCTS OF STEP 3 WITH F1 + R4.

STEP 5: DIGEST AMPLIFIED PRODUCT OF STEP 4 WITH RESTRICTION ENDONUCLEASE #2.

STEP 6: LIGATE PRODUCT FROM STEP 5 WITH PRODUCT FROM STEP 2, TUBE 1.

STEP 7: AMPLIFY PRODUCT FROM STEP 6 WITH F1 + R3.

FIG._16

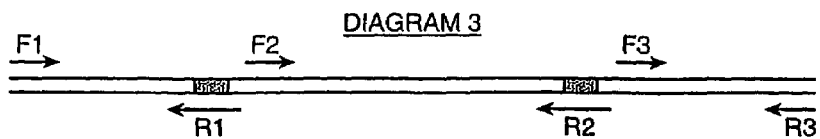

FIG._17

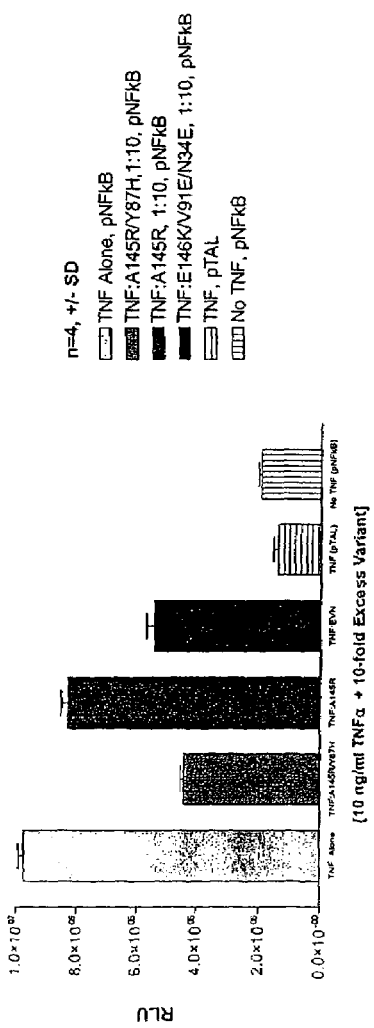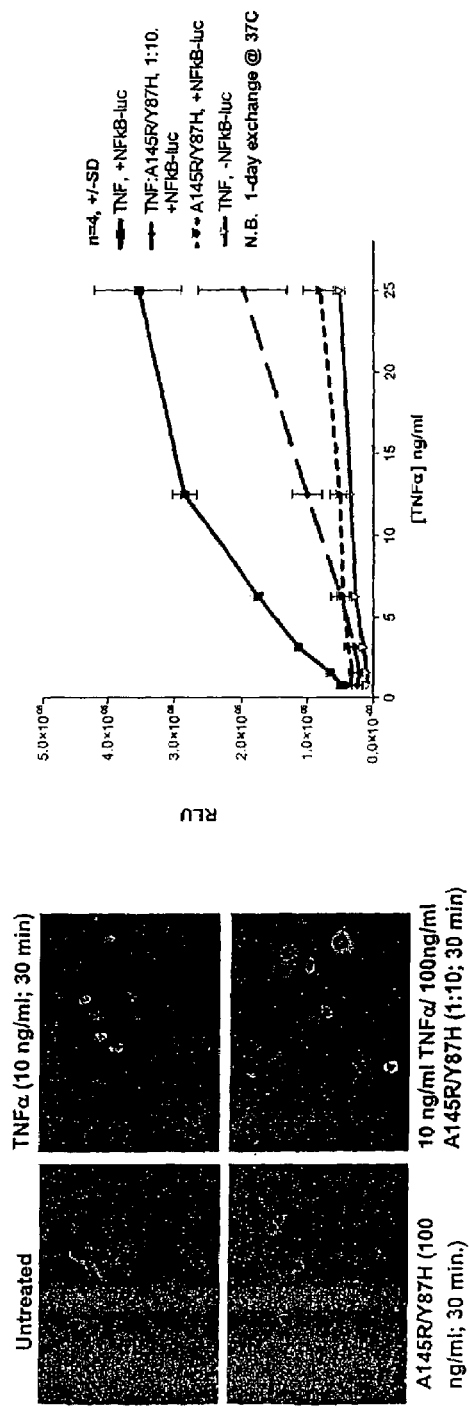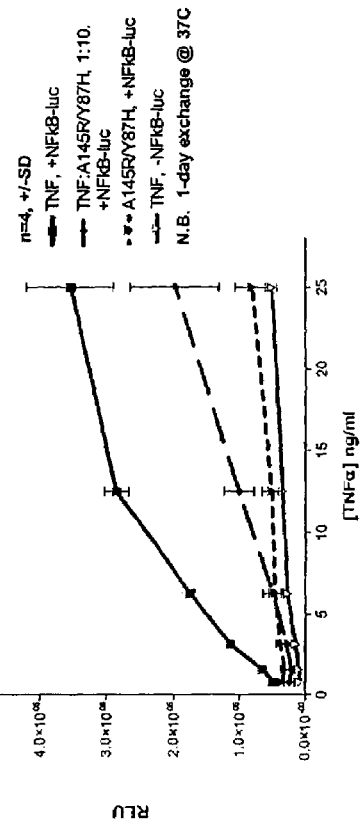
Fig 20A
Fig 20B
Fig 20C

Figures 23 A and B

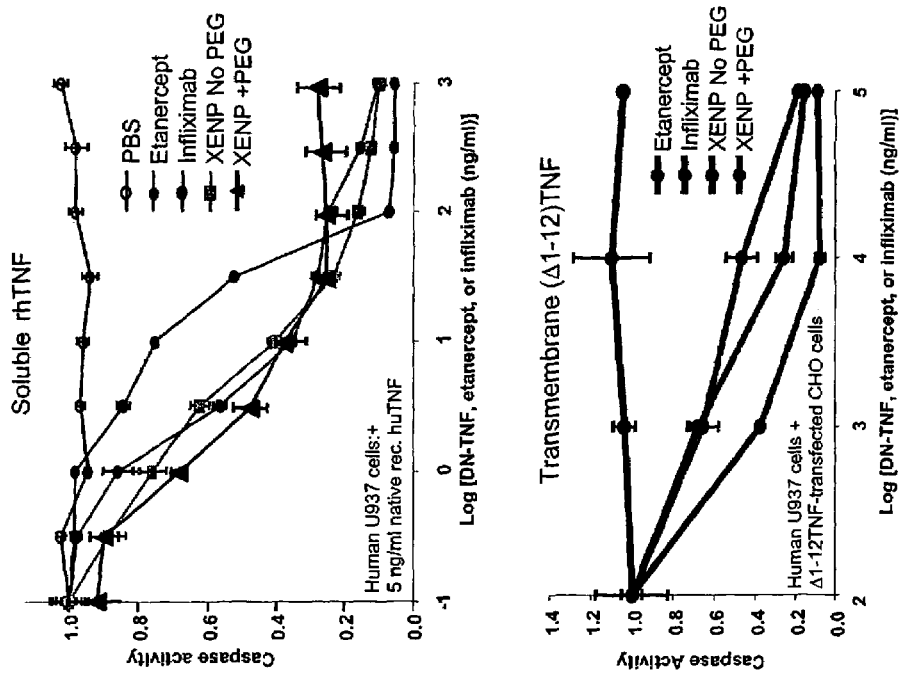
Figure 25

Figure 27

| | | |
|---|---|---|
| Vb 1 | Polymer attachment site | VL |
| Fx2-9 | | |
| Vb10 | Polymer attachment site | DC |
| Fx 11-20 | | |
| Vb21 | Large Domain | QCR |
| Fx22 | | |
| Vb23 | Polymer attachment site | EC |
| Vb 24 | Polymer attachment site | GC |
| site | | |
| Vb25 | Polymer attachment site | QC |
| Fx26 | | |
| Vb27 | Polymer attachment site | QC |
| Fx28-29 | | |
| Vb30 | Large Domain | ND |
| Vb31 | Large Domain | RCIDE |
| Vb32 | Large Domain | RDES |
| Vb33 | Large Domain | AE |
| Vb34 | Trimer Interface | NEV |
| V35 | Large Domain | AS |
| Fx36-41 | | |
| Vb42 | Polymer attachment site | EC |
| Fx43 | | |
| Vb44 | Polymer attachment site | RC |
| Vb45 DC | | |
| Vb46 | Polymer attachment site | NC |
| Fx47-56 | | |
| Vb57 | Trimer Interface | LFWY |
| F 58-64 | | |
| Vx65 | Large Domain | KDEIMNQTSVW |
| Vb66 | Large Domain | GKQ |
| Vb67 | Large Domain | QDKRSWY |
| Fx68 | | |
| Vb 69 | | CV |
| Fx 70-75 | | |
| Vb75 | Small Domain | LEKQ |
| Fx76-83 | | |
| Vb84 | DE Loop | AV |

Figure 27 (continued)

| | | |
|---|---|---|
| Fx85 | | |
| Vb86 | DE Loop | SQR |
| Vb87 | DE Loop | YHR |
| Vb88 | Polymer attachment site | QC |
| Fx89 | | |
| Vb90 | Polymer attachment site | KC |
| Vb91 | DE Loop, Trimer Interface | VE |
| Fx92-96 | | |
| Vb97 | Small Domain | IRT |
| Fx 98-100 | | |
| Vb101 | | CA |
| Fx102-106 | | |
| Vb107 | Polymer attachment site | IC |
| Vb108 | Polymer attachment site | GC |
| Fx109 | | |
| Vb110 | Polymer attachment site | EC |
| Vb111 | Large Domain | ARE |
| Vb112 | Large Domain | KDE |
| Fx113-114 | | |
| Vb115 | Large Domain | YDEFHIKLMNQRSTW |
| Fx1'16-127 | | |
| Vb128 | Polymer attachment site | KC |
| Fx129-139 | | |
| Vb140 | Large Domain | DKR |
| Fx141-142 | | |
| Vb143 | Large Domain | DEKLRNQRS |
| Vb144 | Large Domain | FN |
| Vb145 | Large Domain | ADEFHKMNQRSTY |
| Vb146 | Large Domain | EKLMNRS |
| Vb147 | Large Domain | SR |

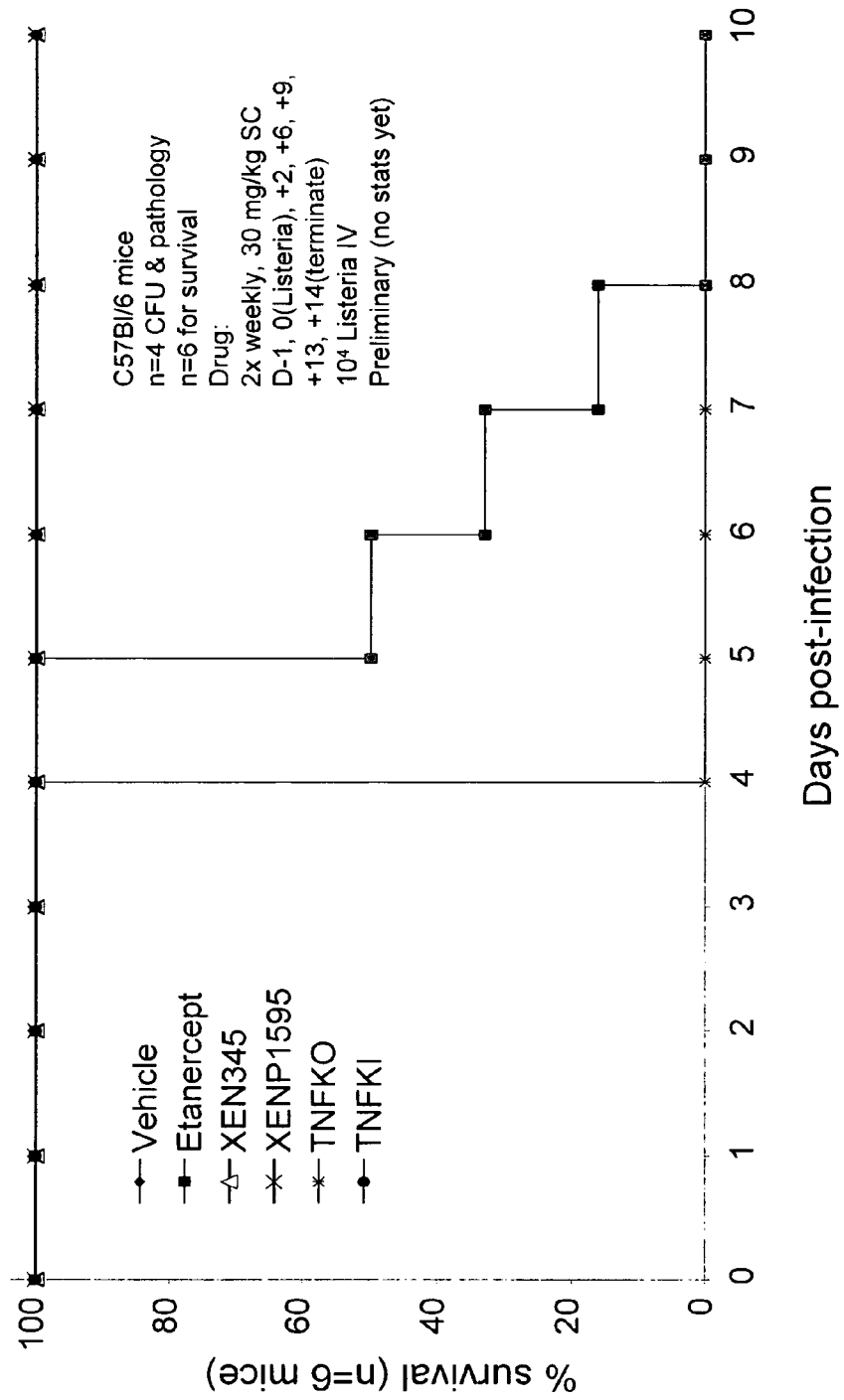

Figure 31 - Improving pharmacokinetics: Rational pegylation of DN-TNF

TNF and DN-TNF variants have short in vivo half-life

Therefore, engineer new PEG site (via new surface cysteine):

- To maintain ligand monomer, homotrimer, & heterotrimer structures
- To further disrupt receptor interfaces

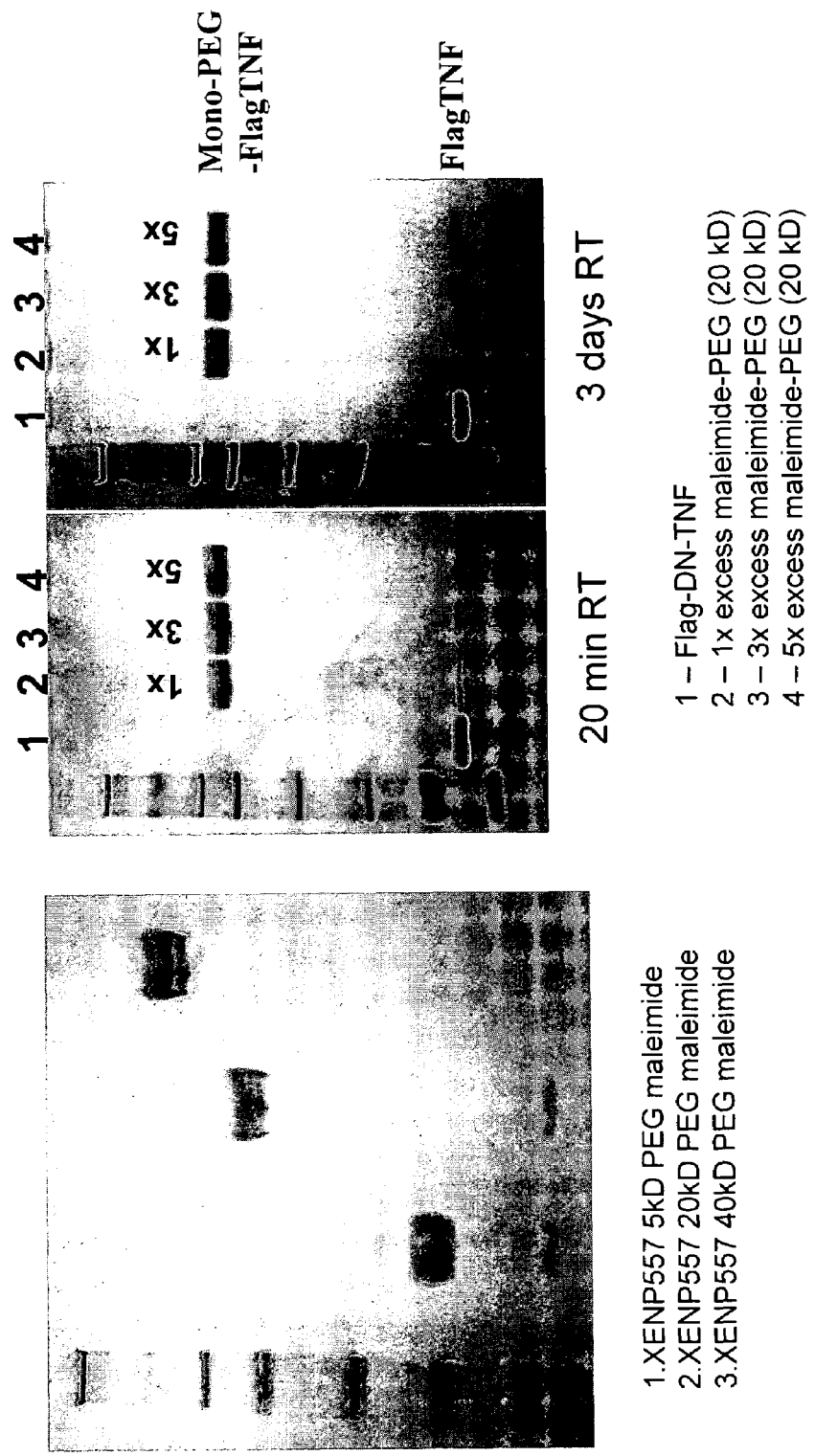
Figure 32 - PEG-maleimide reaction with engineered XENP557 is homogeneous pegylated product

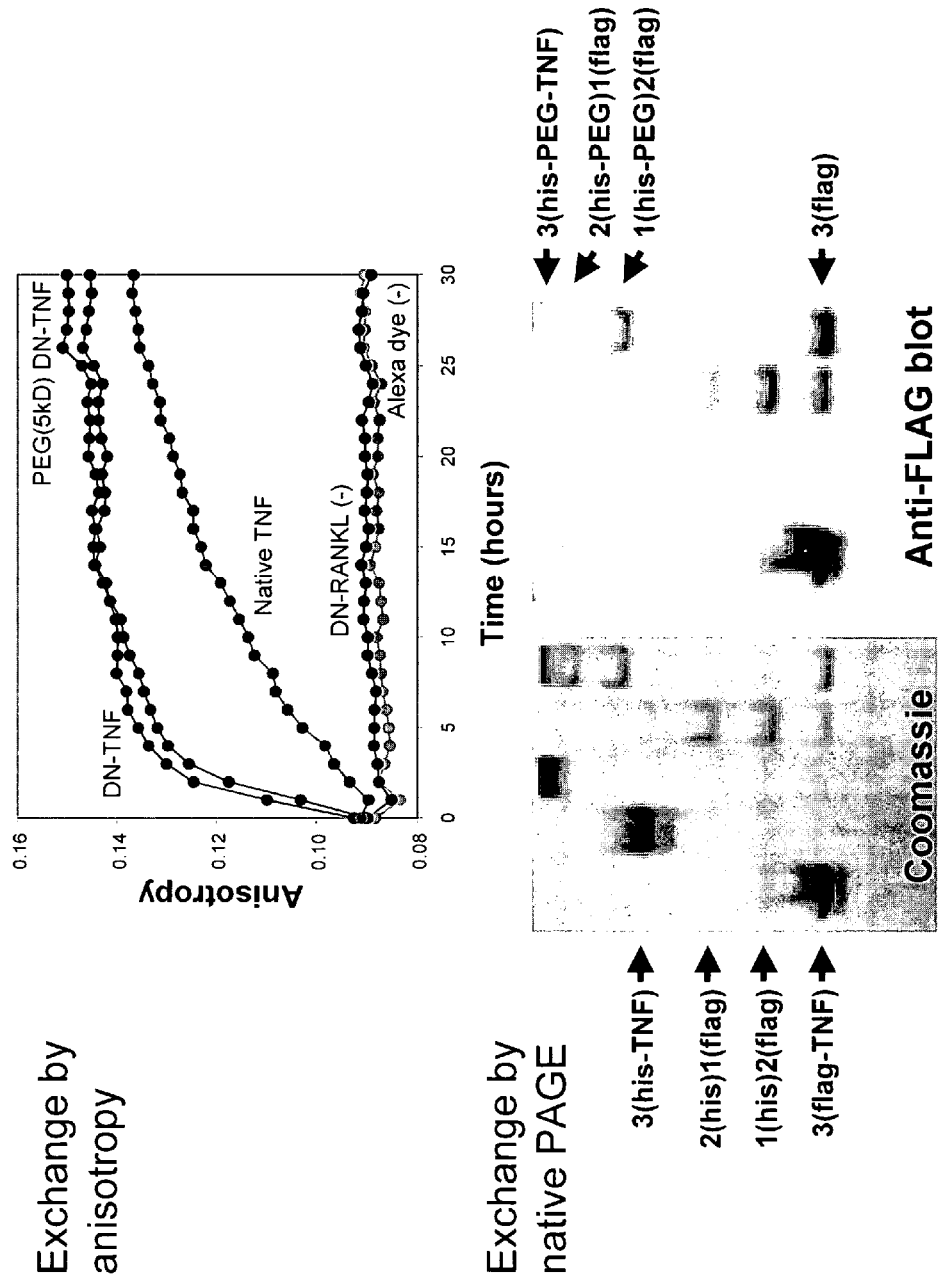
Figure 33 - PEG does not interfere with DN-TNF exchange into native TNF

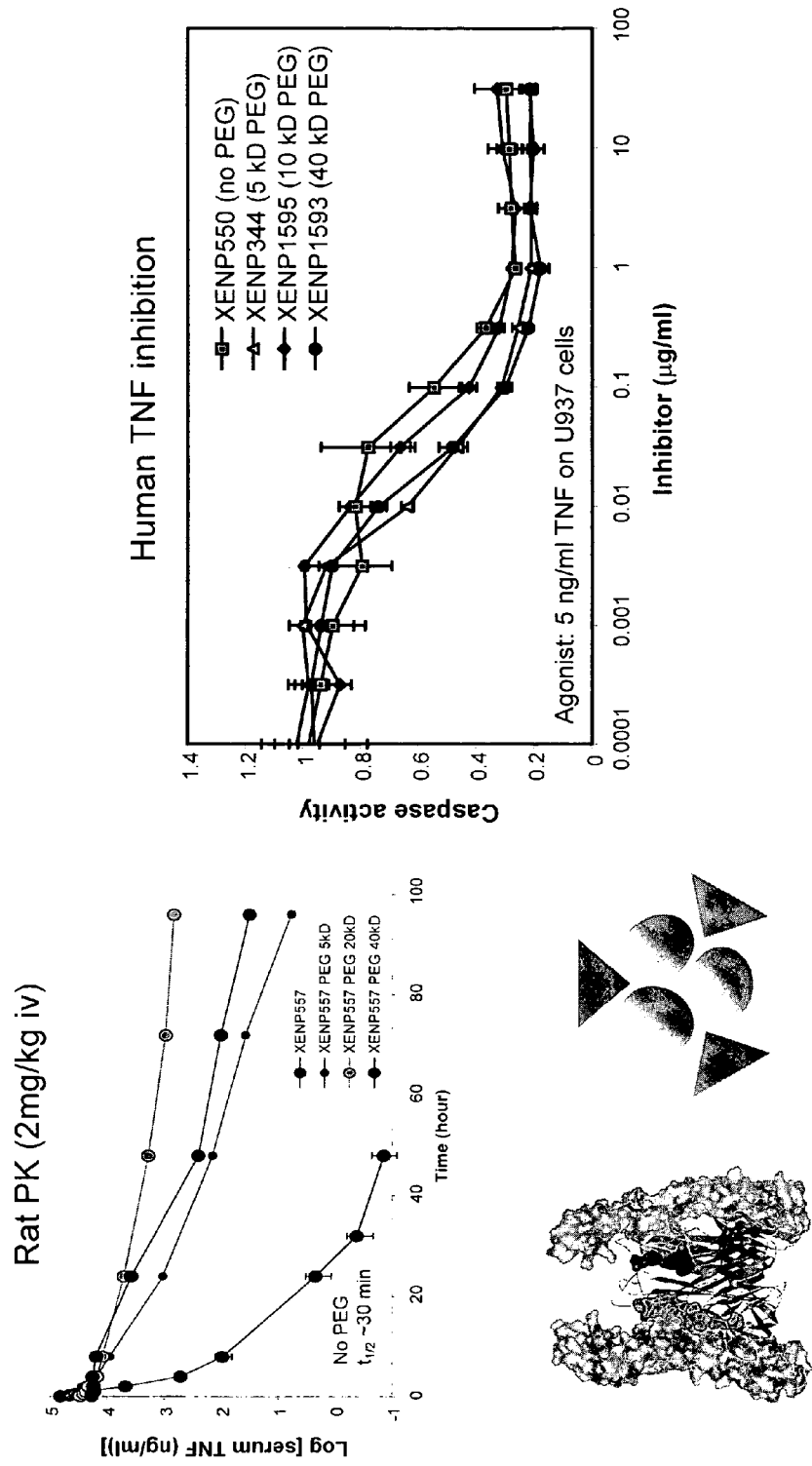
Figure 34 - Rational site-directed pegylation improves PK without compromising activity

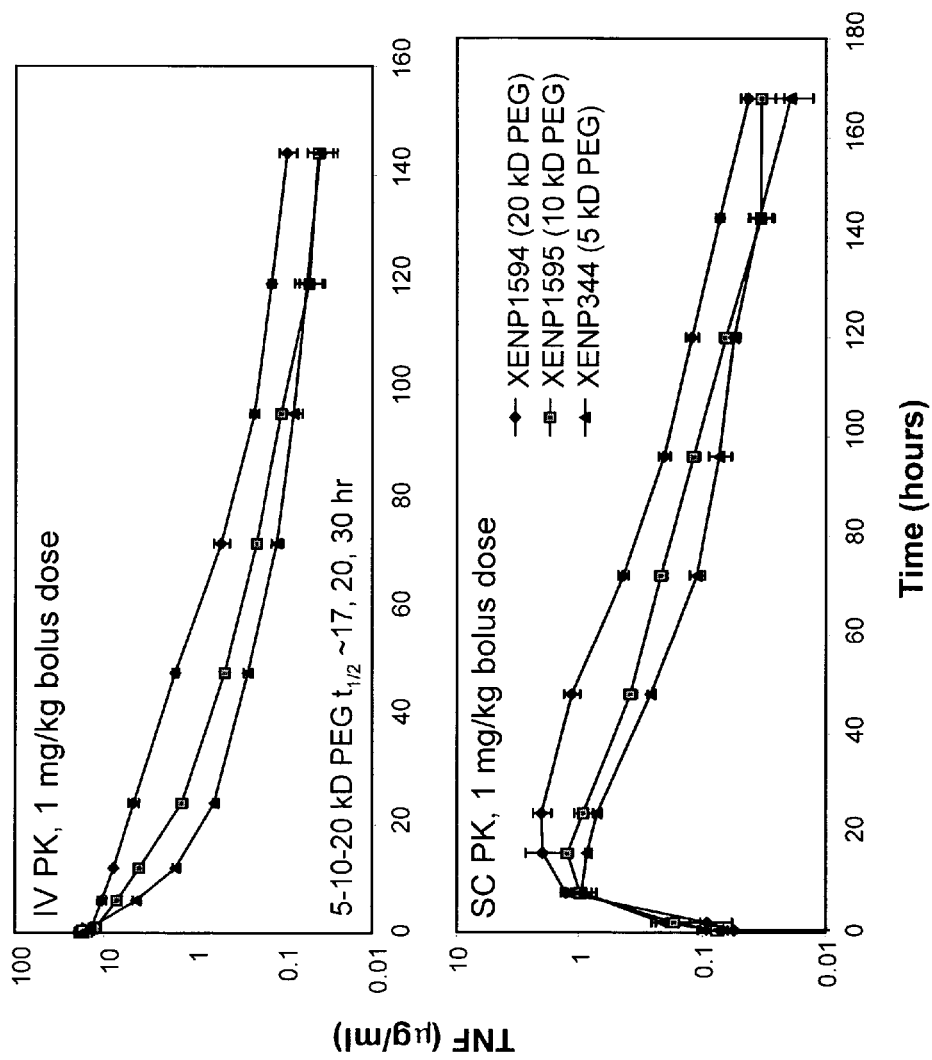
Figure 35 - PK of pegylated [$I^{125}$] DN-TNFs: IV & SC

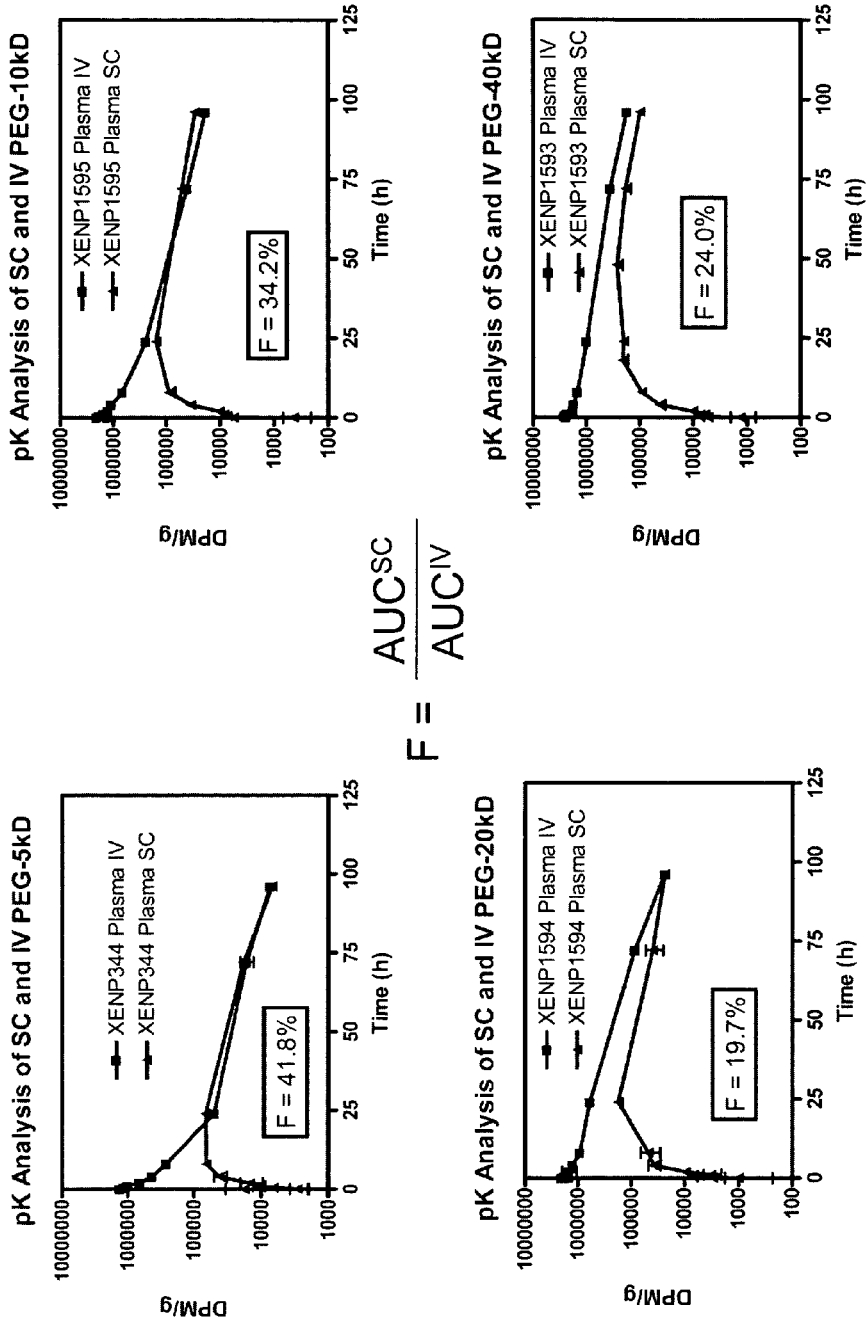
Figure 36 - SC bioavailability in rats of pegylated DN-TNFs

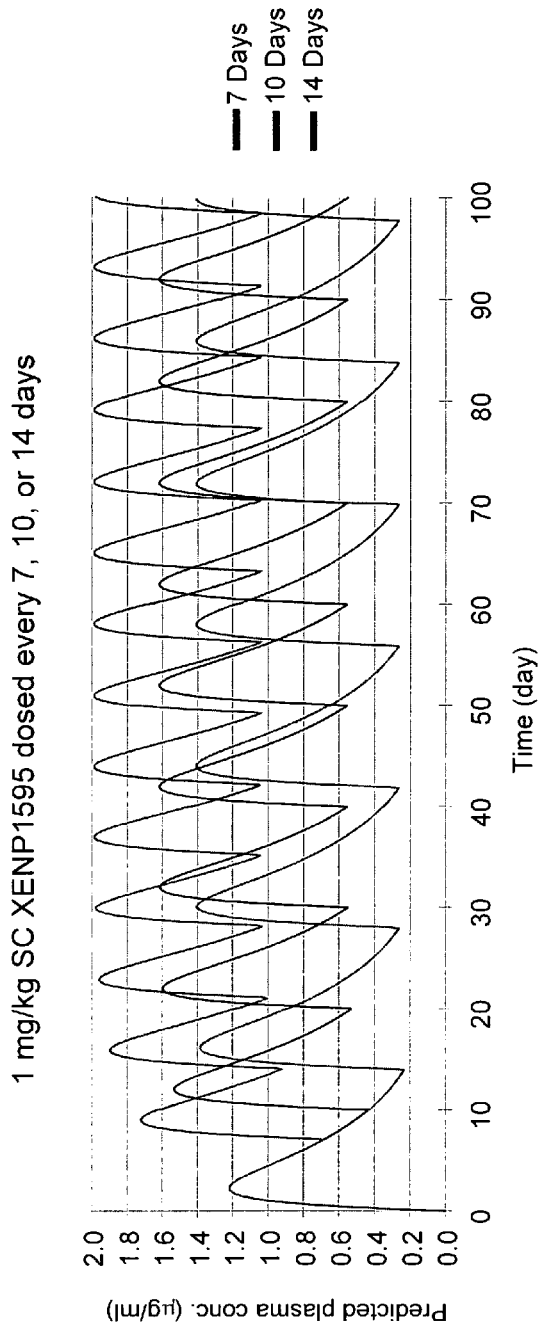

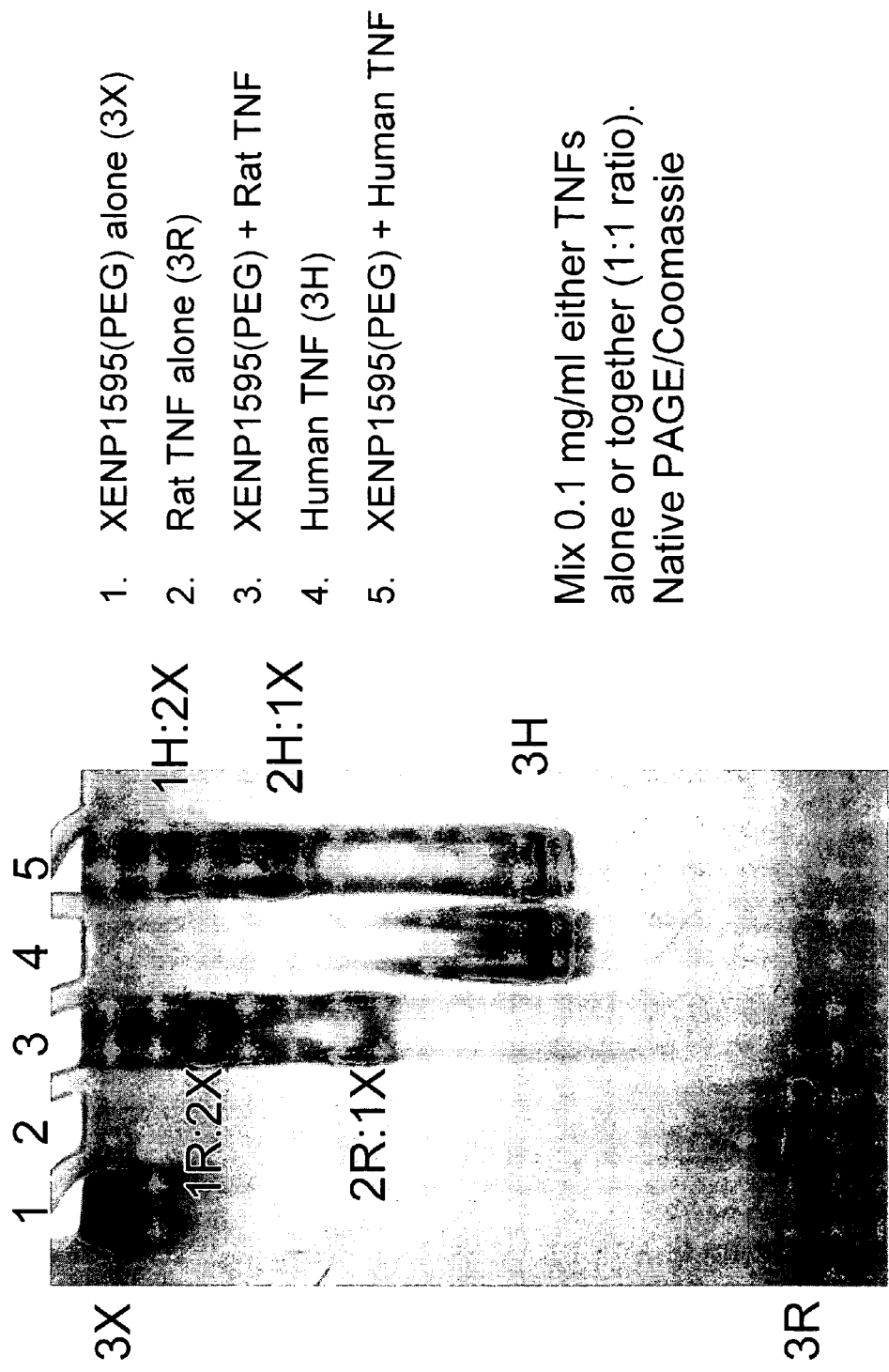
Figure 38 - DN-TNFs also exchange with murine TNF

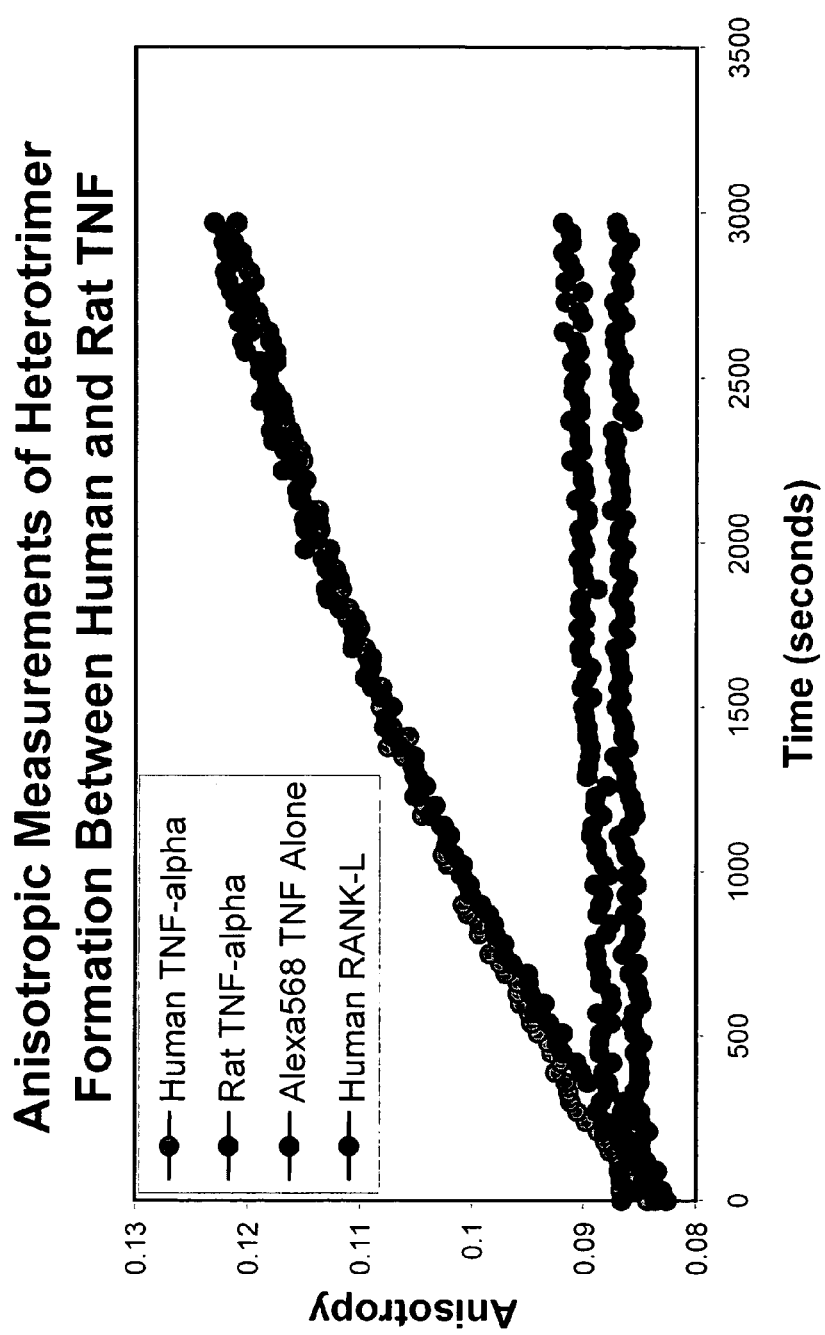
Figure 39 - Murine TNF exchanges with human TNF just as rapidly as human with itself

US 7,446,174 B2

SEQUENCE LISTING

```
<160> NUMBER OF SEQ ID NOS: 13

<210> SEQ ID NO 1
<211> LENGTH: 495
<212> TYPE: DNA
<213> ORGANISM: Homo sapiens

<400> SEQUENCE: 1
atgcaccacc accaccacca cgtacgctcc tcctcccgca ctccgtccga caaaccggta      60
gctcacgtag tagctaaccc gcaggctgaa ggtcagctgc agtggctgaa ccgccgcgct     120
aacgctctgc tggctaacgg tgtagaactg cgcgacaacc agctggtagt accgtccgaa     180
ggtctgtacc tgatctactc ccaggtactg ttcaaaggtc agggttgtcc gtccactcac     240
gtactgctga ctcacactat ctcccgcatc gctgtatcct accagactaa agtaaacctg     300
ctgtccgcta tcaaatcccc gtgtcagcgc gaaactccgg aaggtgctga agctaaaccg     360
tggtacgaac cgatctacct gggtggtgta ttccagctgg aaaaaggtga ccgcctgtcc     420
gctgaaatca accgcccgga ctacctggac ttcgctgaat ccggtcaggt atacttcggt     480
atcatcgctc tgtga                                                      495

<210> SEQ ID NO 2
<211> LENGTH: 164
```

```
<212> TYPE: PRT
<213> ORGANISM: Homo sapiens

<400> SEQUENCE: 2

Met His His His His His Val Arg Ser Ser Ser Arg Thr Pro Ser
1               5                   10                  15

Asp Lys Pro Val Ala His Val Val Ala Asn Pro Gln Ala Glu Gly Gln
            20                  25                  30

Leu Gln Trp Leu Asn Arg Arg Ala Asn Ala Leu Leu Ala Asn Gly Val
        35                  40                  45

Glu Leu Arg Asp Asn Gln Leu Val Pro Ser Glu Gly Leu Tyr Leu
    50                  55                  60

Ile Tyr Ser Gln Val Leu Phe Lys Gly Gln Gly Cys Pro Ser Thr His
65                  70                  75                  80

Val Leu Leu Thr His Thr Ile Ser Arg Ile Ala Val Ser Tyr Gln Thr
                85                  90                  95

Lys Val Asn Leu Leu Ser Ala Ile Lys Ser Pro Cys Gln Arg Glu Thr
            100                 105                 110

Pro Glu Gly Ala Glu Ala Lys Pro Trp Tyr Glu Pro Ile Tyr Leu Gly
        115                 120                 125

Gly Val Phe Gln Leu Glu Lys Gly Asp Arg Leu Ser Ala Glu Ile Asn
    130                 135                 140

Arg Pro Asp Tyr Leu Asp Phe Ala Glu Ser Gly Gln Val Tyr Phe Gly
145                 150                 155                 160

Ile Ile Ala Leu

<210> SEQ ID NO 3
<211> LENGTH: 43
<212> TYPE: PRT
<213> ORGANISM: Artificial
<220> FEATURE:
<223> OTHER INFORMATION: synthetic

<400> SEQUENCE: 3

Asp Gln Asp Lys Ile Glu Ala Leu Ser Ser Lys Val Gln Gln Leu Glu
1               5                   10                  15

Arg Ser Ile Gly Leu Lys Asp Leu Ala Met Ala Asp Leu Glu Gln Lys
            20                  25                  30

Val Leu Glu Met Glu Ala Ser Thr Tyr Asp Gly
        35                  40

<210> SEQ ID NO 4
<211> LENGTH: 43
<212> TYPE: PRT
<213> ORGANISM: Artificial
<220> FEATURE:
<223> OTHER INFORMATION: synthetic

<400> SEQUENCE: 4

Val Ala Arg Asn Thr Gly Leu Leu Glu Ser Gln Leu Ser Arg His Asp
1               5                   10                  15

Gln Met Leu Ser Val His Asp Ile Arg Leu Ala Asp Met Asp Leu Arg
            20                  25                  30

Phe Gln Val Leu Glu Thr Ala Ser Tyr Asn Gly
        35                  40

<210> SEQ ID NO 5
<211> LENGTH: 43
<212> TYPE: PRT
```

```
<213> ORGANISM: Artificial
<220> FEATURE:
<223> OTHER INFORMATION: synthetic

<400> SEQUENCE: 5

Asn Asp Gln Arg Leu Ala Val Leu Glu Glu Thr Asn Lys His Asp
1               5                   10                  15

Thr His Ile Asn Ile His Lys Ala Gln Leu Ser Lys Asn Glu Glu Arg
            20                  25                  30

Phe Lys Leu Leu Glu Gly Thr Cys Tyr Asn Gly
        35                  40

<210> SEQ ID NO 6
<211> LENGTH: 43
<212> TYPE: PRT
<213> ORGANISM: Artificial
<220> FEATURE:
<223> OTHER INFORMATION: synthetic

<400> SEQUENCE: 6

Asp Arg Glu Arg Ile Leu Ser Leu Glu Gln Arg Val Val Glu Leu Gln
1               5                   10                  15

Gln Thr Leu Ala Gln Lys Asp Gln Ala Leu Gly Lys Leu Glu Gln Ser
            20                  25                  30

Leu Arg Leu Met Glu Glu Ala Ser Phe Asp Gly
        35                  40

<210> SEQ ID NO 7
<211> LENGTH: 43
<212> TYPE: PRT
<213> ORGANISM: Artificial
<220> FEATURE:
<223> OTHER INFORMATION: synthetic

<400> SEQUENCE: 7

Gln Asp His Gln Ile Arg Glu Leu Thr Ala Lys Met Glu Thr Gln Ser
1               5                   10                  15

Met Tyr Val Ser Glu Leu Lys Arg Thr Ile Arg Thr Leu Glu Asp Lys
            20                  25                  30

Val Ala Glu Ile Glu Ala Gln Gln Cys Asn Gly
        35                  40

<210> SEQ ID NO 8
<211> LENGTH: 27
<212> TYPE: PRT
<213> ORGANISM: Artificial
<220> FEATURE:
<223> OTHER INFORMATION: synthetic

<400> SEQUENCE: 8

Cys Ala Leu Val Ser Arg Gln Arg Gln Glu Leu Gln Glu Leu Arg Arg
1               5                   10                  15

Glu Leu Glu Glu Leu Ser Val Gly Ser Asp Gly
            20                  25

<210> SEQ ID NO 9
<211> LENGTH: 5
<212> TYPE: PRT
<213> ORGANISM: Artificial
<220> FEATURE:
<223> OTHER INFORMATION: synthetic

<400> SEQUENCE: 9
```

```
Gly Ser Gly Gly Ser
1               5

<210> SEQ ID NO 10
<211> LENGTH: 5
<212> TYPE: PRT
<213> ORGANISM: Artificial
<220> FEATURE:
<223> OTHER INFORMATION: synthetic

<400> SEQUENCE: 10

Gly Gly Gly Gly Ser
1               5

<210> SEQ ID NO 11
<211> LENGTH: 4
<212> TYPE: PRT
<213> ORGANISM: Artificial
<220> FEATURE:
<223> OTHER INFORMATION: synthetic

<400> SEQUENCE: 11

Gly Gly Gly Ser
1

<210> SEQ ID NO 12
<211> LENGTH: 157
<212> TYPE: PRT
<213> ORGANISM: Homo sapiens

<400> SEQUENCE: 12

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
130                 135                 140

Ala Glu Ser Gly Gln Val Tyr Phe Gly Ile Ile Ala Leu
145                 150                 155

<210> SEQ ID NO 13
<211> LENGTH: 7
<212> TYPE: PRT
<213> ORGANISM: Artificial
```

```
<220> FEATURE:
<223> OTHER INFORMATION: synthetic

<400> SEQUENCE: 13

Met His His His His His His
1               5
```

PROTEIN BASED TNF-α VARIANTS FOR THE TREATMENT OF TNF-α RELATED DISORDERS

This application is a continuation-in-part of U.S. application Ser. No. 10/963,994, filed Oct. 12, 2004; Ser. No. 09/798, 789, filed Mar. 2, 2001, now U.S. Pat. No. 7,056,695; Ser. No. 09/945,150, filed Aug. 31, 2001, now abandoned; Ser. No. 09/981,289, filed Oct. 15, 2001, now U.S. Pat. No. 7,101,974; Ser. No. 10/262,630, filed Sep. 30, 2002, now U.S. Pat. No. 7,244,823 and claims benefit under 35 U.S.C. 119(e) to U.S. Application Ser. Nos. 60/553,908, filed Mar. 17, 2004; 60/509,960, filed Oct. 9, 2003; 60/528,275, filed Dec. 8, 2003; 60/523,647, filed Nov. 20, 2003; and 60/186,427, filed Mar. 2, 2000, all of which are expressly incorporated by reference in their entirety.

FIELD OF THE INVENTION

The invention relates to novel proteins with TNF-α antagonist activity and nucleic acids encoding these proteins. The invention further relates to the use of the novel proteins in the treatment of TNF-α related disorders. In addition, the invention relates to proteins with TNF-α activity that possess receptor specificity as well as a reduced side effect profile with novel soluble ligand selective inhibition. Furthermore, the invention relates to methods of using molecules, including variant TNF-α monomers, to selectively inhibit the activity of soluble TNF-α relative to the activity of transmembrane TNF-α.

BACKGROUND OF THE INVENTION

Tumor necrosis factor α (TNF-α or TNF-alpha) is a pleiotropic cytokine that is primarily produced by activated macrophages and lymphocytes; but is also expressed in endothelial cells and other cell types. TNF-α is a major mediator of inflammatory, immunological, and pathophysiological reactions. (Grell, M., et al., (1995) Cell, 83:793-802), incorporated by reference. Two distinct forms of TNF exist, a 26 kDa membrane expressed form and the soluble 17 kDa cytokine which is derived from proteolytic cleavage of the 26 kDa form. The soluble TNF polypeptide is 157 amino acids long and is the primary biologically active molecule.

TNF-α exerts its biological effects through interaction with high-affinity cell surface receptors. Two distinct membrane TNF-α receptors have been cloned and characterized. These are a 55 kDa species, designated p55 TNF-R and a 75 kDa species designated p75 TNF-R (Corcoran. A. E., et al., (1994) Eur. J. Biochem., 223:831-840), incorporated by reference. The two TNF receptors exhibit 28% similarity at the amino acid level. This is confined to the extracellular domain and consists of four repeating cysteine-rich motifs, each of approximately 40 amino acids. Each motif contains four to six cysteines in conserved positions. Dayhoff analysis shows the greatest intersubunit similarity among the first three repeats in each receptor. This characteristic structure is shared with a number of other receptors and cell surface molecules, which comprise the TNF-R/nerve growth factor receptor superfamily. TNF signaling is initiated by receptor clustering, either by the trivalent ligand TNF or by cross-linking monoclonal antibodies (Vandevoorde, V., et al., (1997) J. Cell Biol., 137:1627-1638), incorporated by reference.

Crystallographic studies of TNF and the structurally related cytokine, lymphotoxin (LT) have shown that both cytokines exist as homotrimers, with subunits packed edge to edge in a threefold symmetry. Structurally, neither TNF or LT reflect the repeating pattern of the their receptors. Each monomer is cone shaped and contains two hydrophilic loops on opposite sides of the base of the cone. Recent crystal structure determination of a p55 soluble TNF-R/LT complex has confirmed the hypothesis that loops from adjacent monomers join together to form a groove between monomers and that TNF-R binds in these grooves. Random mutagenesis has been used to identify active sites in TNF-α responsible for the loss of cytotoxic activity (Van Ostade, X., et al., (1991) EMBO J., 10:827-836), incorporated by reference. Human TNF muteins having higher binding affinity for human p75-TNF receptor than for human p55-TNF receptor have also been disclosed (U.S. Pat. No. 5,597,899 and Loetscher et al., J. Biol. Chem., 268(35) pp 263050-26357 (1993)), incorporated by reference.

The different activities of soluble TNF (solTNF) and transmembrane TNG (tmTNF), mediated through discrete interactions with receptors TNFR1 and TNFR2, may account for contrasting beneficial and harmful roles reported for TNF in animal models and in human disease (Kollias, D. Kontoyiannis, Cytokine Growth Factor Rev. 13, 315 (2002); M. Grell et al., Cell 83, 793 (1995); M. Grell, H. Wajant, G. Zimmermann, P. Scheurich, Proc. Natl. Acad. Sci. U.S.A. 95, 570 (1998); C. O. Jacob, Immunol. Today 13, 122 (1992); R. N. Saha, K. Pahan, J. Neurochem. 86, 1057 (2003); and, M. H. Holtmann, M. F. Neurath, Curr. Mol. Med. 4, 439 (2004), all incorporated by reference). For example, paracrine signaling by solTNF is associated with chronic inflammation, while juxtacrine signaling by tmTNF plays an essential role in resolving inflammation and maintaining immunity to pathogens (Holtmann & Neurath, supra; S. R. Ruuls et al., Immunity 15, 533 (2001); M. Canault et al., Atherosclerosis 172, 211 (2004); C. Mueller et al., J. Biol. Chem. 274, 38112 (1999); M. L. Olleros et al., J. Immunol. 168, 3394 (2002); and, M. Pasparakis, L. Alexopoulou, V. Episkopou, G. Kollias, J. Exp. Med. 184, 1397 (1996), all incorporated by reference.) Excess soluble TNF levels are associated with numerous inflammatory and autoimmune diseases, and inactivation of TNF by injectable protein inhibitors reduces symptoms and blocks disease progression (B. B. Aggarwal, A. Samanta, M. Feldmann, in Cytokine Reference J. J. Oppenheim, M. Feldmann, Eds. (Academic Press, London, 2000) pp. 413-434, incorporated by reference). The three FDA-approved TNF inhibitors include a TNFR2-IgG1 Fc decoy receptor (etanercept) and two neutralizing monoclonal antibodies, Remicade® (infliximab) and Humira® (adalimumab). Although effective anti-inflammatory agents, these immunosuppressive drugs can exacerbate demyelinating disease, induce lymphoma, reactivate latent tuberculosis, and increase the risk of sepsis and other infections (as indicated in their warning labels) (N. Scheinfeld, J. Dermatolog. Treat. 15, 280 (2004), incorporated by reference.) A possible explanation for the increased risk of infection comes from studies using TNF knockout and tmTNF knock-in mice, which demonstrate that tmTNF signaling is sufficient to maintain immunity to listerial and mycobacterial infection. In contrast, solTNF is a primary driver of inflammation. Decoy receptors and antibodies can bind to tmTNF, and that etanercept, infliximab, and adalimumab inhibit tmTNF in addition to solTNF (J. Gerspach et al., Microsc. Res. Tech. 50, 243 (2000); H. Mitoma, T. Horiuchi, H. Tsukamoto, Gastroenterology 126, 934 (2004); J. Agnholt, J. F. Dahlerup, K. Kaltoft, Cytokine 23, 76 (2003); B. Scallon et al., J. Pharmacol. Exp. Ther. 301, 418 (2002); C. Shen et al., Aliment. Pharmacol. Ther. 21, 251 (2005); and, H. Mitoma et al., Gastroenterology 128, 376 (2005), all incorporated by reference.) In view of the serious side effects of existing therapies, a therapeutic that is more potent and has a reduced side effect profile is still needed. The present invention shows that an anti-inflammatory agent that inhibits solTNF but spares tmTNF-mediated signaling will block inflammation yet preserve normal immunity to infectious agents.

SUMMARY OF THE INVENTION

In accordance with the objects outlined above, the present invention provides non-naturally occurring variant TNF-α proteins (e.g. proteins not found in nature) comprising amino acid sequences with at least one amino acid change compared to the wild type TNF-α proteins.

In one aspect, the invention provides methods of selectively inhibiting the activity of wild-type soluble TNF-α in humans by administering a molecule that inhibits the activity of the soluble TNF-α while substantially maintaining the activity of transmembrane TNF-α. As noted below, some aspects of the invention include variants that will inhibit the transmembrane TNF-α activity as well. In another aspect, the molecule is a variant TNF-α as compared to human wild-type TNF-α (SEQ ID NO:.1). Optionally, but preferably, the TNF-α variant is substantially free of agonistic activity.

In some aspects, the TNF-α variant comprises the amino acid substitution Y87H, usually accompanied by an additional mutation, including A145R. Similarly, in some aspects, the TNF-α variant comprises the amino acid substitution I97T, usually accompanied by an additional mutation, including A145R.

Optionally, the variant TNF-α can have amino acid modifications to modulate the addition of polymer groups, such as polyethylene glycol (PEG), including the alteration of cysteine groups at positions 69 and 101 to residues that will not participate in a PEGylation reaction (e.g. C69V, C101A), and the addition of cysteine residues, such as at position 31 (e.g. R31C), to allow for precise PEGylation. These positions may be altered for other reasons as well, or can be mutated to utilize other functional groups in addition to cysteine. Any combination of these sites, or others, can be done.

In an additional aspect, the invention optionally includes variant TNF-α molecules that have modifications for increasing expression in a given expression system. For example, the first residue of human TNF-α, V1, can be modified to V1M, in any combination with the variants outlined herein.

In one aspect, the invention provides TNF-α variants comprising the amino acid substitutions V1M, R31c, C69V, Y87H, C101, and A145R.

In an additional aspect, the invention provides TNF-α variants selected from the group consisting of XENP268 XENP344, XENP345, XENP346, XENP550, XENP551, XENP557, XENP1593, XENP1594, and XENP1595 as outlined in Example 3.

In a further aspect, the invention provides methods of selectively inhibiting the activity of wild-type soluble TNF-α as compared to the activity of transmembrane wild-type TNF-α in a mammal comprising administering to a mammal a variant TNF-α molecule as compared to the corresponding wild-type mammalian TNF-α, wherein the TNF-α variant is substantially free of agonistic activity.

In an additional aspect, the invention provides methods of forming a TNF-α heterotrimer in vivo in a mammal comprising administering to the mammal a variant TNF-α molecule as compared to the corresponding wild-type mammalian TNF-α, wherein said TNF-α variant is substantially free of agonistic activity.

In an additional aspect, the invention provides methods of screening for selective inhibitors comprising contacting a candidate agent with a soluble TNF-α protein and assaying for TNF-α biological activity; contacting a candidate agent with a transmembrane TNF-α protein and assaying for TNF-α biological activity, and determining whether the agent is a selective inhibitor. The agent may be a protein (including peptides and antibodies, as described herein) or small molecules.

In a further aspect, the invention provides variant TNF-α proteins that interact with the wild type TNF-α to form mixed trimers incapable of activating receptor signaling. Preferably, variant TNF-α proteins with 1, 2, 3, 4, 5, 6 and 7 amino acid changes are used as compared to wild type TNF-α protein. In a preferred embodiment, these changes are selected from positions 21, 23, 30, 31, 32, 33, 34, 35, 57, 65, 66, 67, 69, 75, 84, 86, 87, 91, 97, 101, 111, 112, 115, 140, 143, 144, 145, 146 and 147. In an additional aspect, the non-naturally occurring variant TNF-α proteins have substitutions selected from the group of substitutions consisting of Q21C, Q21R, E23C, N34E, V91E, Q21R, N30D, R31c, R311, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R.

In another preferred embodiment, substitutions may be made either individually or in combination, with any combination being possible. Preferred embodiments utilize at least one, and preferably more, positions in each variant TNF-α protein. For example, substitutions at positions 31, 57, 69, 75, 86, 87, 97, 101, 115, 143, 145, and 146 may be combined to form double variants. In addition triple, quadrupal, quintupal and the like, point variants may be generated.

In an additional aspect, the invention provides human TNF-α variants that exchange with and attenuate the signaling potency of soluble TNF. The present invention also provides TNF-α variants that have specificity for TNFR1 or TNFR2.

In yet another aspect, the present invention provides TNF-α variants that have a reduced side effect profile, including reduced infection rates. This is achieved by use of a soluble ligand-selective inhibitor of the present invention.

BRIEF DESCRIPTION OF THE DRAWINGS

FIG. 1 depicts the design strategy for TNF-α mutants. FIG. 1A depicts a complex of TNF receptor with wild type TNF-α. FIG. 1B depicts a mixed trimer of mutant TNF-α (TNF-X) and wild type TNF-α. Dark circles are receptor molecules, light pentagons are wild type TNF-α and the dark pentagon is a mutant TNF-α.

FIG. 2 depicts the structure of the wild type TNF-TNF-R trimer complex.

FIG. 3 depicts the structure of the p55 TNF-R extra-cellular domain. The darker appearing regions represent residues required for contact with TNF-α.

FIG. 4 depicts the binding sites on TNF-α that are involved in binding the TNF-R.

FIG. 5 depicts the TNF-α trimer interface.

FIG. 6A depicts the nucleotide sequence of the histidine tagged wild type TNF-α molecule (SEQ ID NO: 1) used as a template molecule from which the mutants were generated. The additional 6 histidines, located between the start codon and the first amino acid are underlined.

FIG. 6B depicts the amino acid sequence of wild type TNF-α (SEQ ID NO:2) with an additional 6 histidines (underlined) between the start codon and the first amino acid. Amino acids changed in the TNF-α mutants are shown in bold.

FIG. 7 depicts the position and the amino acid changes in the TNF-α mutants.

FIG. 8 depicts the results from a TNF-α activity assay. Only one of the 11 TNF-α variants tested, E146K, was found to have agonistic activity similar to wild-type TNF-α.

FIG. 9 depicts the antagonist activities of the TNF-α variants. The results shown are raw data that have not been normalized as a percent of the control. In this experiment, wild type TNF-α was used at 10 ng/mL. The concentration of the variant TNF-α proteins ranged from 1 ng/mL to 50 μg/mL.

FIGS. 10A and 10B depicts the antagonist activities of the TNF-α variants normalized for percent apoptosis of the control.

FIG. 11 depicts another example of the mutation pattern of TNF-α protein sequences. The probability table shows only the amino acid residues of positions 21, 30, 31, 32, 33, 35, 65, 66, 67, 111, 112, 115, 140, 143, 144, 145, 146 and 147. The occurrence of each amino acid residue at a given position is indicated as a relative probability. For example, at position 21, the wild type amino acid is glutamine; in the TNF-α variants, arginine is the preferred amino acid at this position.

FIGS. 12A-F depicts trimerization domains from TRAF proteins (SEQ ID NOS:3-8).

FIG. 13 depicts the synthesis of a full-length gene and all possible mutations by PCR. Overlapping oligonucleotides corresponding to the full-length gene (black bar, Step 1) and comprising one or more desired mutations are synthesized, heated and annealed. Addition of DNA polymerase to the annealed oligonucleotides results in the 5' to 3' synthesis of DNA (Step 2) to produce longer DNA fragments (Step 3). Repeated cycles of heating, annealing, and DNA synthesis (Step 4) result in the production of longer DNA, including some full-length molecules. These can be selected by a second round of PCR using primers (indicated by arrows) corresponding to the end of the full-length gene (Step 5).

FIG. 14 depicts a preferred method for synthesizing a library of the variant TNF-α proteins of the invention using the wild-type gene.

FIG. 15 depicts another method for generating proteins of the present invention which uses an overlapping extension method. At the top of FIG. 15A is the template DNA showing the locations of the regions to be mutated (black boxes) and the binding sites of the relevant primers (arrows). The primers R1 and R2 represent a pool of primers, each containing a different mutation; as described herein, this may be done using different ratios of primers if desired. The variant position is flanked by regions of homology sufficient to get hybridization. In this example, three separate PCR reactions are done for step 1. The first reaction contains the template plus oligos F1 and R1. The second reaction contains template plus F2 and R2, and the third contains the template and F3 and R3. The reaction products are shown. In Step 2, the products from Step 1 tube 1 and Step 1 tube 2 are taken. After purification away from the primers, these are added to a fresh PCR reaction together with F1 and R4. During the denaturation phase of the PCR, the overlapping regions anneal and the second strand is synthesized. The product is then amplified by the outside primers. In Step 3, the purified product from Step 2 is used in a third PCR reaction, together with the product of Step 1, tube 3 and the primers F1 and R3. The final product corresponds to the full-length gene and contains the required mutations.

FIG. 16 depicts a ligation of PCR reaction products to synthesize the libraries of the invention. In this technique, the primers also contain an endonuclease restriction site (RE), either blunt, 5' overhanging or 3' overhanging. We set up three separate PCR reactions for Step 1. The first reaction contains the template plus oligos F1 and R1. The second reaction contains the template plus F2 and R2, and the third contains the template and F3 and R3. The reaction products are shown. In Step 2, the products of step 1 are purified and then digested with the appropriate restriction endonuclease. The digestion products from Step 2, tube 1 and Step 2, tube 2 and ligate them together with DNA ligase (step 3). The products are then amplified in Step 4 using primer F1 and R4. The whole process is then repeated by digesting the amplified products, ligating them to the digested products of Step 2, tube 3, and amplifying the final product by primers F1 and R3. It would also be possible to ligate all three PCR products from Step 1 together in one reaction, providing the two restriction sites (RET and RE2) were different.

FIG. 17 depicts blunt end ligation of PCR products. In this technique, the primers such as F1 and R1 do not overlap, but they abut. Again three separate PCR reactions are performed. The products from tube 1 and tube 2 are ligated, and then amplified with outside primers F1 and R4. This product is then ligated with the product from Step 1, tube 3. The final products are then amplified with primers F1 and R3.

FIG. 20A is a chart showing that the TNF-α variants of the present invention are pre-exchanged with wild type TNF-α to reduce TNF-α induced activation of NFkB in 293T cells. FIG. 20B are photographs of the immuno-localization of NFkB in HeLa cells showing that the exchange of wild type TNF-α with the A145/Y87H TNF-α variant inhibits TNF-α-induced nuclear translocation of NFkB in HeLa cells. FIG. 20C depicts the TNF-α variant A145/Y87H reduces wild type TNF-α-induced Activation of the NFkB-driven luciferase reporter.

FIG. 25 shows in vitro data of soluble TNF-α variant antagonism with no effect on transmembrane TNF-α (tmTNF) antagonism.

FIG. 27 shows possible mutations to human TNF-α.

Figure 18:
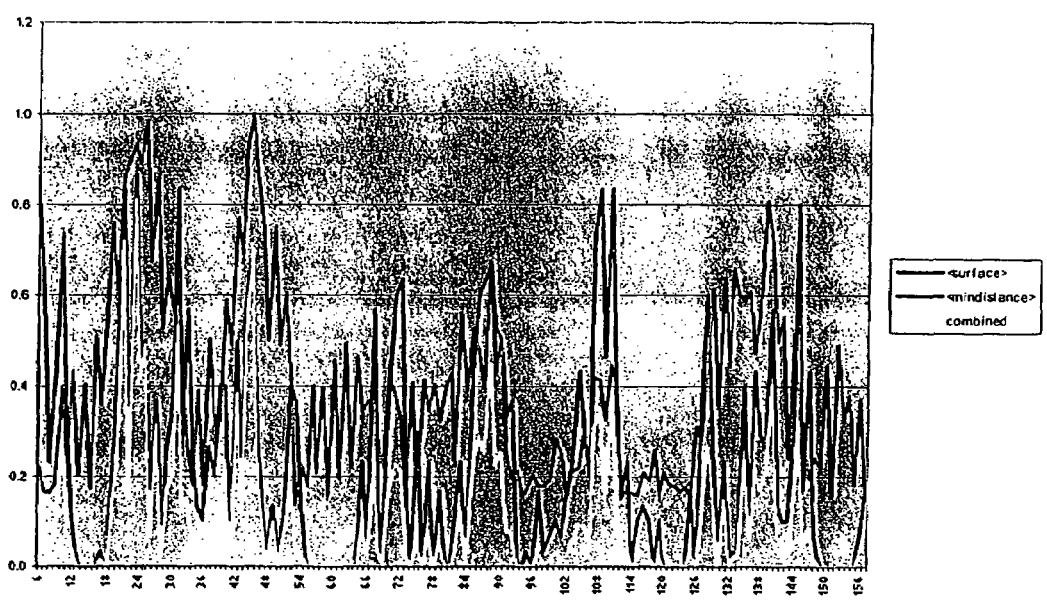
FIG. 18 is a graphical illustration of the approach of identifying chemical modification sites of the wild type TNF-α molecule.
Figure 19A:
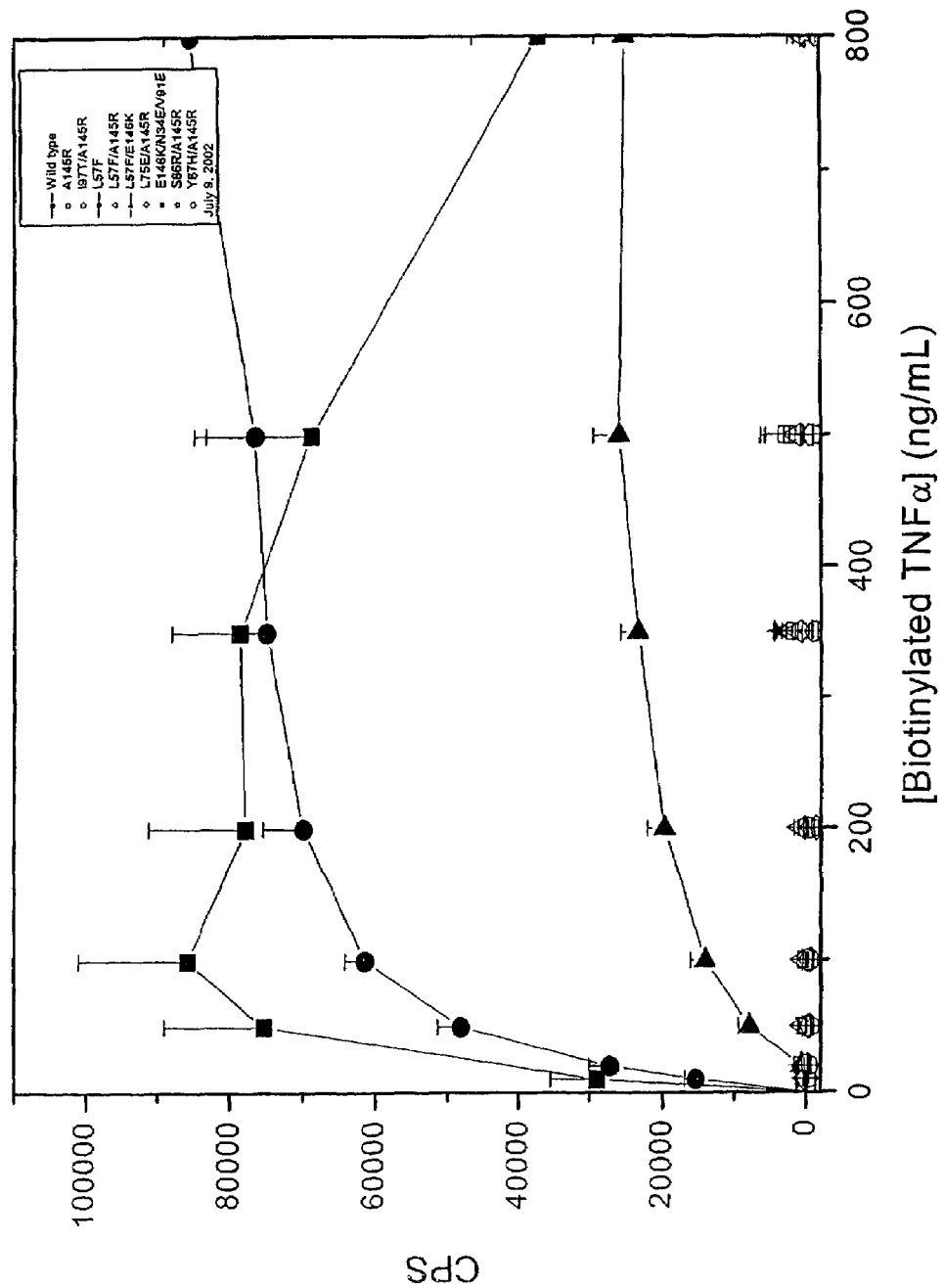
FIGS. 19 A-D depict the results of a TNFR1 binding assay of wild type TNF-α and certain variants of the present invention.
Figure 19B:
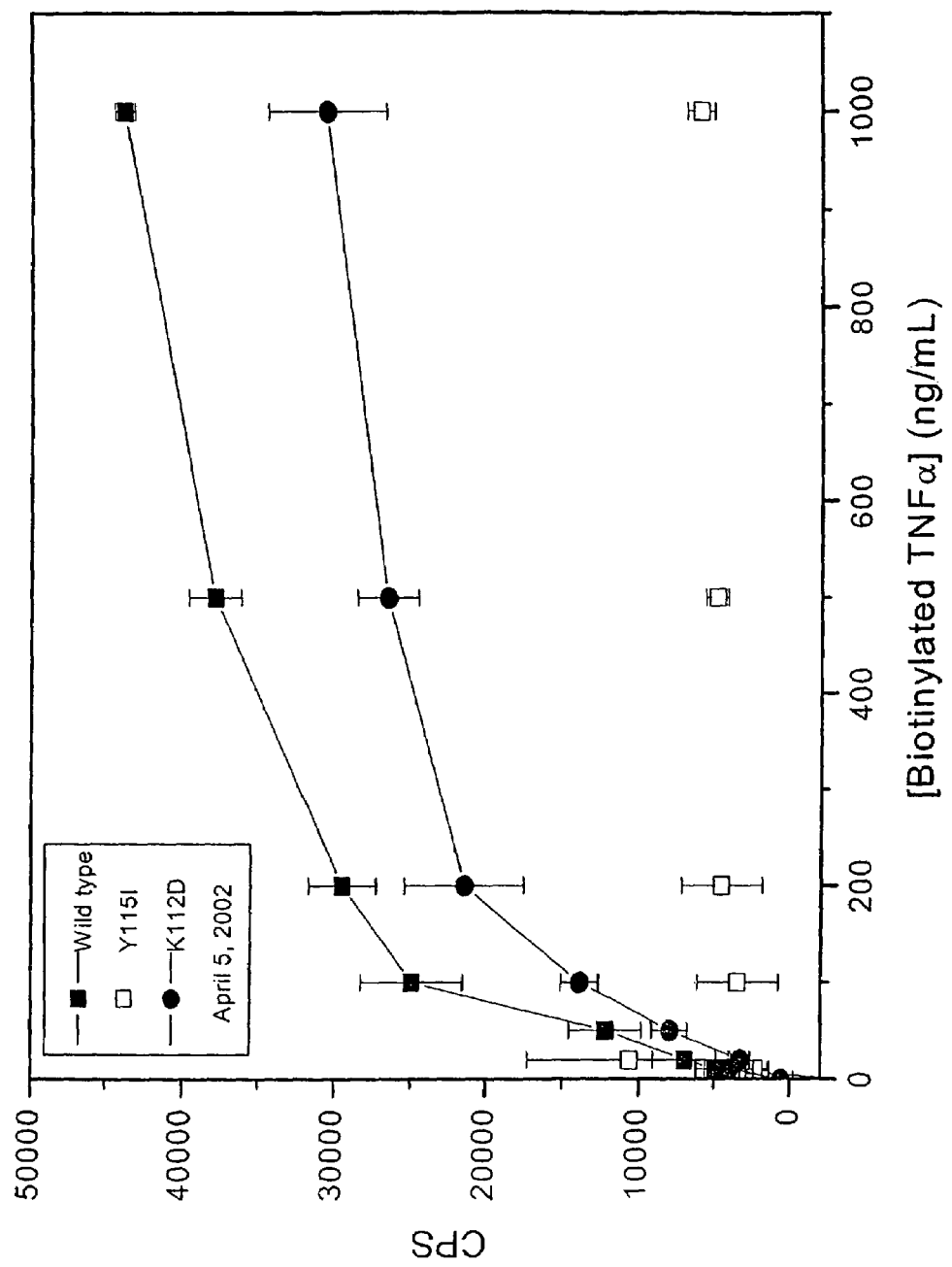
Figure 19C:
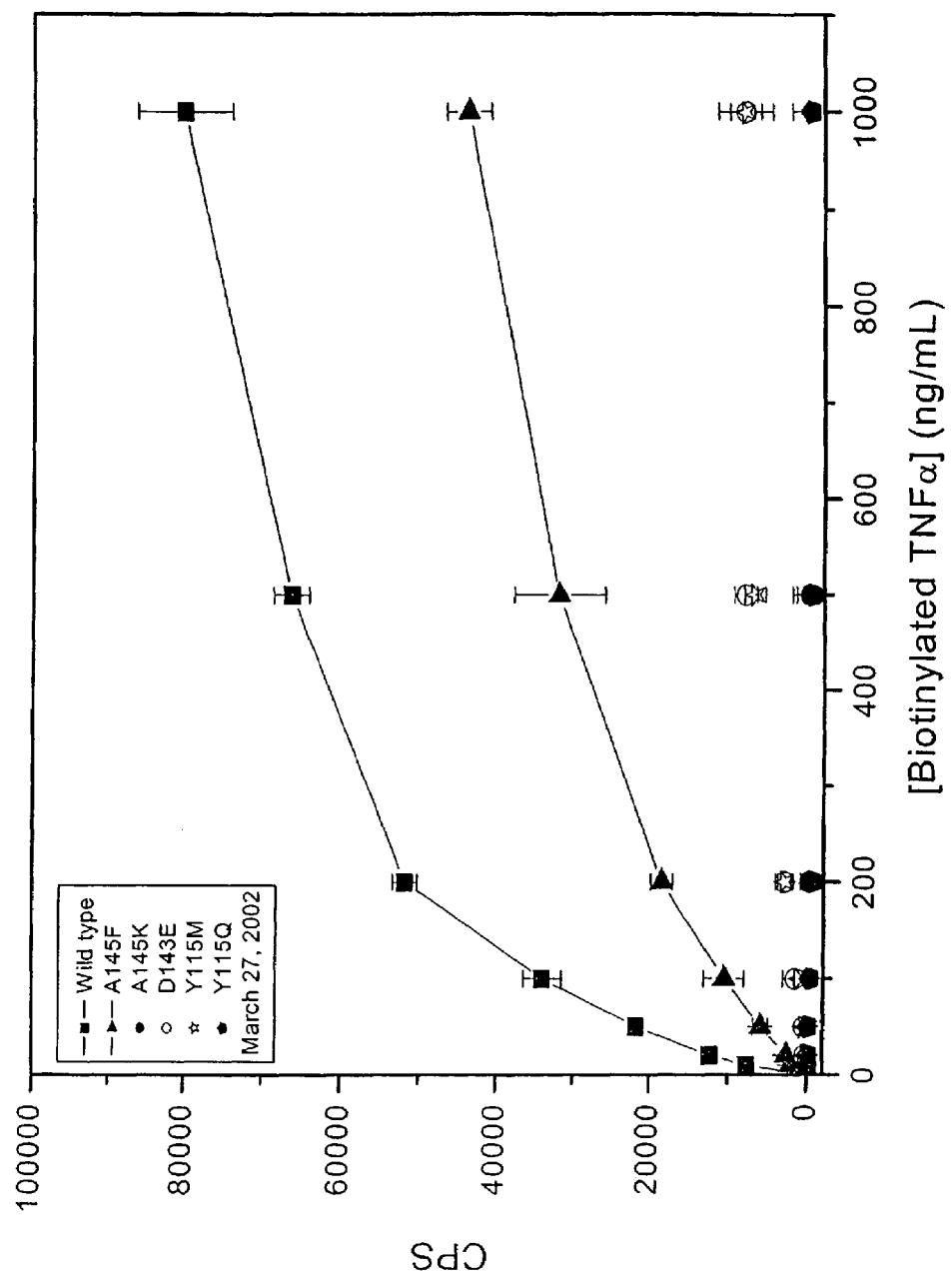
Figure 19D:
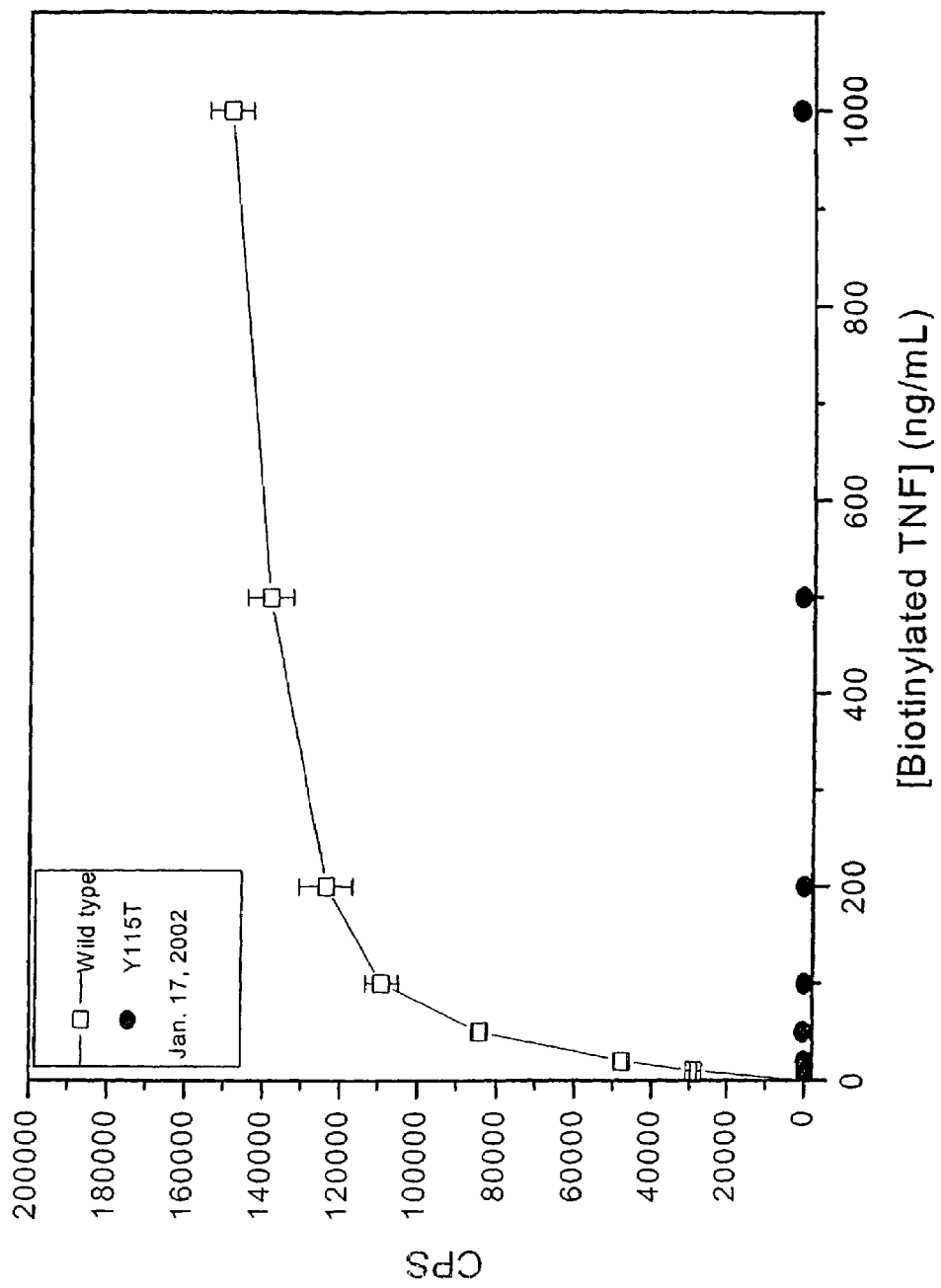

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenyl-glycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)-alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1-C20. Acidic amino acids may be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., —$SO_3H$) threonine, serine, tyrosine. Other substitutions may include unnatural hydroxylated amino acids which may made by combining "alkyl" with any natural amino acid. The term "alkyl" as used refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Alkyl includes heteroalkyl, with atoms of nitrogen, oxygen and sulfur. Preferred alkyl groups herein contain 1 to 12 carbon atoms. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art. In addition, any amide linkage in any of the variant TNF-α polypeptides can be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of variant TNF-α polypeptides of to the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1M sodium cacodylate at pH 6.0. Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters, e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

The TNF-α proteins may be from any number of organisms, with TNF-α proteins from mammals being particularly preferred. Suitable mammals include, but are not limited to, rodents (rats, mice, hamsters, guinea pigs, etc.), primates, farm animals (including sheep, goats, pigs, cows, horses, etc); and in the most preferred embodiment, from humans (the sequence of which is depicted in FIG. 6B (SEQ ID NO:2)). As will be appreciated by those in the art, TNF-α proteins based on TNF-α proteins from mammals other than humans may find use in animal models of human disease and treatment of domesticated animals.

The TNF proteins of the invention have modulated activity as compared to wild type proteins. In a preferred embodiment, variant TNF-α proteins exhibit decreased biological activity (e.g. antagonism) as compared to wild type TNF-α, including but not limited to, decreased binding to a receptor (p55, p75 or both), decreased activation and/or ultimately a loss of cytotoxic activity. By "cytotoxic activity" herein refers to the ability of a TNF-α variant to selectively kill or inhibit cells. Variant TNF-α proteins that exhibit less than 50% biological activity as compared to wild type are preferred. More preferred are variant TNF-α proteins that exhibit less than 25%, even more preferred are variant proteins that exhibit less than 15%, and most preferred are variant TNF-α proteins that exhibit less than 10% of a biological activity of wild-type TNF-α. Suitable assays include, but are not limited to, caspase assays, TNF-α cytotoxicity assays, DNA binding assays; transcription assays (using reporter constructs; see Stpyridi, supra); size exclusion chromatography assays and radiolabeling/immuno-precipitation; see Corcoran et al., supra); and stability assays (including the use of circular dichroism (CD) assays and equilibrium studies; see Mateu, supra); all of which are incorporated by reference.

In one embodiment, at least one property critical for binding affinity of the variant TNF-α proteins is altered when compared to the same property of wild type TNF-α and in particular, variant TNF-α proteins with altered receptor affinity are preferred. Particularly preferred are variant TNF-α with altered affinity toward oligomerization to wild type TNF-α. Thus, the invention provides variant TNF-α proteins with altered binding affinities such that the variant TNF-α proteins will preferentially oligomerize with wild type TNF-α, but do not substantially interact with wild type TNF receptors, i.e., p55, p75. "Preferentially" in this case means that given equal amounts of variant TNF-α monomers and wild type TNF-α monomers, at least 25% of the resulting trimers are mixed trimers of variant and wild type TNF-α, with at least about 50% being preferred, and at least about 80-90% being particularly preferred. In other words, it is preferable that the variant TNF-α proteins of the invention have greater affinity for wild type TNF-α protein as compared to wild type TNF-α proteins. By "do not substantially interact with TNF receptors" is meant that the variant TNF-α proteins will not be able to associate with either the p55 or p75 receptors to significantly activate the receptor and initiate the TNF signaling pathway(s). In a preferred embodiment, at least a 50% decrease in receptor activation is seen, with greater than 50%, 76%, 80-90% being preferred.

Thus, the proteins of the invention are antagonists of wild type TNF-α. By "antagonists of wild type TNF-α" is meant that the variant TNF-α protein inhibits or significantly decreases at least one biological activity of wild-type TNF-α.

In some embodiments, the variants of the invention are antagonists of both soluble and transmembrane TNF-α. However, as described herein, some variant TNF-α proteins are antagonists of the activity of soluble TNF-α but do not substantially effect the activity of transmembrane TNF-α Thus, a reduction of activity of the heterotrimers for soluble TNF-α is as outlined above, with reductions in biological activity of at least 10%, 25, 50, 75, 80, 90, 95, 99 or 100% all being preferred. However, some of the variants outlined herein comprise selective inhibition; that is, they inhibit soluble TNF-α activity but do not substantially inhibit transmembrane TNF-α. In these embodiments, it is preferred that at least 80%, 85, 90, 95, 98, 99 or 100% of the transmembrane TNF-α activity is maintained. This may also be expressed as a ratio; that is, selective inhibition can include a ratio of inhibition of soluble to transmembrane TNF-α. For example, variants that result in at least a 10:1 selective inhibition of soluble to transmembrane TNF-α activity are preferred, with 50:1, 100:1, 200:1, 500:1, 1000:1 or higher find particular use in the invention. Thus one embodiment utilizes variants, such as double mutants at positions 87/145 as outlined herein, that substantially inhibit or eliminate soluble TNF-α activity (for example by exchanging with homotrimeric wild-type to form heterotrimers that do not bind to TNF-α receptors or that bind but do not activate receptor signaling) but do not significantly effect (and preferably do not alter at all) transmembrane TNF-α activity. Without being bound by theory, the variants exhibiting such differential inhibition allow the decrease of inflammation without a corresponding loss in immune response.

In one embodiment, the affected biological activity of the variants is the activation of receptor signaling by wild type TNF-α proteins. In a preferred embodiment, the variant TNF-α protein interacts with the wild type TNF-α protein such that the complex comprising the variant TNF-α and wild type TNF-α has reduced capacity to activate (as outlined above for "substantial inhibition"), and in preferred embodiments is incapable of activating, one or both of the TNF receptors, i.e. p55 TNF-R or p75 TNF-R. In a preferred embodiment, the variant TNF-α protein is a variant TNF-α protein which functions as an antagonist of wild type TNF-α. Preferably, the variant TNF-α protein preferentially interacts with wild type TNF-α to form mixed trimers with the wild type protein such that receptor binding does not significantly occur and/or TNF-α signaling is not initiated (FIG. 1A). By mixed trimers is meant that monomers of wild type and variant TNF-α proteins interact to form heterotrimeric TNF-α (FIG. 5). Mixed trimers may comprise 1 variant TNF-α protein:2 wild type TNF-α proteins, 2 variant TNF-α proteins:1 wild type TNF-α protein. In some embodiments, trimers may be formed comprising only variant TNF-α proteins (FIG. 1B).

The variant TNF-α antagonist proteins of the invention are highly specific for TNF-α antagonism relative to TNF-beta antagonism. Additional characteristics include improved stability, pharmacokinetics, and high affinity for wild type TNF-α. Variants with higher affinity toward wild type TNF-α may be generated from variants exhibiting TNF-α antagonism as outlined above.

As outlined above, the invention provides variant TNF-α nucleic acids encoding variant TNF-α polypeptides. The variant TNF-α polypeptide preferably has at least one altered property as compared to the same property of the corresponding naturally occurring TNF polypeptide. The property of the variant TNF-α polypeptide is the result the PDA® analysis of the present invention. The term "altered property" or grammatical equivalents thereof in the context of a polypeptide, as used herein, further refers to any characteristic or attribute of a polypeptide that can be selected or detected and compared to the corresponding property of a naturally occurring protein. These properties include, but are not limited to cytotoxic activity; oxidative stability, substrate specificity, substrate binding or catalytic activity, thermal stability, alkaline stability, pH activity profile, resistance to proteolytic degradation, kinetic association (Kon) and dissociation (Koff) rate, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and the ability to treat disease.

Unless otherwise specified, a substantial change in any of the above-listed properties, when comparing the property of a variant TNF-α polypeptide to the property of a naturally occurring TNF protein is preferably at least a 20%, more preferably, 50%, more preferably at least a 2-fold increase or decrease. A change in cytotoxic activity is evidenced by at least a 75% or greater decrease in cell death initiated by a variant TNF-α protein as compared to wild type protein. A change in binding affinity is evidenced by at least a 5% or greater increase or decrease in binding affinity to wild type TNF receptor proteins or to wild type TNF-α.

A change in oxidative stability is evidenced by at least about 20%, more preferably at least 50% increase of activity of a variant TNF-α protein when exposed to various oxidizing conditions as compared to that of wild type TNF-α. Oxidative stability is measured by known procedures.

A change in alkaline stability is evidenced by at least about a 5% or greater increase or decrease (preferably increase) in the half-life of the activity of a variant TNF-α protein when exposed to increasing or decreasing pH conditions as compared to that of wild type TNF-α. Generally, alkaline stability is measured by known procedures.

A change in thermal stability is evidenced by at least about a 5% or greater increase or decrease (preferably increase) in the half-life of the activity of a variant TNF-α protein when exposed to a relatively high temperature and neutral pH as compared to that of wild type TNF-α. Generally, thermal stability is measured by known procedures.

Similarly, variant TNF-α proteins, for example are experimentally tested and validated in in vivo and in in vitro assays. Suitable assays include, but are not limited to, activity assays and binding assays. For example, TNF-α activity assays, such as detecting apoptosis via caspase activity can be used to screen for TNF-α variants that are antagonists of wild type TNF-α. Other assays include using the Sytox green nucleic acid stain to detect TNF-induced cell permeability in an Actinomycin-D sensitized cell line. As this stain is excluded from live cells, but penetrates dying cells, this assay also can be used to detect TNF-α variants that are agonists of wild-type TNF-α. By "agonists of "wild type TNF-α" is meant that the variant TNF-α protein enhances the activation of receptor signaling by wild type TNF-α proteins. Generally, variant TNF-α proteins that function as agonists of wild type TNF-α are not preferred. However, in some embodiments, variant TNF-α proteins that function as agonists of wild type TNF-α protein are preferred. An example of an NF kappaB assay is presented in Example 7.

In a preferred embodiment, binding affinities of variant TNF-α proteins as compared to wild type TNF-α proteins for naturally occurring TNF-α and TNF receptor proteins such as p55 and p75 are determined. Suitable assays include, but are not limited to, e.g., quantitative comparisons comparing kinetic and equilibrium binding constants. The kinetic association rate (Kon) and dissociation rate (Koff), and the equilibrium binding constants (Kd) may be determined using surface plasmon resonance on a BIAcore instrument following the standard procedure in the literature [Pearce et al., Biochemistry 38:81-89 (1999), incorporated by reference]. Examples of binding assays are described in Example 6.

In a preferred embodiment, the antigenic profile in the host animal of the variant TNF-α protein is similar, and preferably identical, to the antigenic profile of the host TNF-α; that is, the variant TNF-α protein does not significantly stimulate the host organism (e.g. the patient) to an immune response; that is, any immune response is not clinically relevant and there is no allergic response or neutralization of the protein by an antibody. That is, in a preferred embodiment, the variant TNF-α protein does not contain additional or different epitopes from the TNF-α. By "epitope" or "determinant" is meant a portion of a protein which will generate and/or bind an antibody. Thus, in most instances, no significant amounts of antibodies are generated to a variant TNF-α protein. In general, this is accomplished by not significantly altering surface residues, as outlined below nor by adding any amino acid residues on the surface which can become glycosylated, as novel glycosylation can result in an immune response.

The variant TNF-α proteins and nucleic acids of the invention are distinguishable from naturally occurring wild type TNF-α. By "naturally occurring" or "wild type" or grammatical equivalents, is meant an amino acid sequence or a nucleotide sequence that is found in nature and includes allelic variations; that is, an amino acid sequence or a nucleotide sequence that usually has not been intentionally modified. Accordingly, by "non-naturally occurring" or "synthetic" or "recombinant" or grammatical equivalents thereof, is meant an amino acid sequence or a nucleotide sequence that is not found in nature; that is, an amino acid sequence or a nucleotide sequence that usually has been intentionally modified. It is understood that once a recombinant nucleic acid is made and reintroduced into a host cell or organism, it will replicate non-recombinantly, i.e., using the in vivo cellular machinery of the host cell rather than in vitro manipulations, however, such nucleic acids, once produced recombinantly, although subsequently replicated non-recombinantly, are still considered recombinant for the purpose of the invention. Representative amino acid and nucleotide sequences of a naturally occurring human TNF-α are shown in FIGS. 6A and 6B (SEQ ID NOS:1-2). It should be noted, that unless otherwise stated, all positional numbering of variant TNF-α proteins and variant TNF-α nucleic acids is based on these sequences. That is, as will be appreciated by those in the art, an alignment of TNF-α proteins and variant TNF-α proteins may be done using standard programs, as is outlined below, with the identification of "equivalent" positions between the two proteins. Thus, the variant TNF-α proteins and nucleic acids of the invention are non-naturally occurring; that is, they do not exist in nature.

Thus, in a preferred embodiment, the variant TNF-α protein has an amino acid sequence that differs from a wild type TNF-α sequence by at least 1 amino acid, with from 1, 2, 3, 4, 5, 6, 7, 8, 9 and 10 amino acids all contemplated, or higher. Expressed as a percentage, the variant TNF-α proteins of the invention preferably are greater than 90% identical to wild-type, with greater than 95, 97, 98 and 99% all being contemplated. Stated differently, based on the human TNF sequence of FIG. 6B (SEQ ID NO:2), variant TNF-α proteins have at least about 1 residue that differs from the human TNF-α sequence, with at least about 2, 3, 4, or 5 different residues. Preferred variant TNF-α proteins have 3 to 5 different residues.

Homology in this context means sequence similarity or identity, with identity being preferred. As is known in the art, a number of different programs may be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc, all of which are incorporated by reference.

An example of a useful algorithm is PILEUP. PILEUP creates a multiple sequence alignment from a group of related sequences using progressive, pair wise alignments. It may also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989), both incorporated by reference. Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403-410, (1990); Altschul et al., Nucleic Acids Res. 25:3389-3402 (1997); and Karlin et al., Proc. Natl. Acad. Sci. U.S.A. 90:5873-5787 (1993), both incorporated by reference. A particularly useful BLAST program is the WU-BLAST-2 program which was obtained from Altschul et al., Methods in Enzymology, 266:460-480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST, as reported by Altschul et al., Nucl. Acids Res., 25:3389-3402, incorporated by reference. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). In a similar manner, "percent (%) nucleic acid sequence identity" with respect to the coding sequence of the polypeptides identified is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 6B (SEQ ID NO:2), it is understood that in one embodiment, the percentage of sequence identity will be determined based on the number of identical amino acids in relation to the total number of amino acids. Thus, for example, sequence identity of sequences shorter than that shown in FIG. 6B (SEQ ID NO:2), as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity may be calculated, for example, by dividing the number of matching identical residues by the total number of residues of the "shorter" sequence in the aligned region and multiplying by 100. The "longer" sequence is the one having the most actual residues in the aligned region.

Thus, the variant TNF-α proteins of the present invention may be shorter or longer than the amino acid sequence shown in FIG. 6B (SEQ ID NO:2). As used in this invention, "wild type TNF-α" is a native mammalian protein (preferably human). TNF-α is polymorphic. An example of the amino acid sequences shown in FIG. 6B (SEQ ID NO:2). Thus, in a preferred embodiment, included within the definition of variant TNF proteins are portions or fragments of the sequences depicted herein. Fragments of variant TNF-α proteins are considered variant TNF-α proteins if a) they share at least one antigenic epitope; b) have at least the indicated homology; c) and preferably have variant TNF-α biological activity as defined herein.

In a preferred embodiment, as is more fully outlined below, the variant TNF-α proteins include further amino acid variations, as compared to a wild type TNF-α, than those outlined herein. In addition, any of the variations depicted herein may be combined in any way to form additional novel variant TNF-α proteins. In addition, variant TNF-α proteins may be made that are longer than those depicted in the figures, for example, by the addition of epitope or purification tags, as outlined herein, the addition of other fusion sequences, etc.

TNF-α proteins may be fused to, for example, to other therapeutic proteins or to other proteins such as Fc or serum albumin for therapeutic or pharmacokinetic purposes. In this embodiment, a TNF-α protein of the present invention is operably linked to a fusion partner. The fusion partner may be any moiety that provides an intended therapeutic or pharmacokinetic effect. Examples of fusion partners include but are not limited to Human Serum Albumin, a therapeutic agent, a cytotoxic or cytotoxic molecule, radionucleotide, and an Fc, etc. As used herein, an Fc fusion is synonymous with the terms "immunoadhesin", "Ig fusion", "Ig chimera", and "receptor globulin" as used in the prior art (Chamow et al., 1996, Trends Biotechnol 14:52-60; Ashkenazi et al., 1997, Curr Opin Immunol 9:195-200, both incorporated by reference). An Fc fusion combines the Fc region of an immunoglobulin with the target-binding region of a TNF-α protein, for example. See for example U.S. Pat. Nos. 5,766,883 and 5,876,969, both of which are incorporated by reference.

In a preferred embodiment, the variant TNF-α proteins comprise residues selected from the following positions 21, 23, 30, 31, 32, 33, 34, 35, 57, 65, 66, 67, 69, 75, 84, 86, 87, 91, 97, 101, 111, 112, 115, 140, 143, 144, 145, 146, and 147. Preferred amino acids for each position, including the human TNF-α residues, are shown in FIG. 7. Thus, for example, at position 143, preferred amino acids are Glu, Asn, Gln, Ser, Arg, and Lys; etc. Preferred changes include: Q21C, Q21 R, E23C, N34E, V91E, Q21R, N30D, R31C, R31I, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, C69V, L75E, L75K, L75Q, A84V, S86Q, S86R, Y87H, Y87R, V91E, I97R, I97T, C101A, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R. These may be done either individually or in combination, with any combination being possible. However, as outlined herein, preferred embodiments utilize at least 1 to 5, and preferably more, positions in each variant TNF-α protein.

For purposes of the present invention, the areas of the wild type or naturally occurring TNF-α molecule to be modified are selected from the group consisting of the Large Domain (also known as II), Small Domain (also known as I), the DE loop, and the trimer interface. The Large Domain, the Small Domain and the DE loop are the receptor interaction domains. The modifications may be made solely in one of these areas or in any combination of these areas. The Large Domain preferred positions to be varied include: 21, 30, 31, 32, 33, 35, 65, 66, 67, 111, 112, 115, 140, 143, 144, 145, 146 and/or 147 (FIG. 11). For the Small Domain, the preferred positions to be modified are 75 and/or 97. For the DE Loop, the preferred position modifications are 84, 86, 87 and/or 91. The Trimer Interface has preferred double variants including positions 34 and 91 as well as at position 57. In a preferred embodiment, substitutions at multiple receptor interaction and/or trimerization domains may be combined. Examples include, but are not limited to, simultaneous substitution of amino acids at the large and small domains (e.g. A145R and I97T), large domain and DE loop (A145R and Y87H), and large domain and trimerization domain (A145R and L57F). Additional examples include any and all combinations, e.g., I97T and Y87H (small domain and DE loop). More specifically, theses variants may be in the form of single point variants, for example K112D, Y115K, Y115I, Y115T, A145E or A145R. These single point variants may be combined, for example, Y115I and A145E, or Y115I and A145R, or Y115T and A145R or Y115I and A145E; or any other combination.

Preferred double point variant positions include 57, 75, 86, 87, 97, 115, 143, 145, and 146; in any combination. In addition, double point variants may be generated including L57F and one of Y115I, Y115Q, Y115T, D143K, D143R, D143E, A145E, A145R, E146K or E146R. Other preferred double variants are Y115Q and at least one of D143N, D143Q, A145K, A145R, or E146K; Y115M and at least one of D143N, D143Q, A145K, A145R or E146K; and L57F and at least one of A145E or 146R; K65D and either D143K or D143R, K65E and either D143K or D143R, Y115Q and any of L75Q, L57W, L57Y, L57F, I97R, I97T, S86Q, D143N, E146K, A145R and I97T, A145R and either Y87R or Y87H; N34E and V91E; L75E and Y115Q; L75Q and Y115Q; L75E and A145R; and L75Q and A145R.

Further, triple point variants may be generated. Preferred positions include 34, 75, 87, 91, 115, 143, 145 and 146. Examples of triple point variants include V91 E, N34E and one of Y115I, Y115T, D143K, D143R, A145R, A145E E146K, and E146R. Other triple point variants include L75E and Y87H and at least one of Y115Q, A145R, Also, L75K, Y87H and Y115Q. More preferred are the triple point variants V91E, N34E and either A145R or A145E.

In a preferred embodiment, the variant TNF-α proteins of the invention are human TNF-α conformers. By "conformer" is meant a protein that has a protein backbone 3-D structure that is virtually the same but has significant differences in the amino acid side chains. That is, the variant TNF-α proteins of the invention define a conformer set, wherein all of the proteins of the set share a backbone structure and yet have sequences that differ by at least 1-3-5%. The three dimensional backbone structure of a variant TNF-α protein thus substantially corresponds to the three-dimensional backbone structure of human TNF-α. "Backbone" in this context means the non-side chain atoms: the nitrogen, carbonyl carbon and oxygen, and the α-carbon, and the hydrogens attached to the nitrogen and α-carbon. To be considered a conformer, a protein must have backbone atoms that are no more than 2 Angstroms RMSD from the human TNF-α structure, with no more than 1.5 Angstroms RMSD being preferred, and no more than 1 Angstrom RMSD being particularly preferred. In general, these distances may be determined in two ways. In one embodiment, each potential conformer is crystallized and its three-dimensional structure determined. Alternatively, as the former is quite tedious, the sequence of each potential conformer is run in the PDATM technology program to determine whether it is a conformer.

Variant TNF-α proteins may also be identified as being encoded by variant TNF-α nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred. In a preferred embodiment, a variant TNF-α nucleic acid encodes a variant TNF-α protein. As will be appreciated by those in the art, due to the degeneracy of the genetic code, an extremely large number of nucleic acids may be made, all of which encode the variant TNF-α proteins of the present invention. Thus, having identified a particular amino acid sequence, those skilled in the art could make any number of different nucleic acids, by simply modifying the sequence of one or more codons in a way which does not change the amino acid sequence of the variant TNF-α.

In one embodiment, the nucleic acid homology is determined through hybridization studies. Thus, for example, nucleic acids which hybridize under high stringency to the nucleic acid sequence shown in FIG. 6A (SEQ ID NO:1) or its complement and encode a variant TNF-α protein is considered a variant TNF-α gene. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993), incorporated by reference. Generally, stringent conditions are selected to be about 5-10 degrees C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30 degrees C. for short probes (e.g. 10 to 50 nucleotides) and at least about 60 degrees C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

The variant TNF-α proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half-life of such molecules in physiological environments. The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 6A (SEQ ID NO:1) also includes the complement of the sequence. By the term "recombinant nucleic acid" is meant nucleic acid, originally formed in vitro, in general, by the manipulation of nucleic acid by endonucleases, in a form not normally found in nature. Thus an isolated variant TNF-α nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild-type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a variant TNF-α protein from one organism in a different organism or host cell. Alternatively, the protein may be made at a significantly higher concentration than is normally seen, through the use of a inducible promoter or high expression promoter, such that the protein is made at increased concentration levels. Furthermore, all of the variant TNF-α proteins outlined herein are in a form not normally found in nature, as they contain amino acid substitutions, insertions and deletions, with substitutions being preferred, as discussed below.

Also included within the definition of variant TNF-α proteins of the present invention are amino acid sequence variants of the variant TNF-α sequences outlined herein and shown in the Figures. That is, the variant TNF-α proteins may contain additional variable positions as compared to human TNF-α. These variants fall into one or more of three classes: substitutional, insertional or deletional variants. These variants ordinarily are prepared by site-specific mutagenesis of nucleotides in the DNA encoding a variant TNF-α protein, using cassette or PCR mutagenesis or other techniques well known in the art, to produce DNA encoding the variant, and thereafter expressing the DNA in recombinant cell culture as outlined above. However, variant TNF-α protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the variant TNF-α protein amino acid sequence. The variants typically exhibit the same qualitative biological activity as the naturally occurring analogue; although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed variant TNF-α proteins screened for the optimal combination of desired activity. Techniques for making substitution mutations at predetermined sites in DNA having a known sequence are well known, for example, M13 primer mutagenesis and PCR mutagenesis. Screening of the mutants is done using assays of variant TNF-α protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the variant TNF-α protein are desired, substitutions are often made in accordance with the following: Ala to Ser; Arg to Lys; Asn to Gln, His; Asp to Glu; Cys to Ser, Ala; Gln to Asn; Glu to Asp; Gly to Pro; His to Asn, Gln; Ile to Leu, Val; Leu to Ile, Val; Lys to Arg, Gln, Glu; Met to Leu, Ile; Phe to Met, Leu, Tyr; Ser to Thr; Thr to Ser; Trp to Tyr; Tyr to Trp, Phe; Val to Ile, Leu.

Substantial changes in function or immunological identity are made by selecting substitutions that are less conservative than those shown above. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the original variant TNF-α protein, although variants also are selected to modify the characteristics of the variant TNF-α proteins as needed. Alternatively, the variant may be designed such that the biological activity of the variant TNF-α protein is altered. For example, glycosylation and/or pegylation sites may be altered or removed. Similarly, the biological function may be altered; for example, in some instances it may be desirable to have more or less potent TNF-α activity.

The variant TNF-α proteins and nucleic acids of the invention can be made in a number of ways. Individual nucleic acids and proteins can be made as known in the art and outlined below. Alternatively, libraries of variant TNF-α proteins can be made for testing. In a preferred embodiment, sets or libraries of variant TNF-α proteins are generated from a probability distribution table. As outlined herein, there are a variety of methods of generating a probability distribution table, including using PDA® technology calculations, sequence alignments, forcefield calculations such as SCMF calculations, etc. In addition, the probability distribution can be used to generate information entropy scores for each position, as a measure of the mutational frequency observed in the library. In this embodiment, the frequency of each amino acid residue at each variable position in the list is identified. Frequencies may be thresholded, wherein any variant frequency lower than a cutoff is set to zero. This cutoff is preferably 1%, 2%, 5%, 10% or 20%, with 10% being particularly preferred. These frequencies are then built into the variant TNF-α library. That is, as above, these variable positions are collected and all possible combinations are generated, but the amino acid residues that "fill" the library are utilized on a frequency basis. Thus, in a non-frequency based library, a variable position that has 5 possible residues will have 20% of the proteins comprising that variable position with the first possible residue, 20% with the second, etc. However, in a frequency based library, a variable position that has 5 possible residues with frequencies of 10%, 15%, 25%, 30% and 20%, respectively, will have 10% of the proteins comprising that variable position with the first possible residue, 15% of the proteins with the second residue, 25% with the third, etc. As will be appreciated by those in the art, the actual frequency may depend on the method used to actually generate the proteins; for example, exact frequencies may be possible when the proteins are synthesized. However, when the frequency-based primer system outlined below is used, the actual frequencies at each position will vary, as outlined below.

In another embodiment, the novel trimeric complexes that are formed will act as competitive inhibitors of normal receptor signaling without the signaling produced by divalent binders. The heterotrimer complex of the present invention has a single, monovalent receptor binding site.

The receptor binding interface of trimeric TNF ligands has two sides, each contributed by a different monomer subunit. One side consists of the "Large Domain" while the other is made up of the "Small Domain" and the "DE Loop". Disruption of receptor binding and consequent agonist can be achieved by mutations on either binding face alone. Complementary mutations in the same molecule on both binding faces generally are even more effective at disruption. For example the Large Domain double mutant D143N/A145R and Small Domain mutant Y87H effectively eliminate binding/signaling. In a homotrimeric complex of a mutant at a single face, each of the three receptor binding sites will be disrupted. In a heterotrimeric mixture of complementary mutations on different faces, as may be achieved by co-expression or exchange, there will be one receptor binding site disrupted on one face, one disrupted on two faces, and a third with no disruption.

In a preferred embodiment, the different protein members of the variant TNF-α library may be chemically synthesized. This is particularly useful when the designed proteins are short, preferably less than 150 amino acids in length, with less than 100 amino acids being preferred, and less than 50 amino acids being particularly preferred, although as is known in the art, longer proteins may be made chemically or enzymatically. See for example Wilken et al, Curr. Opin. Biotechnol. 9:412-26 (1998), hereby incorporated by reference.

In a preferred embodiment, particularly for longer proteins or proteins for which large samples are desired, the library sequences are used to create nucleic acids such as DNA which encode the member sequences and which may then be cloned into host cells, expressed and assayed, if desired. Thus, nucleic acids, and particularly DNA, may be made which encodes each member protein sequence. This is done using well known procedures. The choice of codons, suitable expression vectors and suitable host cells will vary depending on a number of factors, and may be easily optimized as needed.

In a preferred embodiment, multiple PCR reactions with pooled oligonucleotides are done, as is generally depicted in the FIGS. 13-17. In this embodiment, overlapping oligonucleotides are synthesized which correspond to the full-length gene. Again, these oligonucleotides may represent all of the different amino acids at each variant position or subsets.

In a preferred embodiment, these oligonucleotides are pooled in equal proportions and multiple PCR reactions are performed to create full-length sequences containing the combinations of mutations defined by the library. In addition, this may be done using error-prone PCR methods. In a preferred embodiment, the different oligonucleotides are added in relative amounts corresponding to the probability distribution table. The multiple PCR reactions thus result in full length sequences with the desired combinations of mutations in the desired proportions. The total number of oligonucleotides needed is a function of the number of positions being mutated and the number of mutations being considered at these positions:

$$\text{(number of oligos for constant positions)}+M1+M2+M_n=\text{(total number of oligos required)}$$

where $M_n$ is the number of mutations considered at position n in the sequence. The total number of oligonucleotides required increases when multiple mutable positions are encoded by a single oligonucleotide. The annealed regions are the ones that remain constant, i.e. have the sequence of the reference sequence.

Oligonucleotides with insertions or deletions of codons may be used to create a library expressing different length proteins. In particular computational sequence screening for insertions or deletions may result in secondary libraries defining different length proteins, which can be expressed by a library of pooled oligonucleotide of different lengths. In a preferred embodiment, the variant TNF-α library is done by shuffling the family (e.g. a set of variants); that is, some set of the top sequences (if a rank-ordered list is used) can be shuffled, either with or without error-prone PCR. "Shuffling" in this context means a recombination of related sequences, generally in a random way. It can include "shuffling" as defined and exemplified in U.S. Pat. Nos. 5,830,721; 5,811,238; 5,605,793; 5,837,458 and PCT US/19256, all of which are incorporated by reference. This set of sequences may also be an artificial set; for example, from a probability table (for example generated using SCMF) or a Monte Carlo set. Similarly, the "family" can be the top 10 and the bottom 10 sequences, the top 100 sequences, etc. This may also be done using error-prone PCR.

In a preferred embodiment, error-prone PCR is done to generate the variant TNF-α library. See U.S. Pat. Nos. 5,605,793, 5,811,238, and 5,830,721, all incorporated by reference. This may be done on the optimal sequence or on top members of the library, or some other artificial set or family. In this embodiment, the gene for the optimal sequence found in the computational screen of the primary library may be synthesized. Error-prone PCR is then performed on the optimal sequence gene in the presence of oligonucleotides that code for the mutations at the variant positions of the library (bias oligonucleotides). The addition of the oligonucleotides will create a bias favoring the incorporation of the mutations in the library. Alternatively, only oligonucleotides for certain mutations may be used to bias the library.

In a preferred embodiment, gene shuffling with error-prone PCR can be performed on the gene for the optimal sequence, in the presence of bias oligonucleotides, to create a DNA sequence library that reflects the proportion of the mutations found in the variant TNF-α library. The choice of the bias oligonucleotides can be done in a variety of ways; they can chosen on the basis of their frequency, i.e. oligonucleotides encoding high mutational frequency positions can be used; alternatively, oligonucleotides containing the most variable positions can be used, such that the diversity is increased; if the secondary library is ranked, some number of top scoring positions may be used to generate bias oligonucleotides; random positions may be chosen; a few top scoring and a few low scoring ones may be chosen; etc. What is important is to generate new sequences based on preferred variable positions and sequences.

In a preferred embodiment, PCR using a wild-type gene or other gene may be used, as is schematically depicted in the Figures. In this embodiment, a starting gene is used; generally, although this is not required, the gene is usually the wild-type gene. In some cases it may be the gene encoding the global optimized sequence, or any other sequence of the list, or a consensus sequence obtained e.g. from aligning homologous sequences from different organisms. In this embodiment, oligonucleotides are used that correspond to the variant positions and contain the different amino acids of the library. PCR is done using PCR primers at the termini, as is known in the art. This provides two benefits. First, this generally requires fewer oligonucleotides and may result in fewer errors. Second, it has experimental advantages in that if the wild-type gene is used, it need not be synthesized. In addition, there are several other techniques that may be used, as exemplified in FIGS. 13-17.

In a preferred embodiment, a variety of additional steps may be done to the variant TNF-α library; for example, further computational processing may occur, different variant TNF-α libraries can be recombined, or cutoffs from different libraries may be combined. In a preferred embodiment, a variant TNF-α library may be computationally remanipulated to form an additional variant TNF-α library (sometimes referred to as "tertiary libraries"). For example, any of the variant TNF-α library sequences may be chosen for a second round of PDA®, by freezing or fixing some or all of the changed positions in the first library. Alternatively, only changes seen in the last probability distribution table are allowed. Alternatively, the stringency of the probability table may be altered, either by increasing or decreasing the cutoff for inclusion. Similarly, the variant TNF-α library may be recombined experimentally after the first round; for example, the best gene/genes from the first screen may be taken and gene assembly redone (using techniques outlined below, multiple PCR, error-prone PCR, shuffling, etc.). Alternatively, the fragments from one or more good gene(s) to change probabilities at some positions.

In a preferred embodiment, a tertiary library may be generated from combining different variant TNF-α libraries. For example, a probability distribution table from a first variant TNF-α library may be generated and recombined, either computationally or experimentally, as outlined herein. A PDA™ variant TNF-α library may be combined with a sequence alignment variant TNF-α library, and either recombined (again, computationally or experimentally) or just the cutoffs from each joined to make a new tertiary library. The top sequences from several libraries may be recombined. Sequences from the top of a library may be combined with sequences from the bottom of the library to more broadly sample sequence space, or only sequences distant from the top of the library may be combined. Variant TNF-α libraries that analyzed different parts of a protein may be combined to a tertiary library that treats the combined parts of the protein.

In a preferred embodiment, a tertiary library may be generated using correlations in a variant TNF-α library. That is, a residue at a first variable position may be correlated to a residue at second variable position (or correlated to residues at additional positions as well). For example, two variable positions may sterically or electrostatically interact, such that if the first residue is X, the second residue must be Y. This may be either a positive or negative correlation.

Using the nucleic acids of the present invention which encode a variant TNF-α protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the variant TNF-α protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the variant TNF-α protein, a replacement of the naturally occurring secretory leader sequence is desired. In this embodiment, an unrelated secretory leader sequence is operably linked to a variant TNF-α encoding nucleic acid leading to increased protein secretion. Thus, any secretory leader sequence resulting in enhanced secretion of the variant TNF-α protein, when compared to the secretion of TNF-α and its secretory sequence, is desired. Suitable secretory leader sequences that lead to the secretion of a protein are known in the art. In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences. Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used. A preferred expression vector system is a retroviral vector system such as is generally described in PCT/US97/01019 and PCT/US97/01048, both of which are hereby incorporated by reference. In a preferred embodiment, the expression vector comprises the components described above and a gene encoding a variant TNF-α protein. As will be appreciated by those in the art, all combinations are possible and accordingly, as used herein, the combination of components, comprised by one or more vectors, which may be retroviral or not, is referred to herein as a "vector composition".

The variant TNF-α nucleic acids are introduced into the cells either alone or in combination with an expression vector. By "introduced into" or grammatical equivalents is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The variant TNF-α nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

The variant TNF-α proteins of the present invention are produced by culturing a host cell transformed with an expression vector containing nucleic acid encoding a variant TNF-α protein, under the appropriate conditions to induce or cause expression of the variant TNF-α protein. The conditions appropriate for variant TNF-α protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield. Appropriate host cells include yeast, bacteria, archaebacteria, fungi, and insect and animal cells, including mammalian cells. Of interest are *Drosophila melangaster* cells, *Saccharomyces cerevisiae* and other yeasts, *E. coli, Bacillus subtilis*, SF9 cells, C129 cells, 293 cells, *Neurospora*, BHK, CHO, COS, *Pichia pastoris*, etc.

In a preferred embodiment, the variant TNF-α proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoietic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, COS, etc. See the ATCC cell line catalog, hereby incorporated by reference.

In one embodiment, the cells may be additionally genetically engineered, that is, contain exogenous nucleic acid other than the variant TNF-α nucleic acid. In a preferred embodiment, the variant TNF-α proteins are expressed in bacterial systems. Bacterial expression systems are well known in the art. A suitable bacterial promoter is any nucleic acid sequence capable of binding bacterial RNA polymerase and initiating the downstream (3') transcription of the coding sequence of the variant TNF-α protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter may include naturally occurring promoters of non-bacterial origin that have the ability to bind bacterial RNA polymerase and initiate transcription. In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the variant TNF-α protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria). For expression in bacteria, usually bacterial secretory leader sequences, operably linked to a variant TNF-α encoding nucleic acid, are preferred. The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis*, *E. coli*, *Streptococcus cremoris*, and *Streptococcus lividans*, among others. The bacterial expression vectors are transformed into bacterial host cells using techniques well known in the art, such as calcium chloride treatment, electroporation, and others. In one embodiment, variant TNF-α proteins are produced in insect cells. Expression vectors for the transformation of insect cells, and in particular, baculovirus-based expression vectors, are well known in the art. In a preferred embodiment, variant TNF-α protein is produced in yeast cells. Yeast expression systems are well known in the art, and include expression vectors for *Saccharomyces cerevisiae*, *Candida albicans* and *C. maltosa*, *Hansenula polymorpha*, *Kluyveromyces fragilis* and *K. lactis*, *Pichia guillerimondii* and *P. pastoris*, *Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In an alternative embodiment, modified TNF variants are covalently coupled to at least one additional TNF variant via a linker to improve the dominant negative action of the modified domains. A number of strategies may be used to covalently link modified receptor domains together. These include, but are not limited to, linkers, such as polypeptide linkages between N- and C-termini of two domains, linkage via a disulfide bond between monomers, and linkage via chemical cross-linking reagents. Alternatively, the N- and C-termini may be covalently joined by deletion of portions of the N- and/or C-termini and linking the remaining fragments via a linker or linking the fragments directly.

By "linker", "linker sequence", "spacer", "tethering sequence" or grammatical equivalents thereof, is meant a molecule or group of molecules (such as a monomer or polymer) that connects two molecules and often serves to place the two molecules in a preferred configuration. In one aspect of this embodiment, the linker is a peptide bond. Choosing a suitable linker for a specific case where two polypeptide chains are to be connected depends on various parameters, e.g., the nature of the two polypeptide chains (e.g., whether they naturally oligomerize (e.g., form a dimer or not), the distance between the N- and the C-termini to be connected if known from three-dimensional structure determination, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. These linked TNF-α proteins have constrained hydrodynamic properties, that is, they form constitutive dimers) and thus efficiently interact with other naturally occurring TNF-α proteins to form a dominant negative heterotrimer.

The linker peptide should have a length that is adequate to link two TNF variant monomers in such a way that they assume the correct conformation relative to one another so that they retain the desired activity as antagonists of the TNF receptor. Suitable lengths for this purpose include at least one and not more than 30 amino acid residues. Preferably, the linker is from about 1 to 30 amino acids in length, with linkers of 1, 2, 3, 4, 5, 6, 7, 8, 9, 10, 11, 12, 13, 14, 15, 16, 17, 18, 19 and 20 amino acids in length being preferred. See also WO 01/25277, incorporated by reference in its entirety.

In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers (including, for example, (GS)n, (GSGGS)n (SEQ ID NO:9), (GGGGS)n (SEQ ID NO:10) and (GGGS)n (SEQ ID NO:11), where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies. Suitable linkers may also be identified by screening databases of known three-dimensional structures for naturally occurring motifs that can bridge the gap between two polypeptide chains. Another way of obtaining a suitable linker is by optimizing a simple linker, e.g., (Gly4Ser)n (SEQ ID NO:10), through random mutagenesis. Alternatively, once a suitable polypeptide linker is defined, additional linker polypeptides can be created by application of PDA® technology to select amino acids that more optimally interact with the domains being linked. Other types of linkers that may be used in the present invention include artificial polypeptide linkers and inteins. In another preferred embodiment, disulfide bonds are designed to link the two receptor monomers at inter-monomer contact sites. In one aspect of this embodiment the two receptors are linked at distances <5 Angstroms. In addition, the variant TNF-α polypeptides of the invention may be further fused to other proteins, if desired, for example to increase expression or stabilize the protein.

In one embodiment, the variant TNF-α nucleic acids, proteins and antibodies of the invention are labeled with a label other than the scaffold. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Once made, the variant TNF-α proteins may be covalently modified. Covalent and non-covalent modifications of the protein are thus included within the scope of the present invention. Such modifications may be introduced into a variant TNF-α polypeptide by reacting targeted amino acid residues of the polypeptide with an organic derivatizing agent that is capable of reacting with selected side chains or terminal residues. One type of covalent modification includes reacting targeted amino acid residues of a variant TNF-α polypeptide with an organic derivatizing agent that is capable of reacting with selected side chains or the N- or C-terminal residues of a variant TNF-α polypeptide. Derivatization with bifunctional agents is useful, for instance, for cross linking a variant TNF-α protein to a water-insoluble support matrix or surface for use in the method for purifying anti-variant TNF-α antibodies or screening assays, as is more fully described below. Commonly used cross linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T.E. Creighton, Proteins: Structure and Molecular Properties, W.H. Freeman & Co., San Francisco, pp. 79-86 (1983), incorporated by reference,] acetylation of the N-terminal amine, and amidation of any C-terminal carboxyl group.

Another type of covalent modification of the variant TNF-α polypeptide included within the scope of this invention comprises altering the native glycosylation pattern of the polypeptide. "Altering the native glycosylation pattern" is intended for purposes herein to mean deleting one or more carbohydrate moieties found in native sequence variant TNF-α polypeptide, and/or adding one or more glycosylation sites that are not present in the native sequence variant TNF-α polypeptide. Addition of glycosylation sites to variant TNF-α polypeptides may be accomplished by altering the amino acid sequence thereof. The alteration may be made, for example, by the addition of, or substitution by, one or more serine or threonine residues to the native sequence or variant TNF-α polypeptide (for O-linked glycosylation sites). The variant TNF-α amino acid sequence may optionally be altered through changes at the DNA level, particularly by mutating the DNA encoding the variant TNF-α polypeptide at preselected bases such that codons are generated that will translate into the desired amino acids.

Addition of N-linked glycosylation sites to variant TNF-α polypeptides may be accomplished by altering the amino acid sequence thereof. The alteration may be made, for example, by the addition of, or substitution by, one or more asparagine residues to the native sequence or variant TNF-α polypeptide. The modification may be made for example by the incorporation of a canonical N-linked glycosylation site, including but not limited to, N-X-Y, where X is any amino acid except for proline and Y is preferably threonine, serine or cysteine. Another means of increasing the number of carbohydrate moieties on the variant TNF-α polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981), incorporated by reference. Removal of carbohydrate moieties present on the variant TNF-α polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987), incorporated by reference. Such derivatized moieties may improve the solubility, absorption, and permeability across the blood brain barrier biological half-life, and the like. Such moieties or modifications of variant TNF-α polypeptides may alternatively eliminate or attenuate any possible undesirable side effect of the protein and the like. Moieties capable of mediating such effects are disclosed, for example, in *Remington's Pharmaceutical Sciences,* 16th ed., Mack Publishing Co., Easton, Pa. (1980), incorporated by reference.

Another type of covalent modification of variant TNF-α comprises linking the variant TNF-α polypeptide to one of a variety of nonproteinaceous polymers, e.g., polyethylene glycol ("PEG"), polypropylene glycol, or polyoxyalkylenes, in the manner set forth in U.S. Pat. No. 4,640,835; 4,496,689; 4,301,144; 4,670,417; 4,791,192 or 4,179,337, incorporated by reference. These nonproteinaceous polymers may also be used to enhance the variant TNF-α's ability to disrupt receptor binding, and/or in vivo stability. In another preferred embodiment, cysteines are designed into variant or wild type TNF-α in order to incorporate (a) labeling sites for characterization and (b) incorporate PEGylation sites. For example, labels that may be used are well known in the art and include but are not limited to biotin, tag and fluorescent labels (e.g. fluorescein). These labels may be used in various assays as are also well known in the art to achieve characterization. A variety of coupling chemistries may be used to achieve PEGylation, as is well known in the art. Examples include but are not limited to, the technologies of Shearwater and Enzon, which allow modification at primary amines, including but not limited to, lysine groups and the N-terminus. See, Kinstler et al, Advanced Drug Deliveries Reviews, 54, 477-485 (2002) and M J Roberts et al, Advanced Drug Delivery Reviews, 54, 459-476 (2002), both hereby incorporated by reference.

Optimal sites for modification can be chosen using a variety of criteria, including but not limited to, visual inspection, structural analysis, sequence analysis and molecular simulation. For example, as shown in FIG. 18, the fractional accessibility (surface_aa) of individual residues was analyzed to identify mutational sites that will not disrupt the monomer structure. Then the minimum distance (mindistance) from each side chain of a monomer to another subunit was calculated to ensure that chemical modification will not disrupt trimerization. It is possible that receptor binding disruption may occur and may be beneficial to the activity of the TNF variants of this invention. See also FIGS. 31-39.

In a preferred embodiment, the optimal chemical modification sites for the TNF-α variants of the present invention, include but are not limited to:

| | | <surface> | <min distance> | <combined> | | | <surface> | <min distance> | <combined> |
|---|---|---|---|---|---|---|---|---|---|
| GLU | 23 | 0.9 | 0.9 | 0.8 | GLY | 108 | 0.8 | 0.4 | 0.3 |
| GLN | 21 | 0.8 | 0.9 | 0.7 | GLN | 27 | 0.4 | 0.9 | 0.3 |
| ASP | 45 | 0.7 | 1.0 | 0.7 | GLU | 107 | 0.7 | 0.4 | 0.3 |
| ASP | 31 | 0.8 | 0.6 | 0.5 | ASP | 10 | 0.7 | 0.4 | 0.3 |
| ARG | 44 | 0.6 | 0.9 | 0.5 | SER | 86 | 0.6 | 0.5 | 0.3 |
| GLN | 25 | 0.5 | 1.0 | 0.5 | ALA | 145 | 0.8 | 0.4 | 0.3 |
| GLN | 88 | 0.7 | 0.7 | 0.4 | LYS | 128 | 0.6 | 0.4 | 0.3 |
| GLY | 24 | 0.5 | 0.9 | 0.4 | ASN | 46 | 0.3 | 0.9 | 0.3 |
| ASP | 140 | 0.6 | 0.7 | 0.4 | LYS | 90 | 0.5 | 0.5 | 0.3 |
| GLU | 42 | 0.5 | 0.8 | 0.4 | TYR | 87 | 0.6 | 0.4 | 0.3 |
| GLU | 110 | 0.8 | 0.4 | 0.4 | | | | | |

In a more preferred embodiment, the optimal chemical modification sites are 21, 23, 31 and 45, taken alone or in any combination. In an even more preferred embodiment, a TNF-α variant of the present invention include the R31c mutation. For example, TNF-α variant A145R/I97T was evaluated with and without a PEG-10 moiety (which was coupled to R31C).

Optionally, various excipients may be used to catalyze TNF exchange and heterotrimer formation. Other modifications, such as covalent additions, may promote or inhibit exchange, thereby affecting the specificity of the mechanism. The TNF hetero-trimer of the present invention becomes more labile when incubated in the presence of various detergents, lipids or the small molecule suramin. Thus, use of these excipients may greatly enhance the rate of heterotrimer formation. Covalent addition of molecules acting in a similar way may also promote exchange with transmembrane ligand.

Suitable excipients include pharmaceutically acceptable detergents or surfactants (ionic, non-ionic, cationic and anionic), lipids, mixed lipid vesicles, or small molecules, including long chain hydrocarbons (straight or branched, substituted or non-substituted, cis-trans saturated or unsaturated) that promote TNF exchange. For example, excipients that are useful in the present invention include (but are not limited to): CHAPS, Deoxycholate, Tween-20, Tween-80, Igepal, SDS, Triton X-100, and Triton X-114, steroidal or bile salts containing detergents (CHAPS), nonionic alkyl ethoxylate derived detergents (e.g., Triton and Tween), ionic detergents (SDS), and steroidal detergents (Deoxycholate). For example, TNF variant A145R/I97T blocks transmembrane TNF-induced signaling activity. The steroidal or bile salt containing detergents are preferably used at concentrations above CMC. However, detergents with hydrocarbon tails retain catalytic activity over a much broader concentration range. Certain detergents, especially non-ionic detergents may be used to promote exchange at or below their CMC. The excipients described above are equally useful as excipients in a pharmaceutical formulation of the TNF-α variants of the present invention.

In another preferred embodiment, portions of either the N- or C-termini of the wild type TNF-α monomer are deleted while still allowing the TNF-α molecule to fold properly. In addition, these modified TNF-α proteins would lack receptor binding ability, and could optionally interact with other wild type TNF alpha molecules or modified TNF-α proteins to form trimers as described above. More specifically, removal or deletion of from about 1 to about 55 amino acids from either the N or C termini, or both, are preferred. A more preferred embodiment includes deletions of N-termini beyond residue 10 and more preferably, deletion of the first 47 N-terminal amino acids. The deletion of C-terminal leucine is an alternative embodiment. In another preferred embodiment, the wild type TNF-α or variants generated by the invention may be circularly permuted. All natural proteins have an amino acid sequence beginning with an N-terminus and ending with a C-terminus. The N- and C-termini may be joined to create a cyclized or circularly permutated TNF-α proteins while retaining or improving biological properties (e.g., such as enhanced stability and activity) as compared to the wild-type protein. In the case of a TNF-α protein, a novel set of N- and C-termini are created at amino acid positions normally internal to the protein's primary structure, and the original N- and C-termini are joined via a peptide linker consisting of from 0 to 30 amino acids in length (in some cases, some of the amino acids located near the original termini are removed to accommodate the linker design). In a preferred embodiment, the novel N- and C-termini are located in a non-regular secondary structural element, such as a loop or turn, such that the stability and activity of the novel protein are similar to those of the original protein. The circularly permuted TNF-α protein may be further PEGylated or glycosylated. In a further preferred embodiment PDA® technology may be used to further optimize the TNF-α variant, particularly in the regions created by circular permutation. These include the novel N- and C-termini, as well as the original termini and linker peptide.

Various techniques may be used to permutate proteins. See U.S. Pat. No. 5,981,200; Maki K, Iwakura M., Seikagaku. 2001 Jan.; 73(1): 42-6; Pan T., Methods Enzymol. 2000; 317:313-30; Heinemann U, Hahn M., Prog Biophys Mol. Biol. 1995; 64(2-3): 121-43; Harris M E, Pace N R, Mol Biol Rep. 1995-96; 22(2-3):115-23; Pan T, Uhlenbeck O C., 1993 Mar. 30; 125(2): 111-4; Nardulli A M, Shapiro D J. 1993 Winter; 3(4):247-55, EP 1098257 A2; WO 02/22149; WO 01/51629; WO 99/51632; Hennecke, et al., 1999, J. Mol. Biol., 286, 1197-1215; Goldenberg et al J. Mol. Biol. 165, 407-413 (1983); Luger et al, Science, 243, 206-210 (1989); and Zhang et al., Protein Sci 5, 1290-1300 (1996); all hereby incorporated by reference. In addition, a completely cyclic TNF-α may be generated, wherein the protein contains no termini. This is accomplished utilizing intein technology. Thus, peptides can be cyclized and in particular inteins may be utilized to accomplish the cyclization.

Variant TNF-α polypeptides of the present invention may also be modified in a way to form chimeric molecules comprising a variant TNF-α polypeptide fused to another, heterologous polypeptide or amino acid sequence. In one embodiment, such a chimeric molecule comprises a fusion of a variant TNF-α polypeptide with a tag polypeptide which provides an epitope to which an anti-tag antibody can selectively bind. The epitope tag is generally placed at the amino- or carboxyl-terminus of the variant TNF-α polypeptide. The presence of such epitope-tagged forms of a variant TNF-α polypeptide can be detected using an antibody against the tag polypeptide. Also, provision of the epitope tag enables the variant TNF-α polypeptide to be readily purified by affinity purification using an anti-tag antibody or another type of affinity matrix that binds to the epitope tag. In an alternative embodiment, the chimeric molecule may comprise a fusion of a variant TNF-α polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol. 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology 6:1204-1210 (1988)]; the KT3 epitope peptide [Martin et al., Science 255:192-194 (1992)]; tubulin epitope peptide [Skinner et al., J. Biol. Chem. 266: 15163-15166 (1991)]; and the T7 gene 10 protein peptide tag [Lutz-Freyermuth et al., Proc. Natl. Acad. Sci. U.S.A. 87:6393-6397 (1990)], all incorporated by reference.

In a preferred embodiment, the variant TNF-α protein is purified or isolated after expression. Variant TNF-α proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the variant TNF-α protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, NY (1982), incorporated by reference. The degree of purification necessary will vary depending on the use of the variant TNF-α protein. In some instances no purification will be necessary. [01] The class of Dominant-Negative (DN) TNF compounds is just one example of molecules that can be envisioned to selectively inhibit soluble TNF while sparing the activity of transmembrane TNF. In addition, other classes of inhibitor can be created and/or identified by screening. For example, a soluble TNF-selective antibody can be created a number of ways. Structural prediction tools can be used to identify antibody-binding regions unique to soluble TNF that are masked or sterically blocked in transmembrane TNF. Mice or other animals could then be immunized with peptides or protein fragments or fusion proteins from these TNF domain(s) that are closest to the cell membrane when TNF is in its transmembrane form. Antibodies raised specifically against these regions, because of steric hindrance, would be unlikely to bind to and inactivate transmembrane TNF. As an alternate approach, the common surface-exposed surfaces of TNF distal to the cell membrane could be blocked (chemically, such as by pegylation, or with binding or fusion proteins) before immunization. Antibodies raised with these antigens would thus be more likely to bind to the TNF surface closest to the cell membrane. These approaches could be combined through mixed immunization and boost. For example, antibodies raised to normal native soluble TNF in the primary immunization could be boosted with peptide or protein fragments from soluble TNF that are not exposed in membrane-bound TNF. As another example, peptides or small molecules can be identified that bind only to soluble TNF. As above, structural prediction tools can be used to identify surface regions unique to soluble TNF. Small molecules or peptides binding to these regions could be identified through modeling approaches, or by screening for compounds that bind specifically to soluble TNF but not transmembrane TNF. Even without specific immunization approaches, inhibitors could be screened for soluble vs. transmembrane selectivity using two assays, one specific for soluble TNF activity (e.g., caspase activation by recombinant soluble human TNF), and one specific for transmembrane TNF activity (e.g., caspase activation by membrane-fused transmembrane TNF lacking the TNF Convertase (TACE) protease cleavage site, or blocked from release by a TACE inhibitor). Finally, even without specifically screening for soluble TNF selectivity in binding assays or cell assays, antibodies or small molecules could be screened in animal models of infection vs. efficacy to determine if a given compound had the desired safety (e.g., lack of suppression of host resistance to infection due to sparing of transmembrane TNF activity) vs. efficacy (e.g., anti-inflammatory effect in arthritis or other disease models due to inhibition of soluble TNF activity).

In addition, the invention provides methods of screening candidate agents for selective inhibitors (e.g. inhibition of soluble TNF-α activity while substantially maintaining transmembrane TNF-α activity). In general, this is done in a variety of ways as is known in the art, and can include a first assay to determine whether the candidate agent binds to soluble TNF-α and transmembrane TNF-α, and then determining the effect on biological activity. Alternatively, just activity assays can be done. In general, a candidate agent (usually a library of candidate agents) are contacted with a soluble TNF-α protein and activity is assayed, and similarly with the transmembrane TNF-α protein (usually as part of a cell).

A wide variety of suitable assay formats will be apparent by those in the art. In a preferred embodiment of the methods herein, one member of the assay, e.g. the candidate agent and the wild-type TNF-α (either soluble or transmembrane), is non-diffusably bound to an insoluble support having isolated sample receiving areas (e.g. a microtiter plate, an array, etc.; alternatively bead formats such as are used in high throughput screening using FACS can be used). The insoluble support may be made of any composition to which the protein or the candidate agent can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding the protein or the candidate agent is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or candidate agent, excess unbound material is removed by washing. The sample receiving areas may then be blocked through incubation with bovine serum albumin (BSA), casein or other innocuous protein or other moiety.

In a preferred embodiment, the protein is bound to the support, and a candidate bioactive agent is added to the assay. Alternatively, the candidate agent is bound to the support and the protein is added.

In some embodiments, one of the members of the assay (usually the nonbound component) can be labeled (e.g. optical dyes such as fluorophores and chromophores, enzymes, magnetic particles, radioisotopes, etc.), to detect binding after washing unbound reagent. Activity assays are described herein, including but not limited to, caspase assays, TNF-α cytotoxicity assays, DNA binding assays; transcription assays (using reporter constructs; see Stavridi, supra); size exclusion chromatography assays and radiolabeling/immuno-precipitation; see Corcoran et al., supra); and stability assays (including the use of circular dichroism (CD) assays and equilibrium studies; see Mateu, supra); all of which are incorporated by reference.

"Candidate agent" or "candidate drug" as used herein describes any molecule, e.g., proteins including biotherapeutics including antibodies and enzymes, small organic molecules including known drugs and drug candidates, polysaccharides, fatty acids, vaccines, nucleic acids, etc. that can be screened for activity as outlined herein. Candidate agents are evaluated in the present invention for discovering potential therapeutic agents that affect RR activity and therefore potential disease states, for elucidating toxic effects of agents (e.g. environmental pollutants including industrial chemicals, pesticides, herbicides, etc.), drugs and drug candidates, food additives, cosmetics, etc., as well as for elucidating new pathways associated with agents (e.g. research into the side effects of drugs, etc.).

Candidate agents encompass numerous chemical classes. In one embodiment, the candidate agent is an organic molecule, preferably small organic compounds having a molecular weight of more than 100 and less than about 2,500 daltons. Particularly preferred are small organic compounds having a molecular weight of more than 100 and less than about 2,000 daltons, more preferably less than about 1500 daltons, more preferably less than about 1000 daltons, more preferably less than 500 daltons. Candidate agents comprise functional groups necessary for structural interaction with proteins, particularly hydrogen bonding, and typically include at least one of an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

"Known drugs" or "known drug agents" or "already-approved drugs" refers to agents (i.e., chemical entities or biological factors) that have been approved for therapeutic use as drugs in human beings or animals in the United States or other jurisdictions. In the context of the present invention, the term "already-approved drug" means a drug having approval for an indication distinct from an indication being tested for by use of the methods disclosed herein. Using psoriasis and fluoxetine as an example, the methods of the present invention allow one to test fluoxetine, a drug approved by the FDA (and other jurisdictions) for the treatment of depression, for effects on biomarkers of psoriasis (e.g., keratinocyte proliferation or keratin synthesis); treating psoriasis with fluoxetine is an indication not approved by FDA or other jurisdictions. In this manner, one can find new uses (in this example, anti-psoriatic effects) for an already-approved drug (in this example, fluoxetine).

Candidate agents are obtained from a wide variety of sources including libraries of synthetic or natural compounds. For example, numerous means are available for random and directed synthesis of a wide variety of organic compounds and biomolecules, including expression and/or synthesis of randomized oligonucleotides and peptides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins as described herein.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate agents are antibodies, a class of proteins. The term "antibody" includes full-length as well antibody fragments, as are known in the art, including Fab Fab2, single chain antibodies (Fv for example), chimeric antibodies, humanized and human antibodies, etc., either produced by the modification of whole antibodies or those synthesized de novo using recombinant DNA technologies, and derivatives thereof.

In a preferred embodiment, the candidate bioactive agents are nucleic acids, particularly those with alternative backbones or bases, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110: 4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235, 033 and 5,034,506, and Chapters 6 and 7, ASC Symposium Series 580, "Carbohydrate Modifications in Antisense Research", Ed. Y. S. Sanghui and P. Dan Cook, and peptide nucleic acids. Nucleic acids containing one or more carbocyclic sugars are also included within the definition of nucleic acids (see Jenkins, et al., Chem. Soc. Rev., (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, 4-acetylcytosine, 8-hydroxy-N-6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine etc.

As described above generally for proteins, nucleic acid candidate bioactive agents may be naturally occurring nucleic acids, random and/or synthetic nucleic acids. For example, digests of procaryotic or eucaryotic genomes may be used as is outlined above for proteins. In addition, RNA is are included herein.

Once made, the variant TNF-α proteins and nucleic acids of the invention find use in a number of applications. In a preferred embodiment, the variant TNF-α proteins are administered to a patient to treat a TNF-α related disorder. By "TNF-α related disorder" or "TNF-α responsive disorder" or "condition" herein is meant a disorder that may be ameliorated by the administration of a pharmaceutical composition comprising a variant TNF-α protein, including, but not limited to, inflammatory and immunological disorders. The variant TNF-α is a major effector and regulatory cytokine with a pleiotropic role in the pathogenesis of immune-regulated diseases. In addition, the variant TNF-α plays a role in inflammation related conditions. In a preferred embodiment, the variant TNF-α protein is used to treat spondyloarthritis, rheumatoid arthritis, inflammatory bowel diseases, sepsis and septic shock, Crohn's Disease, psoriasis, graft versus host disease (GVHD) and hematologic malignancies, such as multiple myeloma (MM), myelodysplastic syndrome (MDS) and acute myelogenous leukemia (AML), cancer and the inflammation associated with tumors, peripheral nerve injury or demyelinating diseases, and Alzheimers disease and Parkinson's disease. See, for example, Tsimberidou et al., Expert Rev Anticancer Ther 2002 June; 2(3):277-86, incorporated by reference. It may also be used to treat multiple schlerosis, lupus, diabetes and insulin insensitivity. Inflammatory bowel disease ("IBD") is the term generally applied to two diseases, namely ulcerative colitis and Crohn's disease. Ulcerative colitis is a chronic inflammatory disease of unknown etiology afflicting only the large bowel and, except when very severe, limited to the bowel mucosa. The course of the disease may be continuous or relapsing, mild or severe. It is curable by total colostomy which may be needed for acute severe disease or chronic unremitting disease. Crohn's disease is also a chronic inflammatory disease of unknown etiology but, unlike ulcerative colitis, it can affect any part of the bowel. Although lesions may start superficially, the inflammatory process extends through the bowel wall to the draining lymph nodes. As with ulcerative colitis, the course of the disease may be continuous or relapsing, mild or severe but, unlike ulcerative colitis, it is not curable by resection of the involved segment of bowel. Most patients with Crohn's disease come to surgery at some time, but subsequent relapse is common and continuous medical treatment is usual. Remicade® (inflixmab) is the commercially available treatment for Crohn's disease. Remicade® is a chimeric monoclonal antibody that binds to TNF-α. The use of the TNF-α variants of the present invention may also be used to treat the conditions associated with IBD or Crohn's Disease.

"Sepsis" is herein defined to mean a disease resulting from gram positive or gram negative bacterial infection, the latter primarily due to the bacterial endotoxin, lipopolysaccharide (LPS). It can be induced by at least the six major gram-negative bacilli and these are *Pseudomonas aeruginosa, Escherichia coli, Proteus, Klebsiella, Enterobacter* and *Serratia*. Septic shock is a condition which may be associated with Gram positive infections, such as those due to pneumococci and streptococci, or with Gram negative infections, such as those due to *Escherichia coli, Klebsiella*-Enterobacter, *Pseudomonas*, and *Serratia*. In the case of the Gram-negative organisms the shock syndrome is not due to bloodstream invasion with bacteria per se but is related to release of endotoxin, the LPS moiety of the organisms' cell walls, into the circulation. Septic shock is characterized by inadequate tissue perfusion and circulatory insufficiency, leading to insufficient oxygen supply to tissues, hypotension, tachycardia, tachypnea, fever and oliguria. Septic shock occurs because bacterial products, principally LPS, react with cell membranes and components of the coagulation, complement, fibrinolytic, bradykinin and immune systems to activate coagulation, injure cells and alter blood flow, especially in the microvasculature. Microorganisms frequently activate the classic complement pathway, and endotoxin activates the alternate pathway.

The TNF-α variants of the present invention effectively antagonize the effects of wild type TNF-α -induced cytotoxicity and interfere with the conversion of TNF into a mature TNF molecule (e.g. the trimer form of TNF). Thus, administration of the TNF variants can ameliorate or eliminate the effects of sepsis or septic shock, as well as inhibit the pathways associated with sepsis or septic shock. Administration may be therapeutic or prophylactic. The TNF-α variants of the present invention effectively antagonize the effects of wild type TNF-α-induced cytotoxicity in cell based assays and animal models of peripheral nerve injury and axonal demyelination/degeneration to reduce the inflammatory component of the injury or demyelinating insult. This is believed to critically contribute to the neuropathological and behavioral sequelae and influence the pathogenesis of painful neuropathies.

Severe nerve injury induces activation of Matrix Metallo Proteinases (MMPs), including TACE, the TNF-α-converting enzyme, resulting in elevated levels of TNF-α protein at an early time point in the cascade of events that leads up to Wallerian nerve degeneration and increased pain sensation (hyperalgesia). The TNF-α variants of the present invention antagonize the activity of these elevated levels of TNF-α at the site of peripheral nerve injury with the intent of reducing macrophage recruitment from the periphery without negatively affecting remyelination. Thus, reduction of local TNF-induced inflammation with these TNF-α variants would represent a therapeutic strategy in the treatment of the inflammatory demyelination and axonal degeneration in peripheral nerve injury as well as the chronic hyperalgesia characteristic of neuropathic pain states that often results from such peripheral nerve injuries.

Intraneural administration of exogenous TNF-α produces inflammatory vascular changes within the lining of peripheral nerves (endoneurium) together with demyelination and axonal degeneration (Redford et al 1995). After nerve transection, TNF-positive macrophages can be found within degenerating fibers and are believed to be involved in myelin degradation after axotomy (Stoll et al 1993). Furthermore, peripheral nerve glia (Schwann cells) and endothelial cells produce extraordinary amounts of TNF-α at the site of nerve injury (Wagner et al 1996) and intraperitoneal application of anti-TNF antibody significantly reduces the degree of inflammatory demyelination strongly implicating a pathogenic role for TNF-α in nerve demyelination and degeneration (Stoll et al., 1993). Thus, administration of an effective amount of the TNF-α variants of the present invention may be used to treat these peripheral nerve injury or demyelinating conditions, as well as Alzheimers disease and Parkinson's disease. In a preferred embodiment, a therapeutically effective dose of a variant TNF-α protein is administered to a patient in need of treatment. By "therapeutically effective dose" herein is meant a dose that produces the effects for which it is administered. The exact dose will depend on the purpose of the treatment, and will be ascertainable by one skilled in the art using known techniques. In a preferred embodiment, dosages of about 5 μg/kg are used, administered either intravenously or subcutaneously. As is known in the art, adjustments for variant TNF-α protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human. The term "treatment" in the instant invention is meant to include therapeutic treatment, as well as prophylactic, or suppressive measures for the disease or disorder. Thus, for example, successful administration of a variant TNF-α protein prior to onset of the disease results in "treatment" of the disease. As another example, successful administration of a variant TNF-α protein after clinical manifestation of the disease to combat the symptoms of the disease comprises "treatment" of the disease. "Treatment" also encompasses administration of a variant TNF-α protein after the appearance of the disease in order to eradicate the disease. Successful administration of an agent after onset and after clinical symptoms have developed, with possible abatement of clinical symptoms and perhaps amelioration of the disease, comprises "treatment" of the disease. Those "in need of treatment" include mammals already having the disease or disorder, as well as those prone to having the disease or disorder, including those in which the disease or disorder is to be prevented.

In another embodiment, a therapeutically effective dose of a variant TNF-α protein, a variant TNF-α gene, or a variant TNF-α antibody is administered to a patient having a disease involving inappropriate expression of TNF-α. A "disease involving inappropriate expression of at TNF-α" within the scope of the present invention is meant to include diseases or disorders characterized by aberrant TNF-α, either by alterations in the amount of TNF-α present or due to the presence of mutant TNF-α. An overabundance may be due to any cause, including, but not limited to, overexpression at the molecular level, prolonged or accumulated appearance at the site of action, or increased activity of TNF-α relative to normal. Included within this definition are diseases or disorders characterized by a reduction of TNF-α. This reduction may be due to any cause, including, but not limited to, reduced expression at the molecular level, shortened or reduced appearance at the site of action, mutant forms of TNF-α, or decreased activity of TNF-α relative to normal. Such an overabundance or reduction of TNF-α can be measured relative to normal expression, appearance, or activity of TNF-α according to, but not limited to, the assays described and referenced herein.

The administration of the variant TNF-α proteins of the present invention, preferably in the form of a sterile aqueous solution, may be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds, inflammation, etc., the variant TNF-α protein may be directly applied as a solution, salve, cream or spray. The TNF-α molecules of the present may also be delivered by bacterial or fungal expression into the human system (e.g., WO 04046346 A2, hereby incorporated by reference). Depending upon the manner of introduction, the pharmaceutical composition may be formulated in a variety of ways. The concentration of the therapeutically active variant TNF-α protein in the formulation may vary from about 0.1 to 100 weight %. In another preferred embodiment, the concentration of the variant TNF-α protein is in the range of 0.003 to 1.0 molar, with dosages from 0.03, 0.05, 0.1, 0.2, and 0.3 millimoles per kilogram of body weight being preferred.

The pharmaceutical compositions of the present invention comprise a variant TNF-α protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations. In a further embodiment, the variant TNF-α proteins are added in a micellular formulation; see U.S. Pat. No. 5,833,948, hereby incorporated by reference. Alternatively, liposomes may be employed with the TNF-α proteins to effectively deliver the protein. Combinations of pharmaceutical compositions may be administered. Moreover, the TNF-α compositions of the present invention may be administered in combination with other therapeutics, either substantially simultaneously or co-administered, or serially, as the need may be.

In one embodiment provided herein, antibodies, including but not limited to monoclonal and polyclonal antibodies, are raised against variant TNF-α proteins using methods known in the art. In a preferred embodiment, these anti-variant TNF-α antibodies are used for immunotherapy. Thus, methods of immunotherapy are provided. By "immunotherapy" is meant treatment of an TNF-α related disorders with an antibody raised against a variant TNF-α protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with a variant TNF-α protein antigen to which antibodies are raised. As appreciated by one of ordinary skill in the art, the variant TNF-α protein antigen may be provided by injecting a variant TNF-α polypeptide against which antibodies are desired to be raised into a recipient, or contacting the recipient with a variant TNF-α protein encoding nucleic acid, capable of expressing the variant TNF-α protein antigen, under conditions for expression of the variant TNF-α protein antigen.

In another preferred embodiment, a therapeutic compound is conjugated to an antibody, preferably an anti-variant TNF-α protein antibody. The therapeutic compound may be a cytotoxic agent. In this method, targeting the cytotoxic agent to tumor tissue or cells, results in a reduction in the number of afflicted cells, thereby reducing symptoms associated with cancer, and variant TNF-α protein related disorders. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, variant TNF-α proteins are administered as therapeutic agents, and can be formulated as outlined above. Similarly, variant TNF-α genes (including both the full-length sequence, partial sequences, or regulatory sequences of the variant TNF-α coding regions) may be administered in gene therapy applications, as is known in the art. These variant TNF-α genes can include antisense applications, either as gene therapy (i.e. for incorporation into the genome) or as antisense compositions, as will be appreciated by those in the art.

In a preferred embodiment, the nucleic acid encoding the variant TNF-α proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. [Zamecnik et al., Proc. Natl. Acad. Sci. U.S.A. 83:4143-4146 (1986), incorporated by reference]. The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection [Dzau et al., Trends in Biotechnology 11:205-210 (1993), incorporated by reference]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429-4432 (1987); and Wagner et al., Proc. Natl. Acad. Sci. U.S.A. 87:3410-3414 (1990), both incorporated by reference. For review of gene marking and gene therapy protocols see Anderson et al., Science 256:808-813 (1992), incorporated by reference.

In a preferred embodiment, variant TNF-α genes are administered as DNA vaccines, either single genes or combinations of variant TNF-α genes. Naked DNA vaccines are generally known in the art. Brower, Nature Biotechnology, 16:1304-1305 (1998). Methods for the use of genes as DNA vaccines are well known to one of ordinary skill in the art, and include placing a variant TNF-α gene or portion of a variant TNF-α gene under the control of a promoter for expression in a patient in need of treatment. The variant TNF-α gene used for DNA vaccines can encode full-length variant TNF-α proteins, but more preferably encodes portions of the variant TNF-α proteins including peptides derived from the variant TNF-α protein. In a preferred embodiment a patient is immunized with a DNA vaccine comprising a plurality of nucleotide sequences derived from a variant TNF-α gene. Similarly, it is possible to immunize a patient with a plurality of variant TNF-α genes or portions thereof as defined herein. Without being bound by theory, expression of the polypeptide encoded by the DNA vaccine, cytotoxic T-cells, helper T-cells and antibodies are induced which recognize and destroy or eliminate cells expressing TNF-α proteins.

In a preferred embodiment, the DNA vaccines include a gene encoding an adjuvant molecule with the DNA vaccine. Such adjuvant molecules include cytokines that increase the immunogenic response to the variant TNF-α polypeptide encoded by the DNA vaccine. Additional or alternative adjuvants are known to those of ordinary skill in the art and find use in the invention.

All references cited herein, including patents, patent applications (provisional, utility and PCT), and publications are incorporated by reference.

EXAMPLES

Example 1

Protocol for TNF-α Library Expression, Purification, and Activity Assays for TNF-α Variants Methods: 1) Overnight culture preparation: Competent Tuner(DE3)pLysS cells in 96 well-PCR plates were transformed with 1 ul of TNF-α library DNAs and spread on LB agar plates with 34 mg/ml chloramphenicol and 100 mg/ml ampicillin. After an overnight growth at 37 degrees C., a colony was picked from each plate in 1.5 ml of CG media with 34 mg/ml chloramphenicol and 100 mg/ml ampicillin kept in 96 deep well block. The block was shaken at 250 rpm at 37 degrees C. overnight. 2) Expression: Colonies were picked from the plate into 5 ml CG media (34 mg/ml chloramphenicol and 100 mg/ml ampicillin) in 24-well block and grown at 37 degrees C. at 250 rpm until OD600 0.6 were reached, at which time IPTG was added to each well to 1 mM concentration. The culture was grown 4 extra hours. 3) Lysis: The 24-well block was centrifuged at 3000 rpm for 10 minutes. The pellets were resuspended in 700 ul of lysis buffer (50 mM $NaH2PO_4$, 300 mM NaCl, 10 mM imidazole). After freezing at −80 degrees C. for 20 minutes and thawing at 37 degrees C. twice, $MgCl_2$ was added to 10 mM, and DNase 1 to 75 mg/ml. The mixture was incubated at 37 degrees C. for 30 minutes. 4) Ni NTA column purification: Purification was carried out following Qiagen Ni NTA spin column purification protocol for native condition. The purified protein was dialyzed against 1×PBS for 1 hour at 4 degrees C. four times. Dialyzed protein was filter sterilized, using Millipore multiscreenGV filter plate to allow the addition of protein to the sterile mammalian cell culture assay later on. 5) Quantification: Purified protein was quantified by SDS PAGE, followed by Coomassie stain, and by Kodak® digital image densitometry. 6) TNF-α Activity Assay assays: The activity of variant TNF-α protein samples was tested using Vybrant Assay Kit and Caspase Assay kit. Sytox Green nucleic acid stain is used to detect TNF-induced cell permeability in Actinomycin-D sensitized cell line. Upon binding to cellular nucleic acids, the stain exhibits a large fluorescence enhancement, which is then measured. This stain is excluded from live cells but penetrates cells with compromised membranes.

The caspase assay is a fluorimetric assay, which can differentiate between apoptosis and necrosis in the cells. Cell extracts were made from cells treated to induce apoptosis. These extracts were supplemented with a fluorescently-conjugated caspase substrate (DEVD-R110) peptide. Activated caspase enzymes cleave the DEVD-R110 peptide to produce a fluorescent enhancement of R110. Therefore, R110 fluorescence is a direct measure of caspase activity, which is a direct measure of apoptosis.

A) Materials: Cell Line: WEHI Var-13 Cell line from ATCC; Media: RPMI Complete media with 10% FBS; Vybrant TNF Kit: Cat # V-23100; Molecular Probes (Kit contains SYTOX Green nucleic acid stain (500 mM solution) and Actinomycin D (1 mg/mL)); Caspase Assay Kit: Cat # 3 005 372; Roche (Kit contains substrate stock solution (500 uM) and incubation buffer); TNF-α Standard stock: 10 ug/mL stock of h-TNF-α from R & D; Unknown Samples: In house TNF-α library samples; 96-well Plates, 1 mL deep well and 250 m wells; Micro plate Reader.

B) Method: Plate WEHI164-13Var cells at 2.5×105 cells/mL in full RPMI medium, 24 hrs prior to the assay; (100 uL/well for the Sytox assay and 50 uL/well for the Caspase assay). On the day of the experiment, prepare assay media as follows: 1) Assay Media for Sytox Assay (1×): Prepare assay medium by diluting the concentrated Sytox Green stain and the concentrated actinomycin D solution 500-fold into RPMI, to a final concentration of 10 mM Sytox and 2 mg/mL actinomycin D; 10 mL complete RPMI medium; 20 mL SYTOX Green; 20 mL actinomycin D; 2) Prepare Assay Media for Caspase Assay (1×): 10 mL complete RPMI medium; 20 uL Actinomycin D (2 mg/mL final conc.); 3) Prepare Assay Media for samples: Sytox Assay (2×): 14 mL complete RPMI medium; 56 mL SYTOX Green Nuclei acid stain; 56 mL actinomycin D; 4) Prepare Assay Media: (2×): For samples: Caspase assay, 14 mL complete RPMI medium; 56 mL actinomycin D; 5) Set up and Run a Standard Curve Dilution: TNF-α Std. stock: 10 mg/mL; Dilute to 1 ug/mL: 10 mL stock+90 mL Assay medium.

| Stock (uL) | 1X Assay medium for Sytox and Caspase (mL) | Conc. in dilution plate | Final Conc. of TNF-α on cells |
| --- | --- | --- | --- |
| 10 uL of 1 mg | 990 | 10 ng/mL | 5 ng/mL |
| 5 uL of 1 mg | 995 | 5 ng/mL | 2.5 ng/mL |
| 200 uL of 5 ng | 300 | 2 ng/mL | 1 ng/mL |
| 100 uL of 5 ng | 400 | 1 ng/mL | 0.5 ng/mL |
| 100 uL of 5 ng | 900 | 500 pg/mL | 250 pg/mL |
| 200 uL of 500 pg | 300 | 200 pg/mL | 100 pg/mL |
| 100 uL of 500 pg | 400 | 100 pg/mL | 50 pg/mL |
| 50 uL of 500 pg | 450 | 50 pg/mL | 25 pg/mL |
| 20 uL of 500 pg | 480 | 20 pg/mL | 10 pg/mL |
| 10 uL of 500 pg | 490 | 10 pg/mL | 5 pg/mL |
| 0 uL | 500 | 0 pg/mL | 0 pg/mL |

For Unknown Samples: (Quantitated by Gel): TNF-α Library: Normalize all the samples to the same starting concentration (500 ng/mL) as follows: (Neat: 500 ng/mL: 100 mL; 1:10 of 500 ng=50 ng/mL: 20 mL neat+180 mL RPMI; 1:10 of 50 ng=5 ng/mL: 20 mL of 50 ng/mL+180 mL RPMI; 1:10 of 5 ng/mL=0.5 ng/mL: 20 mL of 0.5 ng/mL+180 mL RPMI). 6) For Sytox assay: On a separate dilution plate, add 60 mL of each diluted sample to 60 mL of 2× Sytox assay media. Transfer 100 mL of diluted samples to the cells cultured in 100 uL media. Incubate at 37 degrees C. for 6 hrs. Read the plate using a fluorescence microplate reader with filters appropriate for fluorescein (485 nm excitation filter and 530 nm emission filter). 7) For Caspase assay: On a separate dilution plate, add 35 mL of each diluted sample to 35 mL of 2× Caspase assay media. Transfer 50 mL of dil. Samples to the cells cultured in 50 mL media. Incubate at 37 degrees C. for 4 hours. After 4 hrs. add Caspase Substrate (100 mL/well) [Predilute substrate 1:10]. Incubate 2 more hrs. at 37 degrees C. Read (fluorescence).

C) Data Analysis: The fluorescence signal is directly proportional to the number of apoptotic cells. Plot fluorescence vs. TNF-α standard concentration to make a standard curve. Compare the fluorescence obtained from the highest point on the standard curve (5 ng/mL) to the fluorescence obtained from the unknown samples, to determine the percent activity of the samples. The data may be analyzed using a four-parameter fit program to determine the 50% effective concentration for TNF (EC50). Percent activity of unknown samples=(Fluor. Of unknown samples/fluor. of 5 ng/mL std. Point)×100.

Example 2

TNF-α Activity Assay to Screen for Agonists of Wild Type TNF-α Protein

Materials and Methods: 1) Plate cells for the TNF assay: WEHI plated at 2.5×105 Cells/ml (50 μl/well in a 96 well plate); 2) Prepare Assay Media (a. 1× Assay Medium [10 ml complete RPMI medium; 20 μl Actinomycin D]; b. 2× Assay Media [7 ml complete RPMI medium; 28 μl Actinomycin D]; 3) Dilute TNF-α Standards for Bioactivity Assay: Requires two standard Curves in duplicate as shown below: (In house TNF-α (lot #143-112) stock: 1.1; Dilute to 40 μg/mL: 36 μl stock+964 μl assay medium.)

| Stock (μl) | Assay medium (μl) | Conc. in dilution plate | Final Conc. of TNF-α in cells |
| --- | --- | --- | --- |
| 500 ul of 40 ug/ml | 500 | 20,000 ng/ml | 10,000 ng/ml |
| 500 ul of 20,000 ng/ml | 500 | 10,000 ng/ml | 5,000 ng/ml |
| 200 ul of 10,000 ng/ml | 800 | 2000 ng/ml | 1000 ng/ml |
| 500 ul of 2000 ng/ml | 500 | 1000 ng/ml | 500 ng/ml |
| 200 ul of 1000 ng/ml | 800 | 200 ng/ml | 100 ng/ml |
| 500 ul of 200 ng/ml | 500 | 100 ng/ml | 50 ng/ml |
| 200 ul of 100 ng/ml | 800 | 20 ng/ml | 10 ng/ml |
| 50 ul of 20 ng/ml | 950 | 1 ng/ml | 0.5 ng/ml |
| 200 ul of 1 ng/ml | 800 | 0.2 ng/ml | 0.1 ng/ml |
| 500 ul of 0.2 ng/ml | 500 | 0.1 ng/ml | 0.05 ng/ml |
| 500 ul of 0.1 ng/ml | 500 | 0.05 ng/ml | 0.025 ng/ml |
| 0 | 500 | 0 | 0 |

4) Treatment of Unknown Samples from TNF-α Library: Normalize all samples to the same starting concentration (200,000 ng/ml) by diluting samples as shown: (Neat: 200, 000 ng/ml: 200 μl; 1:10 of 200,000 ng/ml=20,000 ng/ml: 20 μl of neat+180 μl of RPMI; 1:10 of 20,000 ng/ml=2000 ng/ml: 20 μl of 1:10+180 μl RPMI; 1:10 of 2000 ng/ml=200 ng/ml: 20 μl of 1:100+180 μl RPMI; 1:10 of 200 ng/ml=20 ng/ml: 20 μl of 1:100+180 μl RPMI).

On a separate dilution plate for Caspase assay: Add 150 μl of each diluted sample to 150 μl of 2× caspase assay media. Incubate all the diluted samples and standard curve at 37° C. overnight. Next morning, transfer 50 μl of diluted samples to the cells with CM. After 4 hours prepare substrate, and then add 100 μl of substrate to the cells. Read fluorescence after 2 hours of incubation with substrate. The results are summarized in FIG. 8.

Example 3

TNF-α Antagonist Activity

Materials and Methods: 1) Plate cells for the assay: WEHI plated at 2.5×105 cells/ml (50 μl/well); 2) Prepare Assay Media: (1× Assay Medium; 40 ml complete RPMI medium;

80 μl Actinomycin D (2 μg/ml final concentration)); 3) Antagonist Activity of TNF-α mutants; 4) Preparation of assay medium+wild type TNF-α: (Wild type TNF-α is 1.1 mg/ml; 1 μg/ml: 1:1000; 1 μl of the stock in 1 ml of RPMI; 20 ng/ml: 1:50 of the 1 μg/ml; 800 μl in 40 ml of assay medium); 5) Dilution of TNF-α variants was done as shown below:

| Stock (μl) | Assay medium (μl) with 20 ng/ml of wild type TNF-α | Concentration in dilution plate | Final concentration of TNF-α in cells |
|---|---|---|---|
| K112D: 59 μl | 941 | 100,000 ng/ml | 50,000 ng/ml |
| Y115T: 77 μl | 923 | | |
| D143K: 32 μl | 968 | | |
| D143R: 34 μl | 966 | | |
| Y115I: 63 μl | 937 | | |
| D143E: 40 μl | 960 | | |
| A145R: 50 μl | 950 | | |
| A145K: 50 μl | 950 | | |
| A145E: 26 μl | 974 | | |
| E146K: 40 μl | 960 | | |
| E146R: 56 μl | 944 | | |
| 500 μl of 100,000 ng/ml | 500 | 50,000 ng/ml | 25,000 ng/ml |
| 500 μl of 50,000 ng/ml | 500 | 25,000 ng/ml | 12,500 ng/ml |
| 400 μl of 25,000 ng/ml | 600 | 10,000 ng/ml | 5000 ng/ml |
| 500 μl of 10,000 ng/ml | 500 | 5,000 ng/ml | 2,500 ng/ml |
| 200 μl of 5000 ng/ml | 800 | 1000 ng/ml | 500 ng/mL |
| 500 μl of 1000 ng/ml | 500 | 500 ng/ml | 50 ng/mL |
| 500 μl of the 500 ng/ml | 500 | 250 ng/ml | 125 ng/mL |
| 400 μl of 250 ng/ml | 600 | 100 ng/ml | 50 ng/mL |
| 100 μl of 100 ng/ml | 900 | 10 ng/ml | 5 ng/mL |
| 100 μl of 10 ng/ml | 900 | 1 ng/ml | 0.5 ng/mL |
| 0 | 0 | 0 | 0 |

6) Dilutions for Inhibition Assay: (Stocks to dilute TNF Receptor (TNF R) in 1× assay medium; Stock is 100 μg/ml; For 20 μg/ml: 1:5 dilution: 60 μl of 100 μg/ml of Stock+240 μl of 1× assay medium with wild type TNF-α;) Dilute TNF R assay medium containing 20 ng/ml of wild type TNF-α (final on the cell 10 ng/ml) as shown below:

| Stock (μl) | Assay medium (μl) with TNF-α | Concentration in dilution plate | Final Concentration in cells |
|---|---|---|---|
| 300 μl of 20 μg | 300 | 10,000 ng/ml | 5000 ng/ml |
| 200 μl of 10,000 ng | 300 | 4000 ng/ml | 2000 ng/ml |
| 250 μl of 4000 ng | 250 | 2000 ng/ml | 1000 ng/ml |
| 250 μl of 2000 ng | 250 | 1000 ng/ml | 500 ng/ml |
| 50 μl of 10,000 μg/ml | 950 | 500 ng/ml | 250 ng/ml |
| 200 μl of 500 ng/ml | 300 | 200 ng/ml | 100 ng/ml |
| 100 μl of 500 ng/ml | 400 | 100 ng/ml | 50 ng/ml |
| 100 μl of 500 ng/ml | 900 | 50 ng/ml | 25 ng/ml |
| 200 μl of 50 ng/ml | 300 | 20 ng/ml | 10 ng/ml |
| 100 μl 50 ng/ml | 400 | 10 ng/ml | 5 ng/ml |
| 50 μl 50 ng/ml | 450 | 5 ng/ml | 2.5 ng/ml |
| 0 | 250 | 0 | 0 |

All of the above dilutions were done 16 hours prior to adding to the cells. Then 120 μl of each diluted sample was incubated at 4° C., and 120 μl of each sample was incubated at 37° C. The next morning, 50 μl of each sample was added to the cells. The cells were incubated at 37° C. for 4 hours. After 4 hours of incubation, 100 μl of the caspase substrate was added to each well, followed by a 2 hour incubation at 37° C. Read fluorescence. The results are shown in FIGS. 9 and 10.

Example 4

TNF-α Antagonist Activity of Combinatorial TNF-α Variants

A) Materials and Method: 1) Plate cells for the assay: WEHI164-13Var cells plated at 7.5×105 cells/ml (50 μl/well), incubate at 37C overnight. 2) Prepare Assay Media: (10×, final concentration on cells will be 10 ng/mL); 7 ml full RPMI; 5 uL of 310 ug/mL wild type his-TNF [Lot#263-56]; 140 uL 1 mg/mL ActinomycinD; 3) Dilution of TNF-α variants was done as shown below, samples mixed three days prior to start of experiment:

| | Stock (uL) | RPMI | Conc. Before 10X | Conc. After 10X | Final Conc. on cells |
|---|---|---|---|---|---|
| 1 | E146K/N34V/V91E (lot 388-3) 1800 ug/mL: 38.6 | 961.4 | 69,520 | 63,200 ng/mL | 31,600 ng/mL |
| | Y115Q/I97T (380-32) 2000 ug/mL: 34.7 | 965.3 | | | |
| | Y115Q/I97R (380-32) 1400 ug/mL: 49.8 | 950.2 | | | |
| | Y115Q/Y87R (380-32) 1100 ug/mL: 63.3 | 936.7 | | | |
| | Y115Q/L57Y (380-32) 1100 ug/mL 63.3 | 936.7 | | | |
| | Y115Q/L57F (380-32) 1200 ug/mL 57.8 | 942.2 | | | |
| | A145R/L57F (388-3) 2000 ug/mL 34.7 | 965.3 | | | |
| | A145R/Y87H (378-96) 880 ug/mL 78.7 | 921.3 | | | |
| | Enbrel 25000 ug/mL | 997.3 | | | |
| | Buffer (PBS pH 8) 100 uL | 900 | | | |
| | TNF R (500 ug/mL) 70 uL | 430 | | | |
| 2 | 316 (158 for TNF R) ul of 63,200 ng/mL | 684 (342) | 22,000 | 20,000 ng/mL | 10,000 ng/mL |
| 3 | 316 (158 for TNF R) ul of 20000 ng/mL | 684 (342) | 6,952 | 6,320 ng/mL | 3,160 ng/mL |
| 4 | 316 (158 for TNF R) ul of 6,320 ng/mL | 684 (342) | 2200 | 2,000 ng/mL | 1000 ng/mL |
| 5 | 316 (158 for TNF R) ul of 2000 ng/mL | 684 (342) | 695.2 | 362 ng/mL | 316 ng/mL |
| 6 | 316 (158 for TNF R) ul of 362 ng/mL | 684 (342) | 220 | 200 ng/mL | 100 ng/mL |
| 7 | 316 (158 for TNF R) ul of 200 ng/mL | 684 (342) | 69.52 | 63.2 ng/mL | 31.6 ng/mL |
| 8 | 316 (158 for TNF R) ul of 63.2 ng/mL | 684 (342) | 22 | 20 ng/mL | 10 ng/mL |
| 9 | 316 (158 for TNF R) ul of 20 ng/mL | 684 (342) | 6.95 | 6.32 ng/mL | 3.16 ng/mL |
| 10 | 316 (158 for TNF R) ul of 6.32 ng/mL | 684 (342) | 2.2 | 2 ng/mL | 1 ng/mL |
| 11 | 316 (158 for TNF R) ul of 2 ng/mL | 684 (342) | 0.6952 | 0.632 ng/mL | 0.316 ng/mL |
| 12 | 0 | 684 (342) | 0 | 0 ng/mL | 0 |

Figure 21:
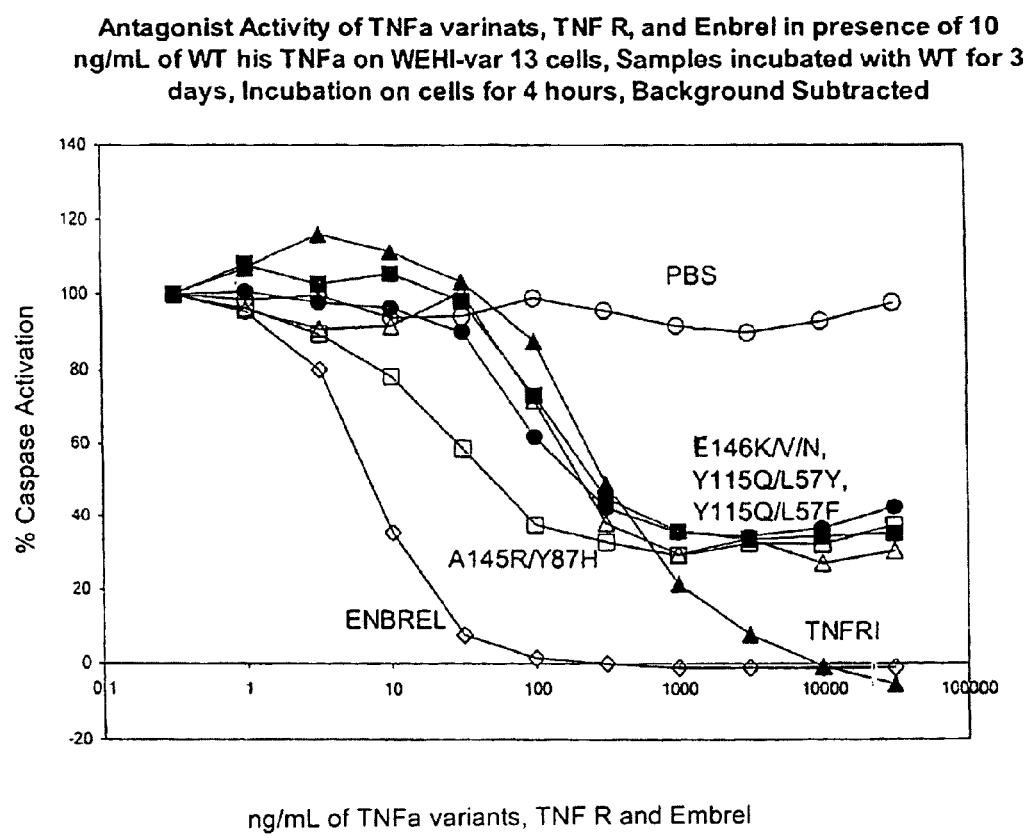
FIG. 21 is a chart showing antagonist activity of TNF-α variants.

After all dilutions were done add 68.4 (34.2 for TNF R) uL of 10× assay media containing WT his TNFa to each dilution well. Then the 96 well was placed in the incubator for 3 days. 50 ul of each sample were added to WEHI164-13Var cells for 4 hours. Upon completion of the incubation, add 100 ul of caspase substrate. Incubate for 1.5 hours. A R110 curve was also prepared by diluting the R110 standard 1:100 in RPMI followed by an 8-point half dilution. Then 100 ul of each dilution were added to a plate without cells, these dilutions are done right before adding the substrate to the cells. 100 ul of substrate was also added to R110 curve dilutions. Upon the completion of 1.5-hour incubation at 37 C, all samples were read using the Wallac fluorometer at 484/535 nm wavelengths. Results are shown in FIG. 21.

Example 5

Fixed Equilibrium Screening of Many TNF-α Variants

Prepare 1:10 fixed equilibrium ratios of TNF-α variants: Mix together 0.01 mg/mL wild type his-TNF [lot#263-56] with 0.1 mg/mL variant TNF-α in 50 uL reactions in phosphate-buffered saline (PBS). Prepare this mixture and incubate at 37C for three-four days. Plate cells for the assay: Human U937 cells plated at 1×106 cells/ml (50 μl/well), incubate at 37C overnight.

| Protein Name | Lot# | Conc. (mg/mL) | Volume Prot. (uL) | 0.33 mg/mL wt TNF (uL) | PBS |
|---|---|---|---|---|---|
| Y115Q/L57W | 380-32 | 1.3 | 3.85 | 1.5 | 44.65 |
| Y115M/D143N | 380-32 | 0.36 | 13.8 | 1.5 | 34.7 |
| Y115Q/Y87H | 380-32 | 1.1 | 4.55 | 1.5 | 44 |
| Y115Q/A145R | 380-32 | 0.53 | 9.4 | 1.5 | 39.1 |
| Y115Q/A145F | 380-32 | 2.0 | 2.5 | 1.5 | 46 |
| Y115Q/L57Y | 380-32 | 1.1 | 4.55 | 1.5 | 44 |
| Y115M/A145R | 380-32 | 0.74 | 6.8 | 1.5 | 41.7 |
| Y115M/E146K | 380-32 | 0.27 | 18.5 | 1.5 | 30 |
| Y115M/D143Q | 380-32 | 0.37 | 13.5 | 1.5 | 35 |
| Y115Q/L57F | 380-32 | 1.2 | 4.17 | 1.5 | 44.3 |
| A145R/I97R | 380-32 | 0.56 | 9 | 1.5 | 39.5 |
| A145R/Y87H | 380-32 | 1.6 | 3.13 | 1.5 | 45.4 |
| A145R/L75Q | 380-32 | 0.86 | 5.8 | 1.5 | 42.7 |
| A145R/L75K | 380-32 | 0.99 | 4.9 | 1.5 | 43.6 |
| Y115M/A145R | 380-32 | 0.23 | 21.7 | 1.5 | 27 |
| A145R/S86Q | 380-32 | 1.2 | 4.2 | 1.5 | 44.3 |
| E146K/V91E/N34E | 380-32 | 1.2 | 2.8 | 1.5 | 45.7 |
| A145R/S86R | 378-95 | 0.27 | 18.5 | 1.5 | 30 |
| A145R/I97T | 378-97 | 0.47 | 10.6 | 1.5 | 37.9 |
| A145R/L75E | 378-94 | 1.73 | 2.9 | 1.5 | 45.6 |
| Y115Q/S86R | 380-32 | 0.94 | 4.9 | 1.5 | 43.6 |
| Y115Q/Y87R | 380-32 | 1.1 | 4.6 | 1.5 | 43.9 |
| Y115Q/L75K | 380-32 | 0.75 | 6.7 | 1.5 | 41.8 |
| Y115Q/S86Q | 380-32 | 1.0 | 4.9 | 1.5 | 43.6 |
| Y115Q/E146K | 380-32 | 0.38 | 13.1 | 1.5 | 35.4 |
| Y115Q/L75Q | 380-32 | 0.58 | 8.6 | 1.5 | 39.9 |
| Y115Q/I97T | 380-32 | 2.0 | 2.5 | 1.5 | 46 |
| Y115Q/D143N | 380-32 | 0.3 | 16.7 | 1.5 | 31.8 |
| Y115Q/L75E | 380-32 | 0.62 | 8.1 | 1.5 | 40.4 |
| Y115Q/I97R | 380-32 | 1.4 | 3.6 | 1.5 | 44.9 |
| A145R/L57F | 388-3 | 2 | 2.5 | 1.5 | 46 |

Figure 22:
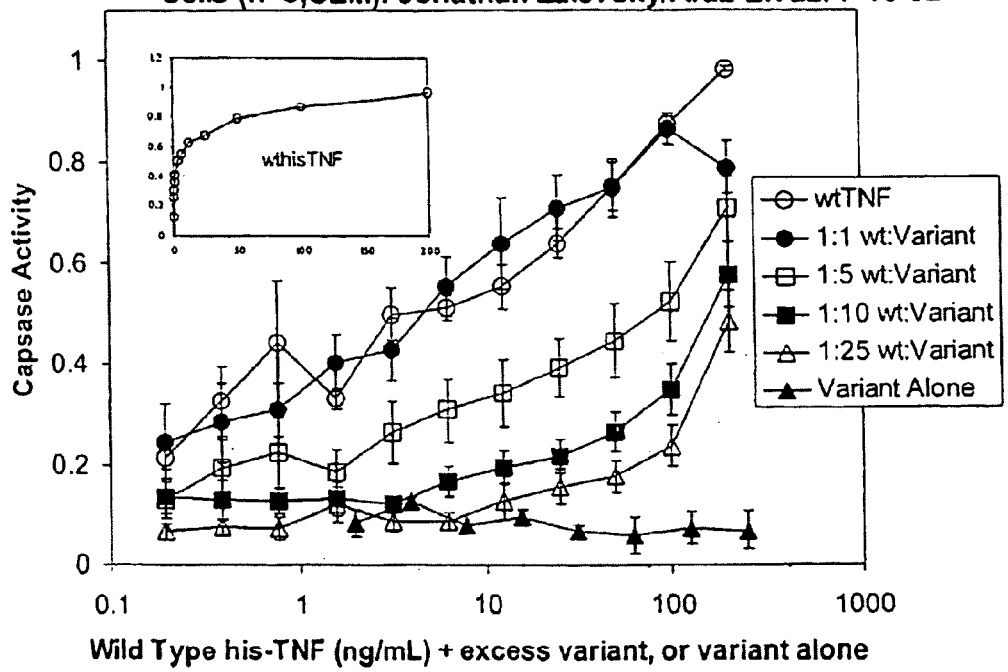
FIGS. 22A-C are dose response curves of caspase activation by various TNF variants.
Figure 22:
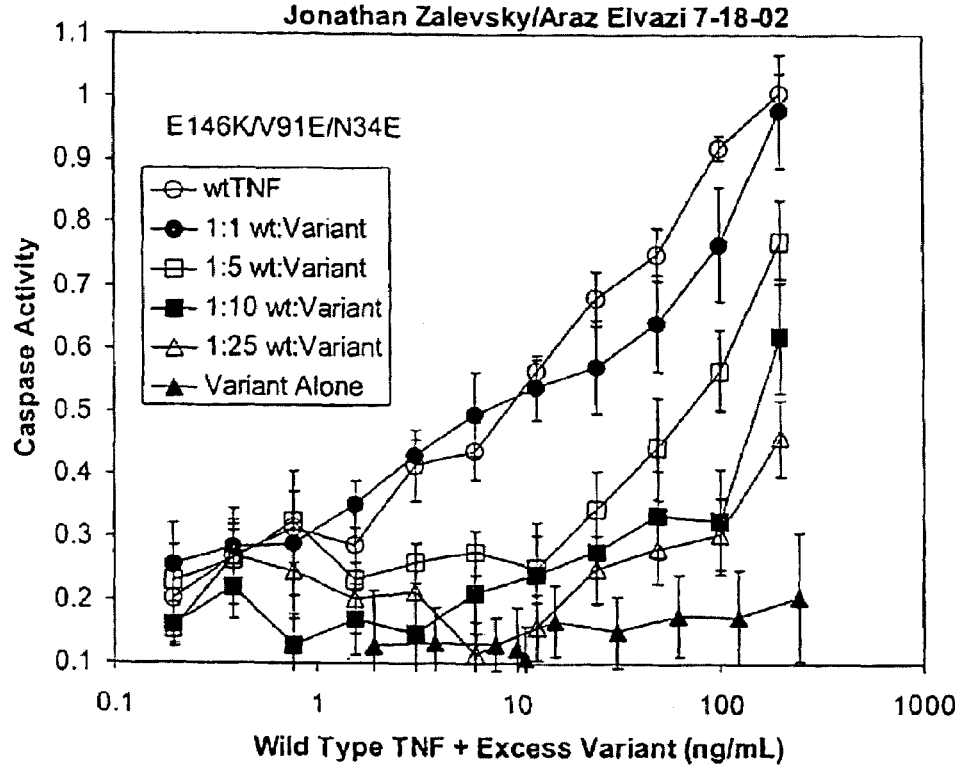
Figure 22:
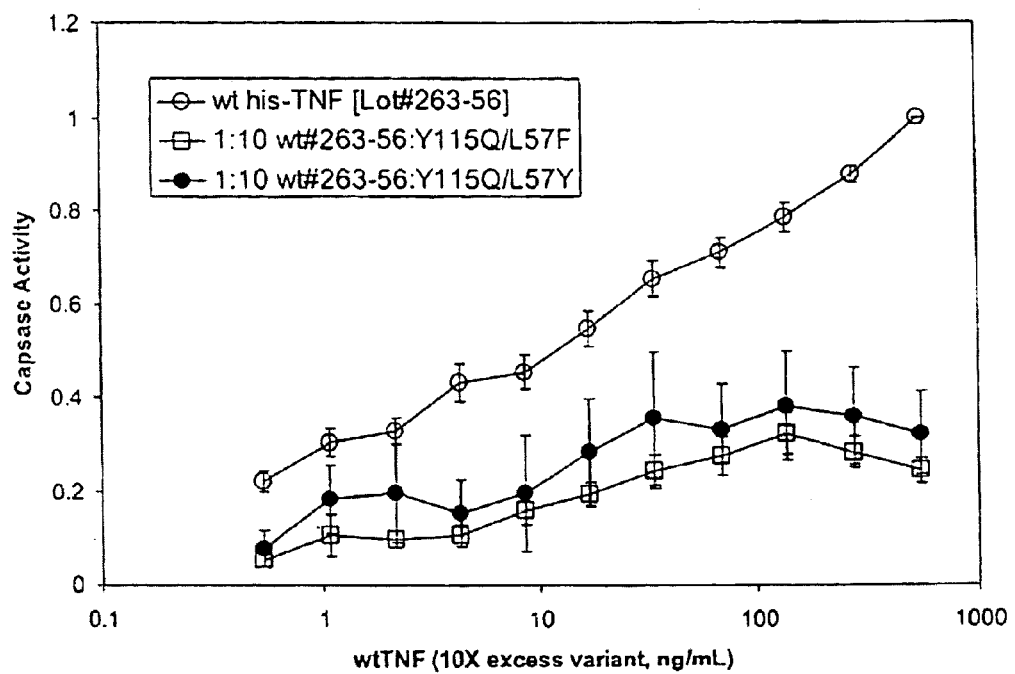

2) Caspase Assay: Warm full RPMI medium and supplement with 2 ug/mL Actinomycin D. Mix each entire 50 uL reaction with 450 uL Actinomycin D supplemented RPMI medium. This mixture is diluted 1:1 eleven times to generate a dose curve for the fixed equilibrium. 50 uL of the dilution mixture is applied to the cells in quadruplicate. Cells are incubated in the TNF-α/TNF-α variant fixed equilibrium for 1.5 hours. Upon completion of the incubation, add 100 ul of caspase substrate. Incubate for 1.5 hours. A R110 curve was also prepared by diluting the R10 standard 1:100 in RPMI followed by an 8-point half dilution. Then 100 ul of each dilution were added to a plate without cells, these dilutions are done right before adding the substrate to the cells. 100 ul of substrate was also added to R110 curve dilutions. Upon the completion of 1.5-hour incubation at 37 C, all samples were read using the Wallac fluorometer at 484/535 nm wavelengths. Results are shown in FIGS. 22A-C.

Example 6

Binding Assay

Biotinylation of TNFα was performed by adding 20 molar excess Sulfo-NHS-LC-biotin to the protein sample and incubating the sample on ice for 2 hours. Excess biotin was removed from the sample by dialysis. Coupling ratios ranged between 1 to 4. The protein concentration of biotinylated TNFα was determined by BCA protein assay (Pierce). Wells of a microtiter plate were coated with anti-FLAG antibody at a concentration of 2.5 mg/ml and blocked with 3% BSA overnight at 4° C. The FLAG-tagged protein TNFR1 receptor was added at a concentration of 10 ng/ml in PBS+1% BSA to wells of the anti-FLAG-coated microtiter plate, and the plate was incubated for 2 hours at room temperature. Biotinylated TNFa proteins ranging in concentrations from 0-1 mg/mL were added in quadruplicate to anti-FLAG-TNFR1-coated wells to represent total binding. Non-specific binding was measured by adding biotinylated TNFα proteins ranging in concentrations from 0-1 μg/ml in quadruplicate to wells coated only with anti-FLAG antibody. Binding was allowed to occur overnight at +4° C. to ensure equilibrium. Alkaline phosphatase conjugated neutravidin (Pierce) was added to the wells at 1:10,000 dilution in PBS+1% BSA and incubated for 30 min at room temperature. Luminescence was detected upon the addition of the CSPD star substrate (Applied Biosystems, Foster City, Calif.) and was measured (Wallac VICTOR, Perkin Elmer Life Sciences, Boston, Mass.). The specific binding of TNFa was calculated by subtracting non-specific binding from total binding. Data was fit to the binding equation y=(BLmax*x)/(Kd+x).

The results of the binding assays are shown in FIGS. 19 A-D. All variants show a decrease in receptor binding.

Example 7

TNF-α Variants Exchange with Wild Type TNF-α to Reduce Activation of NFk B

TNF-α variants tested were A145R, double variant A145R/Y87H, and triple variant E146K/V91E/N34E. His-tagged TNF-α was pre-incubated with 10-fold excess (1:10) of different variants for 3-days at 37 degrees C. Wild type TNF-α alone and pre-exchanged heterotrimers of TNF-α variants were then tested for their ability to activate an NFkB-driven luciferase reporter (pNFkB-luc, Clontech) in 293T cells. 293T cells were seeded at $1.2 \times 10^4$ cells/well in 96-well plates. Cells were then transfected with pNFkB-luc (NF-kB dependent luciferase reporter) or pTa1 (Control: basal promoter driving the luciferase gene, but without NFkB binding elements) using Fugene transfection reagent according to the manufacturer's protocol (Roche). 12 hrs after transfection, cells were treated with a final concentration of 10 ng/ml wild type TNF-α or a pre-exchanged mixtures of 10 ng/ml:TNF/100 ng/ml variant. 12 hrs after treatment, the cells in 96-well plates were processed for the luciferase assay using the Steady-Glo Luciferase Assay System (Promega) according to the manufacturer's protocol. Luminescence from each well was measured using the Packard TopCount NXT (Packard Bioscience) luminescence counter. Treated samples were tested in quadruplicates, and mean values of luminescence were plotted as bar values including the standard deviation for each treatment. The results are shown in FIG. 20A. The graph shows that the TNF-α variants of the present invention were effective in decreasing wild-type TNF-α induced NFkB activation. The TNF-α variant A145R/Y87H was most effective in decreasing TNF-α induced NFkB activation.

Example 8

Immuno-Localization of NFkB in HeLa Cells

HeLa cells were seeded onto 12 mm sterile coverslips (Fisherbrand) at a density of $1.5 \times 10^5$ cells/well in 6-well plates and cultured at 37 degrees C. at 5% CO2 atmosphere. The following day, the cells were treated with various concentrations of his-tagged wild type TNF-α, A145R/Y87H variant alone, or the combination of the his-tagged TNF-α and 10-fold excess of the A145/Y87H variant (pre-exchanged for three days at 37C) at 37° C., 5% CO2. After 30 minutes of incubation, the cells attached to coverslips in 6-well plates were briefly washed with PBS and fixed in 4% formaldehyde/PBS for 10 minutes. Cells were then washed an additional five times with PBS or maintained in the last PBS wash overnight before processing cells for immunocytochemistry. Fixed cells on coverslips were then treated with 0.1% Triton X-100/PBS. The buffer was aspirated and cells on coverslips were blocked in a humidified chamber for 15 minutes with 50 ul of 0.1% BSA/0.1% TX-100/PBS per coverslip at 37° C. The blocking reagent was then removed and replaced with primary antibody against p65 subunit of NF-kB (pAb C-20, Santa Cruz Bioscience). After one hour of incubation at 37 degrees C., the antibody was removed and coverslips were washed 5 times with PBS. 50 ul of FITC-conjugated secondary antibody (Jackson Immuno laboratories) diluted in blocking buffer (1:100) was added to each coverslip (Jackson Immuno laboratories) and coverslips were incubated in a light-safe humidified chamber for an additional hour before removing the secondary antibody with 5 washes of PBS. Coverslips were briefly rinsed with d-water, air-dried in a light-safe chamber and mounted onto slides using Anti-fade (Molecular Probes). Digital images of antibody-reacted cells were captured using a FITC filter and 40× objective on a Nikon Eclipse TS100 microscope coupled to a Cool SNAP-Pro CCD camera (Media Cybernetics) and operated using Image Pro Plus software (Media Cybernetics).

FIG. 20B shows photographs of the immuno-localization of NFkB in HeLa cells showing that the exchange of wild type TNF-α with the A145/Y87H TNF-α variant inhibits TNF-α-induced nuclear translocation of NFkB in HeLa cells. The TNF-α variant A145R/Y87H alone does not induce NFkB nuclear translocation, unlike the wild-type TNF-α. Moreover, the wild type TNF-α exchanged (3-days, 37 degrees C.) to form heterotrimers with excess variant (10 fold excess of TNF-α variant A145R/Y87H) loses its ability to induce NFkB nuclear translocation. This data is consistent with the effects of this variant in the luciferase reporter assay.

Example 9

Variant A145R/Y87H Reduced TNF-α Induced Activation of the NFkB-Driven Luciferase Reporter His-tagged wild type TNF-α, TNF-α variant A145/Y87H and the exchanged wild type TNF-α:A145R/Y87H heterotrimer (1-day exchange with 10-fold excess TNF-α variant A145R/Y87H at 37 degrees C.) were tested in the NFkB luciferase reporter assay as in Example 7A above. The experiment was carried out as in Example 7A, with the exception that a wider range of final TNF-α concentrations and increasing doses were used (0.78, 1.56, 3.13, 6.25, 12.5, 25 ng/ml) with 10-fold excess of TNF-α variant (A145R/Y87H) at each TNF-α concentration.

The wild type TNF-α: A145R/Y87H heterotrimer has a significantly reduced activation level, indicating the TNF-α A145R/Y87H variant's inhibitory effect on wild type TNF-α. Unlike wild type TNF-α, the TNF-α variant A145/Y87H alone has no significant agonizing effect on NFkB activation as shown by the lower dotted line in FIG. 20C. Wild type TNF-α induced activation is dependent on the NFkB activation as the reporter and without NFkB binding elements is unresponsive to the TNF-α as shown in the solid gray line in FIG. 20C.

Example 10

In Vivo *Listeria monocytogenes* Infection Using Variant TNF of the Present Invention Compounds The purpose of the experiment was to determine the effects of Xencor test materials on *L. monocytogenes*-induced mortality, blood and spleen bacterial content. A volume sufficient for 0.1 ml doses for 16 (20 g) mice for 12 days, plus overage (>1 dose per vial, plus extra vial) was used in the experiment. The sample vials were thawed at room temperature. Groups of mice were injected from a single needle, providing the specified dose for each animal by only injecting the proper volume and then withdrawing the needle, keeping the remaining solution in the needle for the next usage. This was repeated for all vials.

Figure 23:
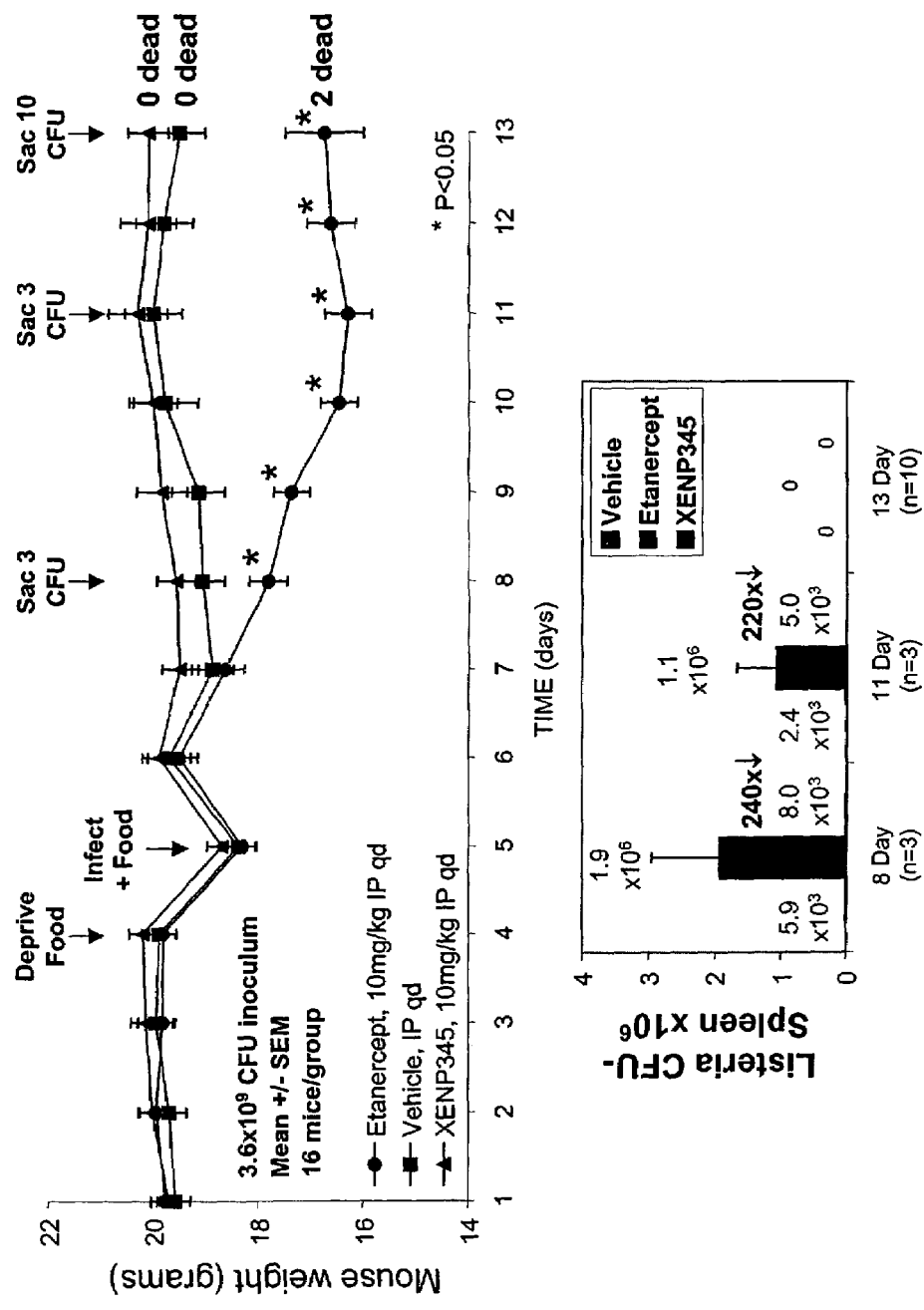
FIGS. 23A and B shows that a PEGylated TNF-α variant of the present invention when challenged by a *Listeria* infection has a reduced infection rate as compared to etanercept in a mouse *Listeria* infection model.

Mice (Balb/c, female, 6-8 wks, 16/treatment group) were received and quarantined for 72 hr. Three groups of mice (A, B, C) were treated equivalently with three compounds (A, B, C, i.e., A=etanercept, B=vehicle (PBS), C=XENP345). Mice were dosed daily for 5 days with test materials prior to infection (at 5 ml/kg ip qd). On Day 5 of trial, all mice were inoculated with $2 \times 10^9$ CFUs ($2 \times 10^{\wedge}9$) of *Listeria monocytogenes* (ATCC Strain 35152). Inoculum based on survival curves in gave an approximate LD25 on Day 5. Mice were dosed daily for further 7 days post-infection (until Day 12) with the compounds. Mice were weighed daily for the course of 13 day experiment and examined twice daily for signs of disease or distress. On Study Day 8 (Day 3 post-infection), three mice from each treatment group were euthanized, and their blood and spleens were evaluated for CFU. On Study Day 10 (Day 5 post-infection) post-infection, three mice from each treatment group were euthanized, and their blood and spleens were evaluated for CFU. At the termination of the experiment (Study Day 13, Day 8 post-infection), blood and spleens from the surviving mice were evaluated for CFU content. The results of this experiment shown in FIGS. 23A and 23B show that Soluble TNF-selective DN does not sensitize mice to *Listeria* infection and shows a reduction in the infection rate as compared to etanercept.

Example 11

In Vivo Efficacy of TNF-α Molecules of the Present Invention

Figure 24:
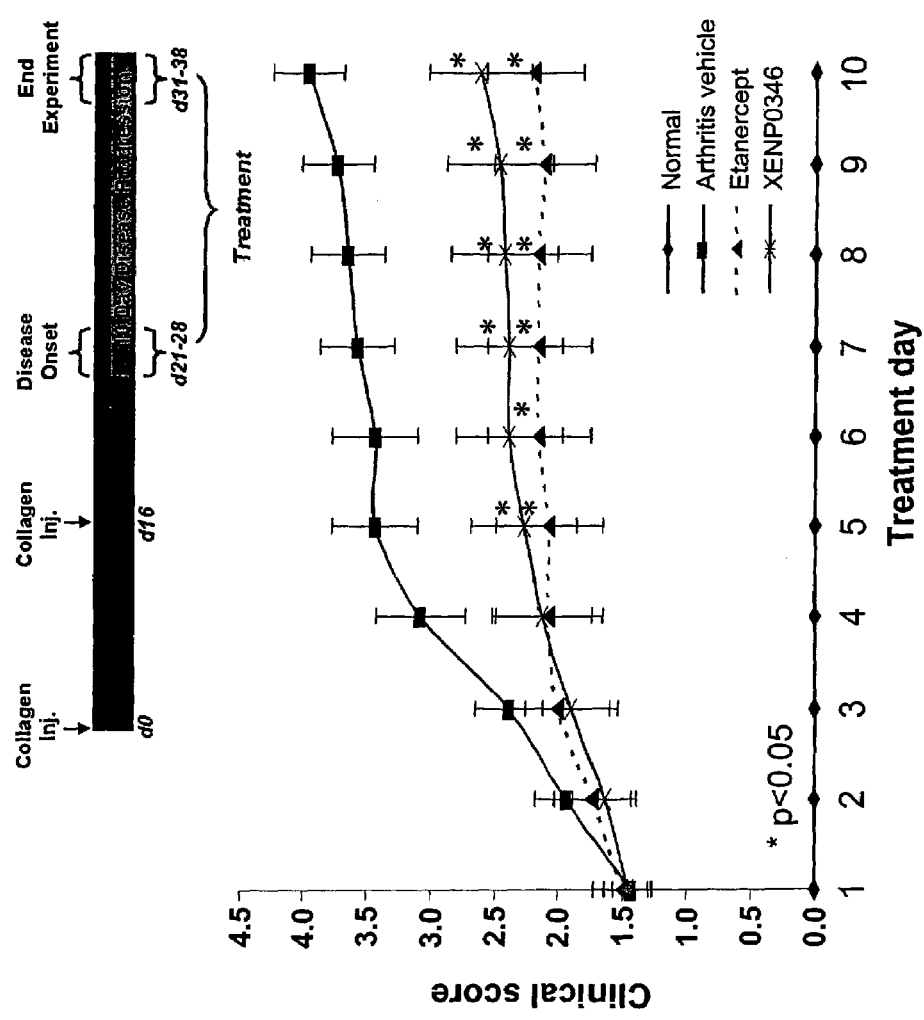
FIG. 24 shows the efficacy of a TNF-α molecule of the present invention against endogenous muTNF in a mouse DBA/1J mouse CIA model. The graph shows therapeutic treatment with a PEGylated TNF-α molecule of the present invention (5 mg/kg IP qd) has comparable in vivo efficacy as compared to etanercept. The bar above the graph shows the protocol of administration in the study.

In FIG. 24, the bar above the graph shows the protocol of administration in the study. XENP346 (identified below) was administered (5 mg/kg IP qd) in a mouse DBA/1J mouse CIA model according to the bar. The graph below shows the efficacy of a TNF-α molecule of the present invention against endogenous muTNF in a mouse DBA/1J mouse CIA model. The graph shows therapeutic treatment with a PEGylated TNF-α molecule of the present invention has comparable in vivo efficacy as compared to etanercept.

Example 12

Inhibition of solTNF and Effect on tmTNF Activity

FIG. 25 shows PEGylated TNF molecules of the present invention are selective for soluble TNF (solTNF). The variants shown in the top and bottom panels are different and are identified as "XENP No PEG" and "XENP+PEG". This data was generated using the human U937 caspase inhibition assay described herein. Caspase with TNF either free (recombinant human), or attached to the membrane of CHO cells (by a standard "delta1-12" deletion which removes the TACE cleavage site) is stimulated. All compounds (remicade, etancercept, PEGylated or non-PEGylated variant TNF-αs of the presention inhibit soluble TNF. Only remicade and etanercept block the tmTNF activity.

Figure 26:
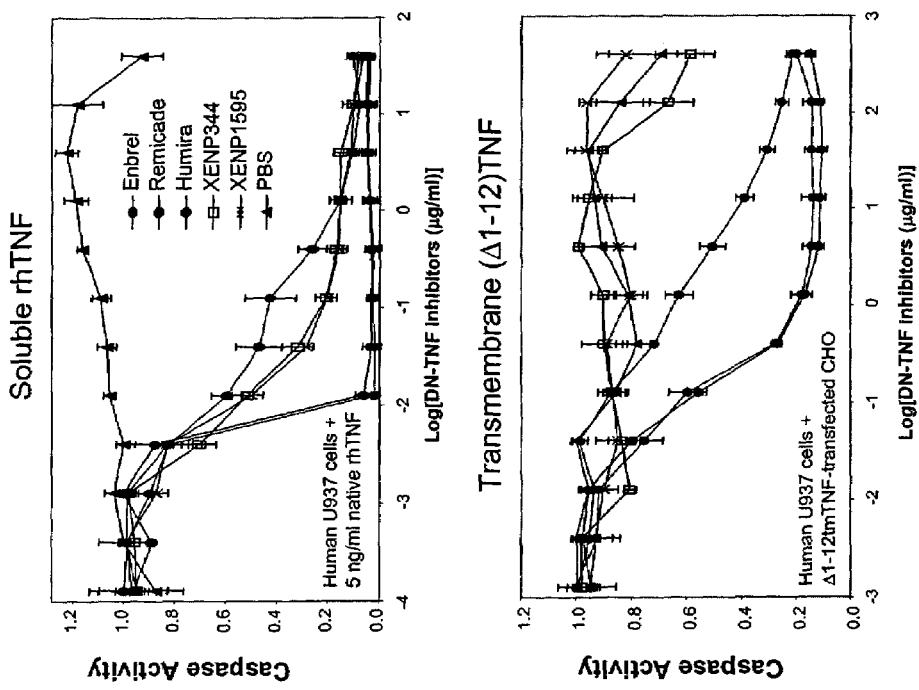
FIG. 26 shows the TNF-α molecules of the present invention inhibit only soluble TNF and spare transmembrane TNF (tmTNF) activity.
Figure 28:
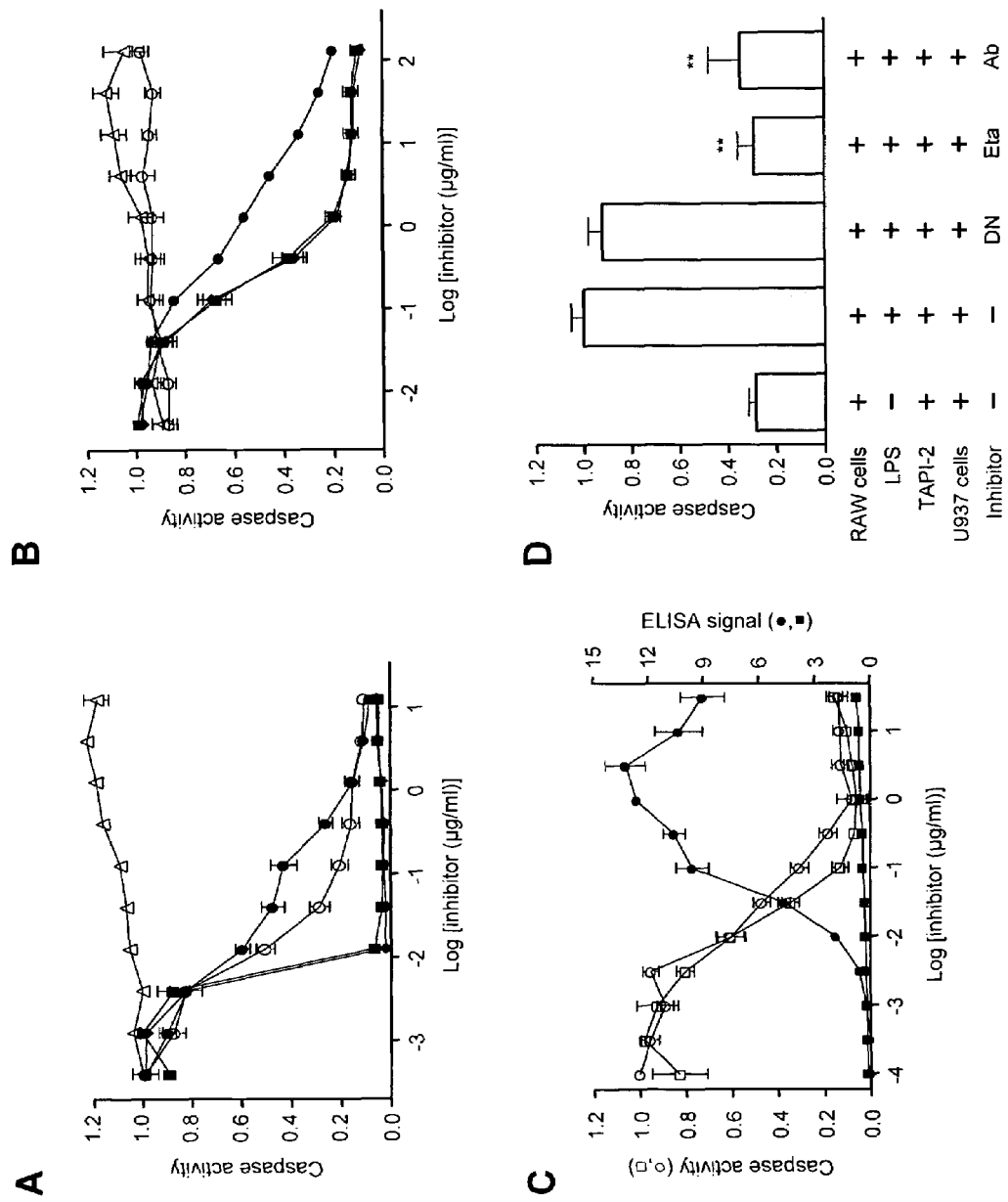
FIG. 28 shows that unlike etanercept, DN-TNF molecules are ligand selective TNF inhibitors that inhibit so are advantageous in the formulation of compounds which may have longer in vivo half lives, when administered by oral, intravenous, intramuscular, intraperitoneal, topical, rectal, intraocular, or other routes. In the preferred embodiment, the amino acids are in the S- or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. S218:U138-U138 Part 2 Aug. 22, 1999, both of which are incorporated by reference herein.

U937 cells were stimulated with Soluble vs. transmembrane TNF (tmTNF=D1-12-transfected CHO cells). Caspase assay shown here shows inhibition of TNF signaling (cf Scallon 2002 Centocor data). The graph shows Adalimumab, infliximab, etanercept inhibit sol & tmTNF and the TNF-α molecules of the present invention inhibit only solTNF and spare tmTNF. While not being limited to particular mechanistic theories, it is believed that the TNF-α molecules of the present invention may block the solTNF-mediated pro-inflammatory cascade, and yet spare tmTNF-mediated anti-inflammatory & anti-infective immune responses. FIG. 26 shows that the TNF molecules of the present invention inhibit only soluble TNF and spares transmembrane TNF activity.

Variant TNFs are engineered variants of native human TNF that cannot bind to either TNFR1 or TNFR2, but are able to exchange subunits with native solTNF to form inactive mixed heterotrimers (P. M. Steed et al., Science 301, 1895 (2003), incorporated by reference.) While antibodies and decoy receptors sequester active TNF, the present invention destroys the native TNF homotrimer and thus eliminate TNF signaling. We discovered that TNFs of the present invention exchange with and inhibit solTNF more effectively than tmTNF, which is a lipid-anchored type 11 transmembrane protein (C. Perez et al., Cell 63, 251 (1990); T. Utsumi et al., FEBS Lett. 500, 1 (2001), both incorporated by reference.) We established human and mouse cell-based experimental systems to study both solTNF- and tmTNF-induced cellular responses. For these studies we used two variant TNFs of the present invention, both potent inhibitors of solTNF that contain identical A145R and Y87H receptor-blocking mutations (H. Loetscher, et. al, J. Biol. Chem. 268, 26350 (1993), incorporated by reference.) XENP267 (FIGS. 28C and 28D) contains an amino-terminal 6-histidine tag to simplify detection of heterotrimer formation between mouse solTNF and variant TNF of the present invention, whereas XENP1595 (FIGS. 28A, 28B, and 29) is untagged and conjugated with a site-specific 10 kD polyethylene glycol (PEG) side chain for improved half-life in animal models. Neither the tag nor the site-specific PEG affect the bioactivity of these molecules. We first compared the potency of XENP1595, etanercept, infliximab, and adalimumab in blocking caspase activation induced by either soluble or transmembrane human TNF in human monocyte-like U937 cells (FIGS. 28A and 28B). All compounds inhibited recombinant human solTNF in a dose-dependent fashion (FIG. 28A); the two antibodies were most potent (IC50 ~7 ng/ml), followed by XENP1595 (IC50 ~15 ng/ml) and etanercept (IC50 ~35 ng/ml). To study the effects of the three classes of inhibitors on tmTNF-induced juxtacrine signaling, we developed a co-culture assay using cells expressing human tmTNF mixed with TNF-responsive human cells. CHO cells were transfected with a human TNF construct lacking the first twelve amino acids of processed solTNF (D1-12proTNF), generating bioactive tmTNF that is not shed from the cell surface (20, 24). We incubated these cells overnight with increasing amounts of TNF inhibitors and the next day mixed with U937 cells to induce caspase activity (FIG. 28B). In agreement with previous results, adalimumab, infliximab, and etanercept inhibited human tmTNF, with the two antibodies being more potent than the decoy receptor (IC50 ~300 ng/ml for adalimumab and infliximab, ~3 μg/ml for etanercept). In contrast, XENP1595 failed to inhibit tmTNF-induced caspase activation even at a dose of >100 μg/ml.

To validate the human D1-12proTNF vs. solTNF selectivity results and to prepare for efficacy studies in mouse models, we next tested the ability of variant TNF of the present invention, etanercept, and an anti-mouse TNF neutralizing antibody to inhibit endogenously produced mouse solTNF and tmTNF. To generate physiological levels of endogenous solTNF, we incubated mouse macrophage-like RAW264.7 cells with lipopolysaccharide (LPS) for 3 h and collected medium containing ~10 ng/ml secreted TNF. We added increasing concentrations of XENP267 or etanercept and incubated an additional 60 min. The samples were then divided, with part used to stimulate caspase activation in U937 cells, and the remaining material used in a sandwich ELISA to measure heterotrimer formation between mouse solTNF and variant TNF of the present invention (FIG. 28C). These results show that etanercept and variant TNF of the present invention are equally effective inhibitors of endogenous murine and recombinant human solTNF, and that variant TNF of the present invention acts through heterotrimer formation. To generate mouse cells producing only endogenous tmTNF, we next screened a panel of small-molecule inhibitors of TNF convertase (TACE) and discovered that 10 μM TAPI-2 effectively blocks TACE-mediated cleavage of LPS-induced murine tmTNF on RAW264.7 cells. We treated LPS-stimulated RAW264.7 cells with TAPI-2, added human U937 cells, and measured caspase activation induced by murine tmTNF. Under these conditions, all TNF produced is transmembrane; we failed to detect any solTNF either by ELISA or bioassay (data not shown). In this assay of juxtacrine signaling, 10 mg/ml etanercept or anti-mouse TNF antibody completely blocks murine tmTNF-mediated caspase activation, while variant TNF of the present invention has no effect (FIG. 28D). Thus, differential inhibition of endogenous murine solTNF and tmTNF signaling by variant TNF of the present invention corroborates our results using the human orthologs; in both cases, variant TNF of the present invention blocks solTNF but does not inhibit tmTNF, in contrast to the decoy receptor and antibodies.

We have shown that variant TNF of the present invention is anti-inflammatory even when dosed after onset of symptoms in a collagen-induced arthritis (CIA) model in rats. To test our hypothesis that solTNF-selective inhibitors can block inflammation without compromising innate immunity, we first compared the efficacy of variant TNF of the present invention and etanercept in a mouse model of arthritis. We used the anti-collagen antibody-induced arthritis (ACAIA) (27) model, in part because this model eliminates the bacterial co-stimulus of killed *Mycobacterium tuberculosis* required to induce joint inflammation in standard mouse CIA models, such as those used to demonstrate etanercept efficacy (P. H. Wooley, J. Dutcher, M. B. Widmer, S. Gillis, J. Immunol. 151, 6602 (1993), incorporated by reference.) In the ACAIA model, XENP1595 reduced disease symptoms dose-dependently, quantified either by arthritis score (FIG. 29A) or paw edema (FIG. 29B). Etanercept and XENP1595 were similarly effective in this model, with 10 mg/kg/day doses of either compound reducing arthritis score and edema by 30% and 28%, respectively. These results demonstrate that a solTNF-selective variant TNF of the present invention is comparable in efficacy to a dual solTNF and tmTNF-inhibiting decoy receptor in an established murine model of arthritic inflammation.

Figure 29:
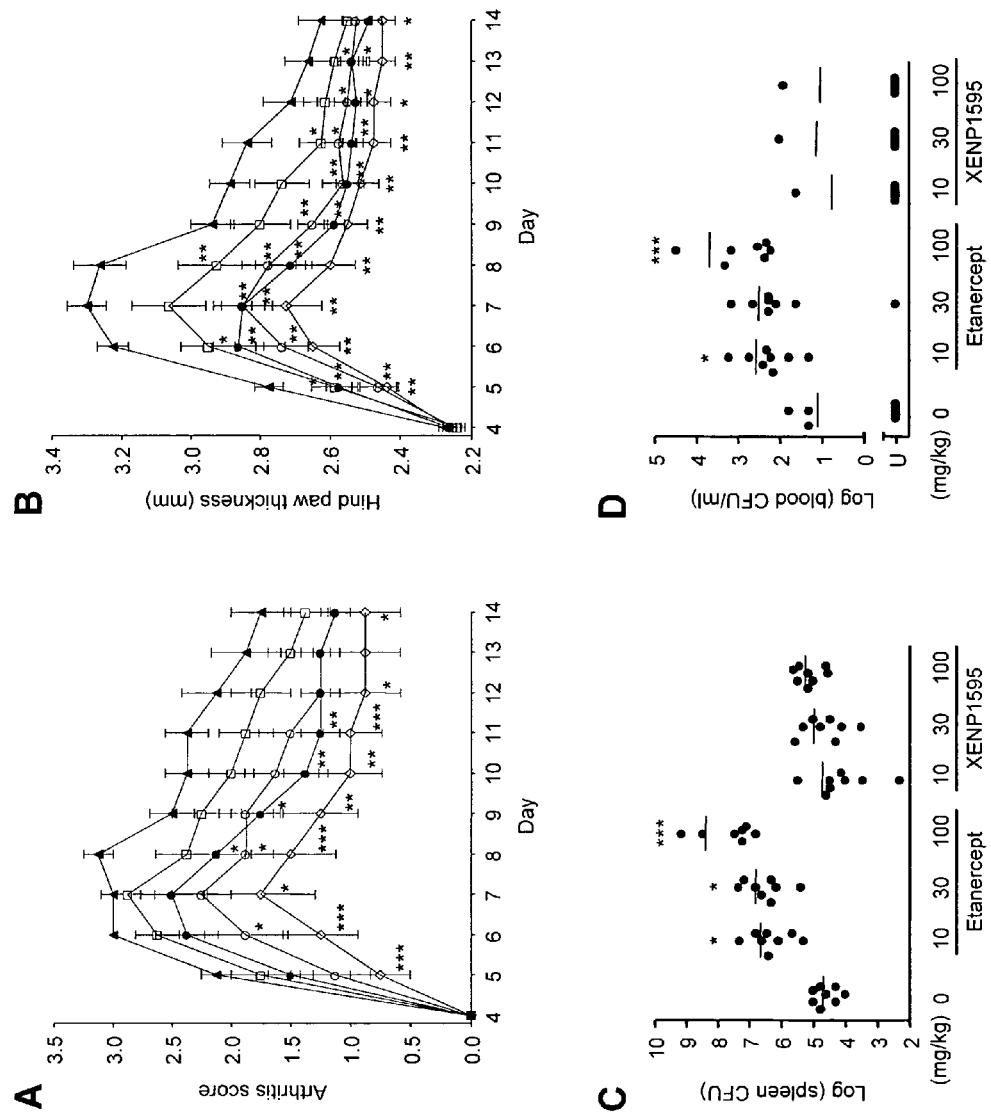

To assess the influence of solTNF-selective inhibition on innate immunity, we compared variant TNF of the present invention to etanercept in a mouse model of *Listeria monocytogenes* infection. Based on the near-normal ability of solTNF knockout/tmTNF knock-in mice to resist mycobacterial and listerial infections (M. L. Olleros et al., J. Immunol. 168, 3394 (2002); M. Pasparakis, et al., J. Exp. Med. 184, 1397 (1996), both incorporated by reference,) we discovered that a tmTNF-sparing anti-inflammatory agent would likewise avoid compromising host immune response to infection. We dosed mice daily with etanercept or variant TNF of the present invention (XENP1595) at 10, 30, and 100 mg/kg/day. After three days, mice received a 4×10⁹ oral inoculum of *L. monocytogenes*; after an additional three days of drug treatment we determined bacterial load in the spleen (FIG. 29C) and blood (FIG. 29D). In both organs, etanercept greatly increased bacterial load (by factors of 90, 125, and 5,000 in spleen and 30, 25, and 390 in blood at the 10, 30, and 100 mg/kg doses, respectively) compared to vehicle-treated mice. In contrast, even the highest dose of variant TNF of the present invention did not significantly increase bacterial load in spleen or blood relative to vehicle. In particular, only 3 of 24 mice in XENP1595 dose groups had any detectable bacteria in the blood, vs. 23 of 24 in the etanercept groups. *Listeria*, like the mycobacteria, is an intracellular pathogen in mice as in humans, therefore, detectable listeremia is evidence of a severe infection. The minimal number of bacteria in the blood of variant TNF of the present invention-treated mice indicates that these mice mounted an immune response indistinguishable from vehicle-treated normal mice.

Therapeutics of the present invention inhibit soluble TNF-induced paracrine signaling yet spare juxtacrine signaling events mediated by transmembrane TNF. The unique ligand selectivity profile of variant TNF of the present invention contrasts with existing decoy receptor and antibody drugs that inhibit both solTNF and tmTNF activities. We demonstrate that variant TNF of the present invention has similar anti-inflammatory activity to etanercept in a murine model of arthritis, but unlike etanercept, does not compromise the normal innate immune response to *Listeria* infection.

FIG. 27 lists possible variants of TNF-α based upon this TNF-α root sequence.

Example 13

Rational Pegylation of Variant TNF-α

Rational pegylation was conducted as previously described. FIG. 31 describes our rational PEGylation design strategy. In order to facilitate effective sulfhydral chemistry we first disrupted the two endogenous cysteines in TNF (cys 69 mutated to val and cys 101 mutated to ala), and then introduced a novel cysteine at amino acid position 31. This molecule is quite easily PEGylated after a 20-minute treatment with a 3-fold excess of PEG (FIG. 32 left panel). The left panel of FIG. 32 shows the specificity and completeness of the PEGylation reaction. This PEGylation method (i.e. site-specific maleimide chemistry) is superior to most PEG chemistries that result in a high molecular weight smear that contains multiple forms of PEG-containing proteins since the reaction produces a single PEGylated protein species. FIGS. 33 and 34 demonstrate that site-specific PEGylation does not interfere with the intrinsic bioactivity of the DN-TNF. The top panel of FIG. 33 shows a kinetic assay to measure the rate of heterotrimer formation. PEGylated or unPEGylated DN-TNF or native were mixed with alexa568-conjugated native TNF (a fluorescently modified TNF molecule that exhibits low anisotropy as a homotrimer but high anisotropy as a heterotrimer therefore making it an excellent tracer compound for measuring the rate of heterotrimer formation) in PBS and the reaction was continuously measured under real time in a fluorometer. We made two important findings 1) that DN-TNFs exchange with native TNF faster than native TNF exchanges with itself and 2) PEGylated and unPEGylated DN-TNFs exchange with equal rates. The bottom panel of FIG. 33 shows a native PAGE that resolves the steady state exchange products between PEGylated DN-TNF and PEGylated or unPEGylated DN-TNF. Briefly, samples were mixed at equal parts in a PBS/0.02% igepal-containing buffer and incubated at 4C overnight to reach equilibrium. These samples were run on native PAGE to resolve the respective homo- or heterotrimers. Thus FIG. 33 shows that PEGylation at R31 has no effect on either the kinetics or steady products of heterotrimer formation. The right panel of FIG. 34 shows that either PEGylated or unPEGylated DN-TNF proteins have equal antagonistic properties as determined by the induction of caspase signaling (see above). We determined the effect of PEGylation on increasing the molecule's half-life by doing a single intravenous bolus dose administered at 2 mg/kg into male rats. Native TNF clears rapidly (terminal half-life ~30-minutes) while PEGylated TNF has a vastly longer terminal half-life. In order to obtain more high-resolution pharmacokinetic data we used the chloramines-T method to conjugate 1125 to the PEGylated DN-TNF. Using these compounds we did additional pharmacokinetic studies using a 1 mg/kg administration via either intravenous or subcutaneous route. FIG. 35 shows the results of these experiments, we observed a decrease in the overall terminal elimination rate as a function of increasing PEG size. This translates into a longer terminal half-life with PEG-5 kD ~17-hours, PEG-10 kD ~20-hours, and PEG-20 kD ~30-hours. To evaluate the fractional absorption (bioavailability) of these compounds we determined the area under the curve (AUC) and expressed this as a ratio of subcutaneous AUC divided by the intravenous AUC. FIG. 36 shows that the greatest bioavailability was observed by the protein conjugates with the smallest PEG (i.e. ~42% for the PEG-5 kD). We took all the pharmacokinetic data obtained from these studies and generated repeat dose modeling simulation allometrically scaled to human. We reasoned that the volume and absorption parameters would remain unchanged and the terminal elimination would allometrically scale by a factor of 6.2×. From these input parameters we examined repeat subcutaneous administration every 7, 10, and 14 days. The results of these simulations are shown in FIG. 37 and they demonstrate that dosing every 10 days could likely provide a trough concentration of ~500 ng/mL.

FIGS. 38 and 39 demonstrate that either native or DN-TNFs effectively exchange with mouse, rat, or human TNF. FIG. 38 shows a native PAGE that resolves the steady state exchange products between PEGylated DN-TNF and native mouse or human TNF. Briefly, samples were mixed at equal parts in a PBS/0.02% igepal-containing buffer and incubated at 4C overnight to reach equilibrium. These samples were run on native PAGE to resolve the respective homo- or heterotrimers. FIG. 39 shows a kinetic assay to measure the rate of heterotrimer formation. Human or rat native TNF were mixed with alexa568-conjugated native TNF (a fluorescently modified TNF molecule that exhibits low anisotropy as a homotrimer but high anisotropy as a heterotrimer therefore making it an excellent tracer compound for measuring the rate of heterotrimer formation) in a PBS/0.02% igepal-containing buffer and the reaction was continuously measured under real time in a fluorometer. We observe an equal exchange rate between alexa568-conjugated TNF and either human or rat TNF.

The codes used in the figures and experiments described herein are based upon SEQ ID NO. 1 (also referred to as "wild-type TNF-α sequence" and/or "root TNF-α sequence"):

<0001<VRSSSRTPSDKPVAHVVANPQAEGQLQWLNRRANALLANG
VELRDNQLVVPSEGLYLIYSQVLFKGQGCPSTHVLLTHTISRIAVSY
QTKVNLLSAIKSPCQRETPEGAEAKPWYEPIYLGGVFQLEKGDRLS
AEINRPDYLDFAESGQVYFGIIAL>0157>.
(SEQ ID NO:12)

The codes used in the Figures and experiments above disclose the following TNF-α variants of the present invention:

| Name | Modifications |
|---|---|
| XENP268 | <001<-I097T-A145R->157> with MHHHHHH (SEQ ID NO:13) as N-terminal "tag" |
| XENP344 | <001<-V0001M-R0031C-μ0031Peg5-C0069V-Y0087H-C0101A-A0145R->0157> |
| XENP345 | <001<-V001M-R031C-μ031Peg5-C069V-I097T-C101A-A145R->157> |
| XENP346 | <001<-V001M-R031C-μ031Peg10-C069V-I097T-C101A-A145R->157> |
| XENP550 | <001<-V001M-R031C-C069V-Y087H-C101A-A145R->157> |
| XENP551 | <001<-V001M-R031C-C069V-I097T-C101A-A145R->157> |
| XENP557 | <001<-V001L-R031C-C069V-Y087H-C101A-A145R->157>, with M as N-terminal "tag" |
| XENP1593 | <001<-V001M-R031C-μ031Peg40-C069V-Y087H-C101A-A0145R->157> |
| XENP1594 | <001<-V001M-R031C-μ031Peg20-C069V-Y087H-C101A-A0145R->157> |
| XENP1595 | <001<-V001M-R031C-μ031Peg10-C069V-Y087H-C101A-A0145R->157> |

The "μ" means a modification at that position that is not an amino acid change. Thus, "R031C-μ031 Peg5" means both an amino acid change and a pegylation with 5 kD PEG at position 31.

Whereas particular embodiments of the invention have been described above for purposes of illustration, it will be appreciated by those skilled in the art that numerous variations of the details may be made without departing from the invention as described in the appended claims. All references described above are herein incorporated by reference.

We claim:

1. A method of selectively inhibiting the activity of wild-type soluble Tumor necrosis factor-α (TNF-α) in a human comprising administering to said human a molecule that inhibits the activity of soluble TNF-α while substantially maintaining the activity of transmembrane TNF-α, wherein said molecule is a variant TNF-α as compared to human wild-type TNF-α (SEQ ID NO: 12), wherein said TNF-α variant comprises the amino acid modifications Y87H and A145R or I97T and A145R.

2. A method of claim 1, wherein said TNF-α variant is substantially free of agonistic activity.

3. A method of selectively inhibiting the activity of wild-type soluble TNF-α as compared to the activity of transmembrane wild-type TNF-α in a mammal comprising administering to said mammal a variant TNF-α molecule as compared to the wild-type human TNF-α of SEQ ID NO:12, wherein said TNF-α variant is substantially free of agonistic activity, wherein said TNF-α variant comprises the amino acid modifications Y87H and A145R or I97T and A145R.

4. A method of forming a TNF-α heterotrimer comprising contacting a variant TNF-α molecule as compared to the wild-type human TNF-α of SEQ ID NO:12 with the wild type TNF-α, under conditions whereby a heterotrimer is formed, wherein said TNF-α variant is substantially free of agonistic activity, wherein said TNF-α variant comprises the amino acid modifications Y87H and A145R or I97T and A145R.

5. A method according to claim 2, 3 or 4, wherein the agonistic activity of said TNF-α variant is reduced by at least 50%.

6. A method of claim 1, wherein said TNF-α variant comprises the amino acid modifications Y87H and A145R.

7. A method of claim 1, wherein said TNF-α variant comprises the amino acid modifications I97T and A145R.

8. A method of claim 6 or 7, wherein said variant further comprises the amino acid modification R31C.

9. A method according to claim 8, wherein said variant TNF-α comprises polyethylene glycol.

10. A method according to claim 8, wherein said variant further comprises an amino acid modification at position 101.

11. A method of claim 10, wherein said modification is C101A.

12. A method of claim 6 or 7, wherein said variant further comprises the amino acid modification V1M.

13. A method according to claim 12, wherein said variant further comprises an amino acid modification at position 101.

14. A method of claim 13, wherein said modification is C101A.

15. A method of claim 6 or 7, wherein said variant further comprises an amino acid modification at position 69.

16. A method of claim 15, wherein said modification is C69V.

17. A method of claim 6 or 7, wherein said variant further comprises an amino acid modification at position 101.

18. A method of claim 17, wherein said modification is C101A.

19. A method of claim 1, wherein said variant TNF-α comprises the amino acid substitutions V1M, R31C, C69V, Y87H, C101, and A145R.

20. A method of claim 1 wherein said TNF-α variant is selected from the group consisting of XENP268, XENP344, XENP345, XENP346, XENP550, XENP551, XENP557, XENP1593, XENP1594, and XENP1595.

* * * * *

UNITED STATES PATENT AND TRADEMARK OFFICE
CERTIFICATE OF CORRECTION

| | | |
|---|---|---|
| PATENT NO. | : 7,446,174 B2 | Page 1 of 1 |
| APPLICATION NO. | : 11/108001 | |
| DATED | : November 4, 2008 | |
| INVENTOR(S) | : John R. Desjarlais et al. | |

It is certified that error appears in the above-identified patent and that said Letters Patent is hereby corrected as shown below:

In claim 19 Column 66, line 38, please correct the line to read:

--Y87H, C101A, and A145R.--

Signed and Sealed this

Twenty-ninth Day of June, 2010

David J. Kappos
*Director of the United States Patent and Trademark Office*